United States Patent [19]

Yamada et al.

[11] Patent Number: 5,064,945
[45] Date of Patent: * Nov. 12, 1991

[54] CHARTREUSIN DERIVATIVES AND SALTS THEREOF

[75] Inventors: Nobutoshi Yamada; Hideo Sugi; Kenji Kon, all of Moriyama, Japan

[73] Assignee: Ishihara Sangyo Kaisha, Ltd., Osaka, Japan

[ * ] Notice: The portion of the term of this patent subsequent to May 22, 2007 has been disclaimed.

[21] Appl. No.: 427,370

[22] Filed: Oct. 27, 1989

Related U.S. Application Data

[62] Division of Ser. No. 922,433, Oct. 23, 1988, Pat. No. 4,927,919.

[30] Foreign Application Priority Data

Oct. 23, 1985 [JP] Japan .................................. 60/236833

[51] Int. Cl.$^5$ .............................................. C07H 17/04
[52] U.S. Cl. .................................. 536/17.5; 536/17.2; 536/18.1
[58] Field of Search ..................... 536/17.2, 17.5, 18.1

[56] References Cited

U.S. PATENT DOCUMENTS 4,760,136 7/1988 Mori et al. ........................ 536/17.5

OTHER PUBLICATIONS

Ogawa, Y. et al. "The Absolute Structures of Rubeomycins A and $A_1$, (Carminomycins II and III) and Rubeomycins B and $B_1$ (4–Hydroxybaumycinols $A_1$ and $A_2$)", *The Journal of Antibiotics*, vol. 37, (1), Jan. 1984, pp. 44–56.

Ogawa, Y. et al., "Rubeomycin, A New Anthracycline Antibiotic Complex—I. Taxonomy of Producing Organism, Isolation, Characterization and Biological Activities of Rubeomycin A, $A_1$, and B and $B_1$." *The Journal of Antibiotics*, vol. 34 (8), Aug. 1981, pp. 938–950.

*Primary Examiner*—Elli Peselev
*Attorney, Agent, or Firm*—Cushman, Darby & Cushman

[57] ABSTRACT

This invention relates to a novel chartreusin derivative of the general formula (I):

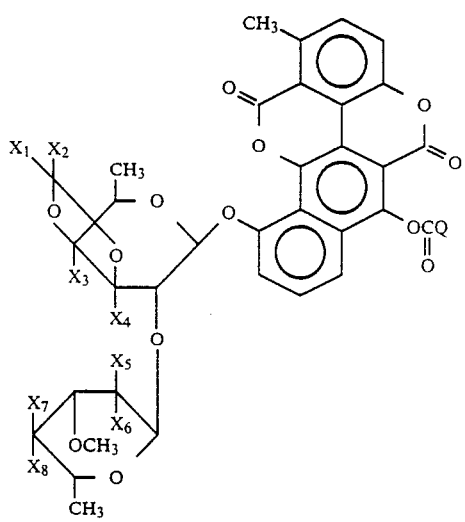

and a salt thereof. This chartreusin derivative and a salt thereof have an excellent antitumor activity, which is exhibited even when the site of cancer inoculation and the site of drug administration are different. This invention further relates to an antitumorous composition containing the above-mentioned compound as active ingredient. This invention furthermore relates to a process for producing the above-mentioned chartreusin derivative or salt thereof.

20 Claims, No Drawings

CHARTREUSIN DERIVATIVES AND SALTS THEREOF

This is a division of application Ser. No. 06/922,433 filed Oct. 23, 1988, which issued as U.S. Pat. No. 4,927,919 on May 22, 1990.

This invention relates to a chartreusin derivative, a salt thereof, antitumorous compositions containing the same, a process for producing the same, and an intermediate thereof. The compounds of this invention, i.e., the chartreusin derivative and a salt thereof are useful compounds having an antitumor activity in laboratory animals such as mouse.

Chartreusin is an antibiotic which was originally reported by B. E. Leach et al. in 1953 [J. Am. Chem. Soc., 75 4011–4012 (1953)]. It was also submitted to the National Cancer Institute (NCI) of U.S.A. for reevaluation of antitumor activity of natural products and given a NCI number of NSC-5159. Thereafter, details of its antitumor activity were reported in Cancer Research 37, 1666–1672 (1977) as the results of joint research of NCI. In this report, it is reported that chartreusin was effective against P-388 leukemia, L-1210 leukemia and B-16 melanoma. However, it is also reported in the same literature that this effect was obtained in a system in which cancer was inoculated intraperitoneally, followed by intraperitoneal administration of chartreusin, and that chartreusin was not effective at all when the site of cancer inoculation and the site of chartreusin administration were different. As a cause for this, it is pointed out therein that biliary excretion of chartreusin essentially has the precedence over absorption thereof to tissues.

There was attempted conversion of the saccharide moiety, namely, conversion of D-fucose and D-digitalose into β-D-maltosyl or the like, but the resulting product was not effective when the site of cancer inoculation and the site of drug administration were different [J. Med. Chem., 23 549–553 (1980)]. Under these circumstances, chartreusin has not yet been developed.

On the other hand, it is described in U.S. Pat. No. 4,518,589 that one antibiotic complex, i.e., BBM-2478A is effective against P-388 leukemia, L-1210 leukemia and B-16 melanoma in a system in which cancer was inoculated intraperitoneally, followed by intraperitoneal administration of BBM-2478A. However, the chemical structures of the compounds of this invention are utterly different from that of BBM-2478A in the 6-position of aglycone moiety and the 3'-position and 4'-position of saccharide moiety.

The present inventors perceived the excellent antitumorous activity of chartreusin, and have conducted extensive research to allow the chartreusin derivative to always exhibit its excellent activity even when the site of cancer inoculation and the site of administration of the chartreusin derivative are different. As a results, the present inventors have found novel chartreusin derivatives and salts thereof which exhibit an excellent antitumorous activity even when the site of cancer innoculation and the site of drug administration are different, for example, when cancer is intraperitoneally inoculated and the drug is intravenously administered, or when cancer is subcutaneously inoculated and the drug is intravenously administered, whereby this invention has been accomplished.

This invention relates to a chartreusin derivative of the following general formula, a salt thereof, antitumorous compositions containing the same, a process for producing the chartreusin derivative or the salt thereof, and in intermediate thereof:

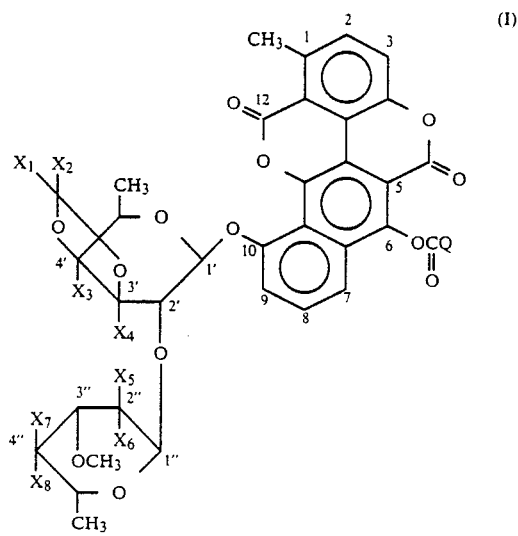

(I)

wherein $X_1$ is a hydrogen atom or a substituted or unsubstituted $C_{1-3}$alkyl group; $X_2$ is a substituted or unsubstituted $C_{1-3}$alkyl group, a substituted or unsubstituted $C_{1-2}$alkylcarbonyl-$C_{1-2}$alkyl group, a substituted or unsubstituted phenyl group, a substituted or unsubstituted phenyl-$C_{1-2}$alkyl group, a substituted or unsubstituted furyl group or a substituted or unsubstituted thienyl group; in the case where $X_1$ and $X_2$ are both substituted or unsubstituted alkyl groups at the same time, the total number of carbon atoms of these alkyl groups is 4 or less; in the case where $X_2$ is a substituted or unsubstituted phenyl group, a substituted or unsubstituted phenylalkyl group, a substituted or unsubstituted furyl group or a substituted or unsubstituted thienyl group, $X_1$ is a hydrogen atom; $X_1$ and $X_2$, when taken together with the adjacent carbon atom, may form a substituted or unsubstituted $C_{3-7}$cycloalkylidene; each of $X_3$ and $X_4$ is a hydrogen atom or a methyl group; in the case where $X_3$ is a methyl group, $X_4$ is a hydrogen atom; $X_5$ is a hydrogen atom, a hydroxyl group or an amino group; $X_6$ is a hydrogen atom or a hydroxyl group; $X_5$ and $X_6$ may be bonded to the same oxygen atom at the same time; in the case where $X_5$ is a hydroxyl group or an amino group, $X_6$ is a hydrogen atom; $X_7$ is a hydrogen atom or an amino group; $X_8$ is a hydrogen atom or a hydroxyl group; in the case where $X_7$ is an amino group, $X_8$ is a hydrogen atom; Q is a substituted or unsubstituted $C_{1-11}$alkyl group, a substituted or unsubstituted $C_{2-11}$alkenyl group, a substituted or unsubstituted $C_{3-11}$alkynyl group, a substituted or unsubstituted $C_{3-10}$cycloalkyl group, a substituted or unsubstituted $C_{5-10}$cycloalkenyl group, a substituted or unsubstituted $C_{1-10}$alkylcarbonyl group, a substituted or unsubstituted $C_{1-10}$alkoxycarbonyl group, a substituted or unsubstituted phenyl group, or a substituent represented by any of the general formulas (a) to (i):

group,

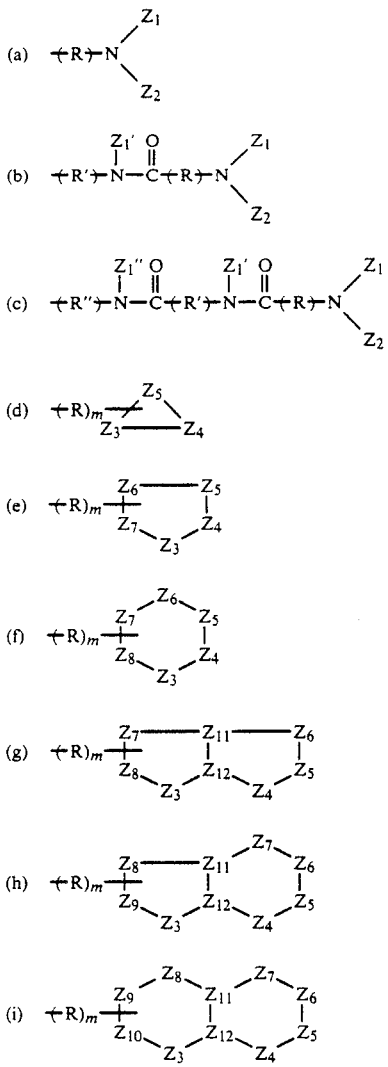

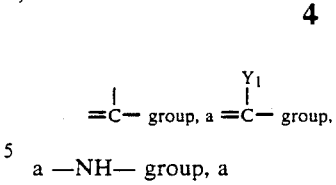

a —NH— group, a

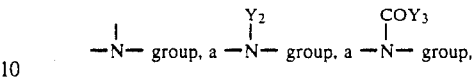

a =N— group, an oxygen atom or a sulfur atom; each of $Z_{11}$ and $Z_{12}$ is a

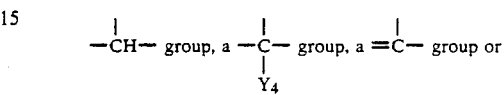

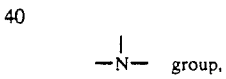

any one of $Z_3$ through $Z_{10}$ is a

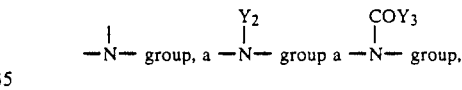

each of the others being a substituent other than these three substituents, and any one of $Z_3$ through $Z_{10}$ is a —NH— group, a

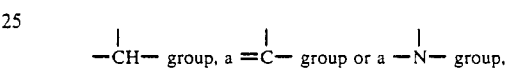

a =N— group, an oxygen atom or a sulfur atom, m being zero in the case where any one of $Z_3$ through $Z_{10}$ is a

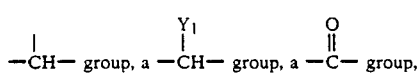

(in these nine formulas, each of R, R' and R" is a substituted or unsubstituted $C_{1-11}$alkanediyl group, a substituted or unsubstituted $C_{2-11}$alkenediyl group, a substituted or unsubstituted $C_{2-11}$alkyenediyl group, a substituted or unsubstituted $C_{3-10}$cycloalkanediyl group, a substituted or unsubstituted $C_{5-10}$cycloalkenediyl group, or a substituted or unsubstituted phenylene group; each of $Z_1$, $Z_1'$ and $Z_1''$ is a hydrogen atom or a substituted or unsubstituted $C_{1-6}$alkyl group; $Z_2$ is a hydrogen atom, a substituted or unsubstituted $C_{1-6}$alkyl group, a formyl group, a substituted or unsubstituted $C_{1-6}$alkylcarbonyl group, a substituted or unsubstituted benzoyl group, or a substituted or unsubstituted benzyloxycarbonyl group; $Z_1$ and $Z_2$, when taken together with nitrogen atom, may form a substituted or unsubstituted nitrogen-containing $C_{2-10}$heterocyclic group; m is zero or 1; each of $Z_3$ through $Z_{10}$ is a —$CH_2$— group, a

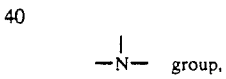

a =CH— group, a (in the above formulas of groups for $Z_3$ through $Z_{12}$, $Y_1$ is a halogen atom, a hydroxyl group, a mercapto group, a nitro group, a cyano group, a substituted or unsubstituted amino group, a substituted or unsubstituted $C_{1-3}$alkyl group, a substituted or unsubstituted $C_{1-3}$alkoxy group, a substituted or unsubstituted $C_{1-3}$alkylthio group, a substituted or unsubstituted $C_{1-3}$alkylcarbonyloxy group, a substituted or unsubstituted $C_{1-3}$alkylcarbonylthio group, a substituted or unsubstituted phenyl group, or a substituted or unsubstituted nitrogen-containing $C_{2-5}$heterocyclic group; $Y_2$ is a substituted or unsubstituted $C_{1-3}$alkyl group; $Y_3$ is a substituted or unsubstituted $C_{1-3}$alkyl group, a substituted or unsubstituted benzyloxy group, or a substituent represented by any of the above general formulas (a) to (c); and $Y_4$ is a substituted or unsubstituted $C_{1-3}$alkyl group)), the total number of atoms of Q other than the hydrogen atoms being 30 or less; in the case where each of $X_3$, $X_4$, $X_6$ and $X_7$ is a hydrogen atom and each of $X_5$ and $X_8$ is a hydroxyl group, Q is a substituent represented by any of the above general formulas (d) to (i).

The chartreusin derivative or a salt thereof having an excellent antitumor activity of this invention is required to have a substituent on the OH group in the 6-position of the aglycone moiety and a substituent on each of the OH groups in the 3'-position and 4'-position of the saccharide moiety and can display no excellent antitumor activity when they lack any one of these substituents. The reason why the term "substituted or unsubstituted ... group" is used herein is that the antitumor activity is substantially determined by said ... group regardless of the substituents. The substituent which said ... group may have may be any group so long as it is pharmacologically acceptable and it can keep the aforesaid chartreusin derivatives chemically stable.

Based on the above findings, as to the term "substituted or unsubstituted" used in the above definitions of $X_1$, $X_2$, Q, R, R', R'', $Z_1$, $Z_1'$, $Z_1''$, $Z_2$, $Y_1$, $Y_2$, $Y_3$ and $Y_4$ in the general formula (I), the substituents which these groups may have are described in detail below.

The substituent on the $C_{1-3}$alkyl group represented by each of $X_1$ and $X_2$ is a halogen atom, a $C_{1-2}$alkoxy group, a $C_{1-2}$alkylthio group, or the like; the substituent on the $C_{1-2}$alkylcarbonyl-$C_{1-2}$alkyl group represented by $X_2$ is a halogen atom, or the like; the substituent on the phenyl group, the phenyl-$C_{1-2}$alkyl group, the furyl group or the thienyl group represented by $X_2$ is a halogen atom, a cyano group, a nitro group, a $C_{1-3}$alkyl group which may be substituted by a halogen atom or the like, a $C_{1-3}$alkoxy group which may be substituted by a halogen atom or the like, a $C_{1-3}$alkylthio group which may be substituted by a halogen atom or the like, a $C_{1-3}$alkylcarbonyl group which may be substituted by a halogen atom or the like, a $C_{1-3}$alkoxycarbonyl group which may be substituted by a halogen atom or the like, or a di-$C_{1-3}$alkylamino group which may be substituted by a halogen atom or the like; and the substituent on the $C_{3-7}$cycloalkylidene which $X_1$ and $X_2$ form when taken together with the adjacent carbon atom is a halogen atom, a $C_{1-2}$alkoxy group, a $C_{1-2}$alkylthio group, or the like.

The combination of $X_1$ and $X_2$ is preferably a combination of $X_1$ being a hydrogen atom with $X_2$ being a substituted or unsubstituted phenyl group, a substituted or unsubstituted furyl group or a substituted or unsubstituted thienyl group; with $X_2$ being a substituted or unsubstituted phenyl group; or with $X_2$ being a phenyl group which may be substituted in the o-position and/or m-position of the benzene nucleus. It is particularly preferred that $X_2$ is a phenyl group which is optionally substituted by a fluorine atom in the m-position of the benzene nucleus.

The combination of $X_3$ through $X_8$ is preferably a combination of each of $X_3$ and $X_6$ being a hydrogen atom, $X_4$ being a hydrogen atom or a methyl group, $X_5$ being a hydroxyl group or an amino group, $X_7$ being a hydrogen atom or an amino group, and $X_8$ being a hydrogen atom or a hydroxyl group; more preferably a combination of each of $X_3$, $X_4$ and $X_6$ being a hydrogen atom, $X_5$ being a hydroxyl group or an amino group, $X_7$ being a hydrogen atom or an amino group, and $X_8$ being a hydrogen atom or a hydroxyl group; most preferably a combination of each of $X_3$, $X_4$, $X_6$ and $X_7$ being a hydrogen atom, and each of $X_5$ and $X_8$ being a hydroxyl group.

The substituent on the $C_{1-11}$alkyl group, the $C_{2-11}$alkenyl group, the $C_{3-11}$alkynyl group, the $C_{3-10}$cycloalkyl group, the $C_{5-10}$cycloalkenyl group, the $C_{1-10}$alkylcarbonyl group or the $C_{1-10}$alkoxycarbonyl group, represented by Q is a halogen atom, a hydroxyl group, a mercapto group, a cyano group, a nitro group, a $C_{1-6}$alkoxy group, a $C_{1-6}$alkylthio group, a $C_{1-6}$alkylsulfinyl group, a $C_{1-6}$alkylsulfonyl group, a $C_{1-6}$alkylcarbonyl group, a $C_{1-6}$alkoxycarbonyl group, a phenoxycarbonyl a $C_{3-7}$cycloalkyl group, a phenyl group, a phenoxy group, a phenylthio group, a phenylsulfinyl group, a phenylsulfonyl group, a benzoyl group, a benzoyloxy group, a benzyloxy group or the like. (The above-mentioned $C_{1-6}$alkoxy group, $C_{1-6}$alkylthio group, $C_{1-6}$alkylsulfinyl group, $C_{1-6}$alkylsulfonyl group, $C_{1-6}$alkylcarbonyl group, $C_{1-6}$alkoxycarbonyl group, phenoxycarbonyl group, $C_{1-6}$alkylcarbonyloxy group, $C_{3-7}$cycloalkyl group, phenyl group, phenoxy group, phenylthio group, phenylsulfinyl group, phenylsulfonyl group, benzoyl group, benzoyloxy group, benzyloxy group or the like may be further substituted. The substituent is a halogen atom, a hydroxyl group, a mercapto group, a $C_{1-3}$alkoxy group, a $C_{1-3}$alkylthio group or the like.)

The substituent on the phenyl group represented by Q is a halogen atom, a hydroxyl group, a mercapto group, a cyano group, a nitro group, a $C_{1-6}$alkylsulfinyl group, a $C_{1-6}$alkylsulfonyl group, a $C_{1-6}$alkyl group, a $C_{1-6}$alkoxy group, a $C_{1-6}$alkylthio group, a $C_{1-6}$alkylcarbonyl group, a $C_{1-6}$alkoxycarbonyl group, a $C_{1-6}$alkylcarbonyloxy group or the like. (The above-mentioned $C_{1-6}$alkylcarbonyl group, $C_{1-6}$alkoxycarbonyl group, a $C_{1-6}$alkylcarbonyloxy group or the like may be further substituted. The substituent is a halogen atom, a hydroxyl group, a mercapto group, a $C_{1-3}$alkoxy group, a $C_{1-3}$alkylthio group or the like.)

In this case, Q is preferably a substituted or unsubstituted $C_{1-11}$alkyl group, a substituted or unsubstituted $C_{2-11}$alkenyl group, a substituted or unsubstituted $C_{3-10}$cycloalkyl group or a substituted or unsubstituted phenyl group, more preferably a substituted or unsubstituted $C_{1-11}$alkyl group, a substituted or unsubstituted $C_{3-10}$cycloalkyl group or a substituted or unsubstituted phenyl group, and most preferably a substituted or unsubstituted $C_{1-11}$alkyl group or a substituted or unsubstituted $C_{3-10}$cycloalkyl group.

In addition, among the substituents represented by the above general formulas (a) to (c), Q is preferably any of the substituents represented by the above general formulas (a) and (b), more preferably the substituent represented by the above general formula (a).

Further, among the substituents represented by the above general formulas (d) to (i), Q is preferably any of the substituents represented by the above general formulas (d), (e) and (f), more preferably the substituents represented by the above general formula (e), most preferably a substituted or unsubstituted furanyl group, a substituted or unsubstituted thienyl group, a substituted or unsubstituted pyrrolyl group, or a substituted or unsubstituted pyrrolidinyl group, or a substituted or unsubstituted isoxazolyl group.

Next, R, R' and R'' in the definition of Q are explained below. The substituent on the $C_{1-11}$alkanedyl group, the $C_{2-11}$alkenendiyl group, the $C_{2-11}$alkynediyl group, the $C_{3-10}$cycloalkanediyl group or the $C_{5-10}$cycloalkenediyl group represented by each of R, R' and R'' is a halogen atom; a hydroxyl group; a mercapto group; a $C_{1-6}$alkoxy group; a $C_{1-6}$alkylthio group; a $C_{1-6}$alkylsulfinyl group; a $C_{1-6}$alkylsulfonyl group; an aminocarbonyl group; a hydroxycarbonyl group; a $C_{1-5}$alkoxycarbonyl group; a phenyl group which is optionally substituted by a halogen atom, a hydroxyl group, a mercapto group, a $C_{1-3}$alkoxy group, a $C_{1-3}$alkylthio group or the like; or a 3-indolyl group which is optionally substituted by a halogen atom or the like. The substituent on the phenylene group represented by each of R, R' and R" is a halogen atom, a hydroxyl group, a mercapto group, a $C_{1-6}$alkoxy group, a $C_{1-6}$alkylthio group, a $C_{1-6}$alkylsulfinyl group, a $C_{1-6}$alkylsulfonyl group, an aminocarbonyl group, a hydroxycarbonyl group, a $C_{1-5}$alkoxycarbonyl group or the like.

R, R' and R" are preferably substituted or unsubstituted $C_{1-11}$alkanediyl groups or $C_{3-10}$cycloalkanediyl groups, more preferably substituted or unsubstituted $C_{1-5}$alkanediyl groups or $C_{3-6}$cycloalkanediyl groups, and most preferably substituted or unsubstituted $C_{1-5}$alkanediyl groups.

Further, $Z_1$, $Z_1'$, $Z_1''$ and $Z_2$ in the definition of Q are explained below. The substituent on the $C_{1-6}$-alkyl group represented by each of $Z_1$, $Z_1'$ and $Z_1''$ and $Z_2$ is a halogen atom, a hydroxyl group, a mercapto group, a $C_{1-3}$alkoxy group, a $C_{1-3}$alkylthio group or the like. The subsituent on the $C_{1-6}$alkylcarbonyl group or the benzoyl group represented by $Z_2$ is a halogen atom, a hydroxyl group, a mercapto group, a $C_{1-3}$alkoxy group, a $C_{1-3}$alkylthio group or the like. The substituent on the benzyloxycarbonyl group represented by $Z_2$ is a halogen atom or the like. The substituent on the nitrogen-containing $C_{2-10}$heterocyclic group which $Z_1$ and $Z_2$ form when taken together with the nitrogen atom is a halogen atom, a hydroxyl group, a mercapto group, a $C_{1-3}$alkyl group, a $C_{1-3}$alkoxy group, a $C_{1-3}$alkylthio group or the like. The term "nitrogen-containing $C_{2-10}$-heterocyclic group which $Z_1$ and $Z_2$ form when taken together with the nitrogen atom" means a heterocyclic group, the ring of which is composed of one nitrogen atom and 2 to 10 carbon atoms, and if necessary, an oxygen atom and/or a sulfur atom, and specific examples thereof include aziridine ($C_2$), pyrrolidine ($C_4$), morpholine ($C_4$), thiomorpholine ($C_4$), piperidine ($C_5$), heptaethleneimine ($C_7$), etc.

Among the above-mentioned atom and groups for $Z_1$, $Z_1'$, and $Z_1''$, each of $Z_1$, $Z_1'$ and $Z_1''$ is preferably a hydrogen atom or a substituted or unsubstituted $C_{1-3}$-alkyl group, and among the above-mentioned groups for $Z_2$, $Z_2$ is preferably a substituted or unsubstituted $C_{1-3}$-alkyl group or a formyl group.

In addition, $Y_1$, $Y_2$, $Y_3$ and $Y_4$ in the definition of Q are explained below. The substituent on the amino group represented by $Y_1$ is a $C_{1-6}$alkyl group which is optionally substituted by a halogen atom, a hydroxyl group, a mercapto group, a $C_{1-3}$alkoxy group, a $C_{1-3}$alkylthio group or the like; a $C_{1-3}$alkylcarbonyl group which is optionally substituted by a halogen atom or the like; or a substituted carbonyl group having as the substituent any of the substituents represented by the above general formulas (a) to (c). The substituent on the nitrogen-containing $C_{2-5}$heterocyclic group represented by $Y_1$ is a halogen atom, a hydroxyl group, a mercapto group, a $C_{1-3}$alkyl group, a $C_{1-3}$alkoxy group, a $C_{1-3}$alkylthio group or the like. The term "nitrogen-containing $C_{2-5}$heterocyclic group represented by $Y_1$" means a heterocyclic group, the ring of which is composed of one or two nitrogen atoms and 2 to 5 carbon atoms, and if necessary, an oxygen atoms and/or a sulfur atom, and specific examples thereof include aziridine ($C_2$), pyrrolidine ($C_4$), morpholine ($C_4$), thiomorpholine ($C_4$), piperidine ($C_5$), piperazine ($C_4$), heptaethyleneimine ($C_7$), etc. The substituent on the $C_{1-3}$alkyl group, the $C_{1-3}$alkoxy group, the $C_{1-3}$alkylthio group, the $C_{1-3}$alkylcarbonyloxy group, the $C_{1-3}$alkylcarbonylthio group or the phenyl group represented by $Y_1$ and the substituent on the $C_{1-3}$alkyl group represented by $Y_2$ are individually a halogen atom; a hydroxyl group; a mercapto group; a cyano group; a $C_{1-3}$alkylcarbonyl group which is optionally substituted by a halogen atom on the like; or an amino group which is optionally substituted by a substituted carbonyl group having as the substituent any of the substituents represented by the above general formulas (a) to (c). The substituent on the $C_{1-3}$alkyl group or the benzyloxy group represented by $Y_3$ and the substituent on the $C_{1-3}$alkyl group represented by $Y_4$ are individually a halogen atom or the like.

Specific examples of the ring moieties of the substituents represented by the above general formulas (d) to (i) are described below.

The ring moiety of the substituent represented by the general formula (d) includes aziridine, oxirane, etc. The ring moiety of the substituent represented by the general formula (3) includes pyrrole, pyrroline, pyrrolidine, 2-oxopyrrolidine, furan, thiophene, pyrazole, isoxazole, isothiazole, isopyrazole, imidazole, oxazole, thiazole, thiazolidine, triazole, oxadiazole, oxathiazole, dioxazole, dioxolan, thiadiazole, tetrazole, thiatriazole, dithiadiazole, etc. The ring moiety of the substituent represented by the general formula (f) includes pyridine, tetrahydropyridine, pyran, α-pyran, thiopyran, dioxane, pyrazine, piperidine, oxazine, morpholine, pyridazine, pyrimidine, thiazine, trioxane, triazine, dioxazine, oxadiazine, thiadiazine, tetrazine, dithiadiazine, oxatriazine, pentazine, etc. The ring moiety of the substituent represented by the general formula (g) includes thienofuran, pyrazorooxazole, imidazothiazole, oxathiolopyrrole, dioxoloimidazole, etc. The ring moiety of the substituent represented by the general formual (h) includes benzofuran, benzothiophene, indole, isoindole, pyrindine, benzodiazine, benzoimidazole, indazole, benzotriazole, benzisoxazole, benzoxazole, benzthiazole, benzoxadiazole, benzofurazane, pyrazolopyridine, triazolopyridine, purine, triazolopiperazine, etc. The ring moiety of the substituent represented by the general formula (i) includes benzopyran, quinoline, isoquinoline, benzopyridazine, benzopyrimidine, benzopyrazine, benzotriazine, benzotetrazine, benzooxazine, benzodioxane, benzodioxine, benzothiazine, benzoxadiazine, benzoxatriazine, pyridopyridine, 4-oxopyridopyridine, pyrazinopyridazine, pyrazinopyrimidine, etc.

The total number of atoms of Q other than the hydrogen atoms is usually 30 or less, preferably 20 or less, more preferably 15 or less.

In the above explanations, the alkyl, alkenyl or alkynyl portion of a radical compressing as a constituent an alkyl group, an alkenyl group, an alkynyl group, an alkanediyl group, an alkenediyl group, an alkynediyl group or a radical therof may be of either a straight chain or a branched chain. Specific examples of, for instance, the alkyl group include methyl, ethyl, propyl, hexyl, undecyl, etc. Specific examples of the cycloalkyl and cycloalkenyl portions of a radical comprising as a constituent a cycloalkyl group, a cycloalkenyl group, a cycloaklanediyl group, a cycloalkenediyl group or a radical thereof include cyclopropyl, cyclopentyl, cyclohexanyl, etc. Specific examples of the halogen atom include fluorine, chorine, bromine, etc.

The salts of the chartreusin derivatives in this invention are phyliologically acceptable organic or inorganic salts, and include, for example, formates, acetates, propionates, butyrates, hydrochlorides, sulfates, phosphates, and quaternary ammonium salts obtained by using halogenated alkyls such as methyl iodide, methyl bromide, methyl chloride, ethyl bromide and the like.

The chartreusin derivatives and salts thereof of this invention include their stereoisomers when $X_1$ and $X_2$ in the saccharide moiety are different. For example, there exist an exo isomer (hereinafter abbreviated as "exo form") in which of the O-substituents $X_1$ and $X_2$ in the 3'-position and 4'-position of the saccharide moiety of the chartreusin derivative and a salt thereof, one which has a larger molecular weight is located outside with respect to the bicyclic ring system composed of a six-membered ring of fucose and a five-membered ring of acetal; and an endo isomer (hereinafter abbreviated as "endo form") in which this O-substituent is located inside the bicyclic ring system. Although both isomers have an excellent antitumor activity, the exo form which displays an antitumor activity in a smaller dose is preferred.

The chartreusin derivative represented by the above general formula (I) of this invention and a salt thereof can be produced by the reation of a compound of the general formula (II):

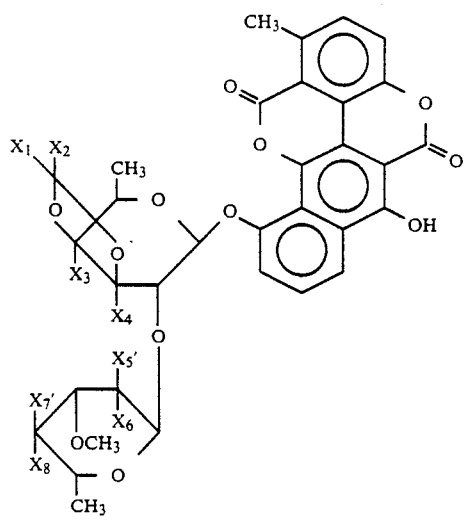

(II)

wherein $X_1$ through $X_4$ have the same meanings as defined above; $X_5'$ is a hydrogen atom, a hydroxyl group, an azide group or a benzyloxycarbonylamino group; $X_6$ is a hydrogen atom or a hydroxyl group; $X_5'$ and $X_6$ may be bonded to the same oxygen atom at the same time; in the case where $X_5'$ is a hydroxyl group, an azido group or a benzyloxycarbonylamino group, $X_6$ is a hydrogen atom; $X_7'$ is a hydrogen atom, an azido group or a benzyloxycarbonylamino group; $X_8$ is a hydrogen atom or a hydroxyl group; in the case where $X_7'$ is an azido group or a benzyloxycarbonylamino group, $X_8$ is a hydrogen atom, with a carboxylic acid derivative of the general formula (III):

HOOC—Q (III)

wherein Q has the same meaning as defined above, and if desired, subjecting the reaction product to reduction and/or acid treatment.

Specifically, the compound of this invention can be produced, for example, by any of the following processes (A) to (J). In the following general synthesis examples processes (A) to (J), $X_1$, $X_2$ and Q in the general formulas (II-1) to (XXIX) have the same meanings as defined above; $X_9$ is chlorine or bromine; TBDMS is a tert-butyldimethylsilyl group; Ms is a methanesulfonyl group; Bzl is a benzyl group; Ac is an acetyl group; CBz is a carbobenzyloxy group; TBAF is tetra-n-butylammonium fluoride; THF is tetrahydrofuran; HMPA is hexamethylphosphorictriamide; and BzB is benzyl bromide.

PROCESS A (DIRECT PROCESS)

First Step

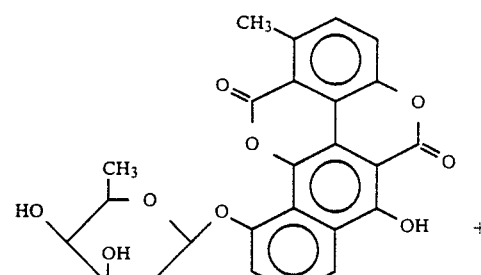

(IV)

+

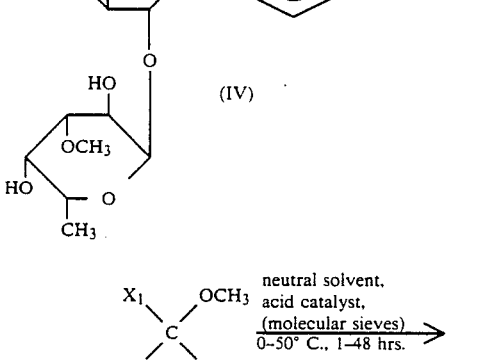

(V-1)

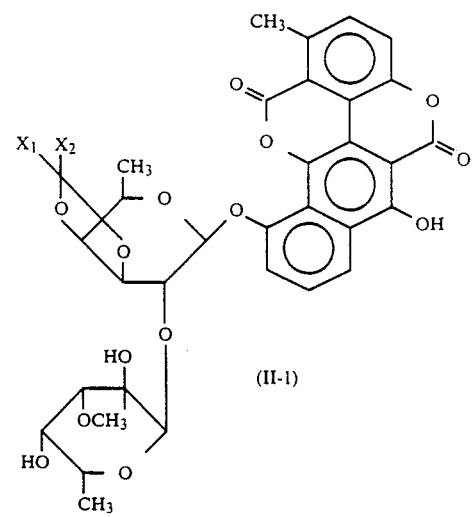

(II-1)

or (IV) + 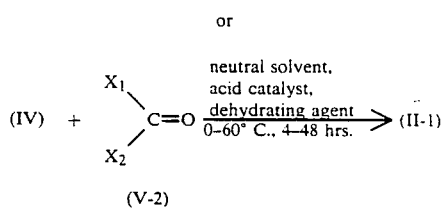

(V-2)

When $X_1$ and $X_2$ are different in the compound (II-1) and separation of the stereoisomers (diastereomers) is necessary, the following separation step is additionably carried out:

Separation Step

Conventional separation:

(II-1) —Column separation→

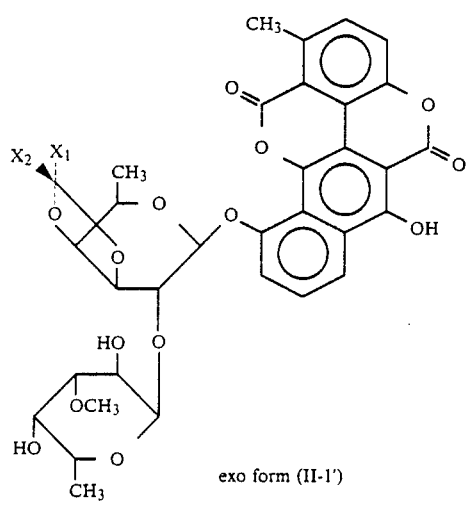

exo form (II-1')

+

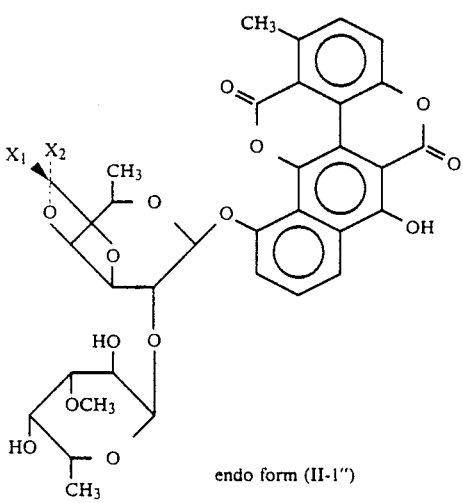

endo form (II-1'')

In this care, the molecular weight of $X_1$ is lower than that of $X_2$.

Separation of the exo isomer from a mixture of the exo and endo forms by chemical conversion-selective solvolysis of the endo isomer.

$$(II\text{-}1) \xrightarrow[\text{0 to 40°C., 1 to 48 hrs.}]{\substack{\text{neutral solvent,} \\ \text{polar neutral solvent (A),} \\ \text{acid catalyst}}} (IV) +$$

$$(II\text{-}1'') \xrightarrow{\text{Column separation}} (II\text{-}1')$$

Second Step (II-1), (II-1') or (II-1'') + HOOC-Q (III)

$$\xrightarrow[\text{10 to 40°C., 1 to 250 hrs.}]{\substack{\text{neutral solvent,} \\ \text{basic solvent in} \\ \text{the presence of a} \\ \text{condensing agent}}}$$

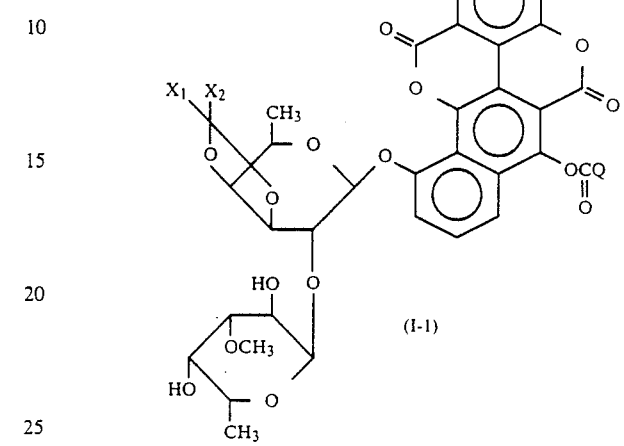

(I-1)

In the above general synthesis example (Process A), when the compound (II-1) has stereoisomers (diastereomers), the ratio between the exo form (II-1') and the endo form (II-1'') can be changes to some extent by selecting the reaction conditions.

For example, in the synthesis of an unsubstituted benzylidene series compound ($X_1$: hydrogen, $X_2$: a phenyl group), the proportion of (II-1') is higher when (V-1) is used as a reagent than when (V-2) is used. When (V-2) is used, the proportion of (II-1'') is improved when the reaction temperature is lowered.

In the step of column separation of (II-1') and (II-1''), the column separation should be conducted several times because the polarities of (II-1') and (II-1'') are similar, but as described in the above example, it is also possible to obtain (II-1') alone with a high purity easily by a single column separation [separation between (II-1') and (IV)] by subjecting only (II-1'') to selective solvolysis under weakly acidic conditions to convert (II-1'') into (IV).

When, a group of compounds in which Q in the general formula (I-1) includes a primary amino group or a secondary amino group, and salts thereof [hereinafter referred to as (I-1-1)] are synthesized, the following reduction step, for example, is additionally carried out:

Reduction Step $$(I\text{-}1\text{-}2) \xrightarrow[\text{0 to 30°C., 0.5 to 5 hrs.}]{\substack{\text{hydrogen (1-3 atmospheres), (organic} \\ \text{or inorganic acid), reducing catalyst,} \\ \text{polar neutral solvents (A) and (B)}}} (I\text{-}1\text{-}1)$$

wherein (I-1-2) refers to a group of compounds in which Q in the general formula (I-1) includes an N-carbobenzyloxy group.

When a salt of compound in which Q in the general formula (I-1) includes a tertiary amino group is synthesized, an acid treatment step with an organic acid, an inorganic acid or an alkyl halide (a quarternary ammonium salt) is additionally carried out.

When a group of compounds in which Q in the general formula (I-1) includes a hydroxyl group (hereinafter referred to as (I-1-3)) are synthesized, the following reduction step, for example, is additionally carried out:

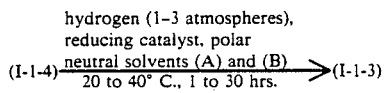

wherein (I-1-4) refers to a group of compounds in which Q in the general formula (I-1) includes a benzyloxy group.

PROCESS B (VIA MONOSILYL FORM)

First Step

The same as the first step [(IV)→(II-1)] of the above Process A.

Second Step

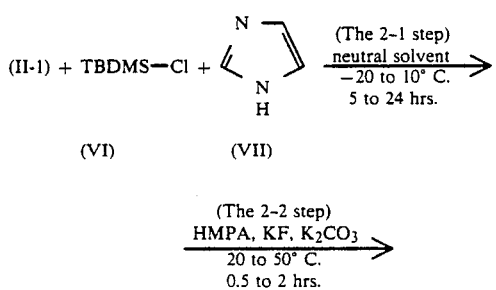

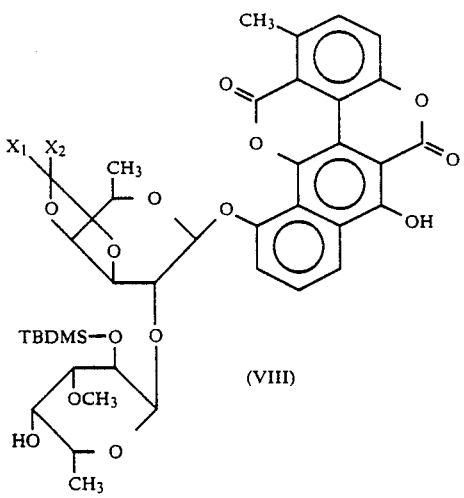

Third Step

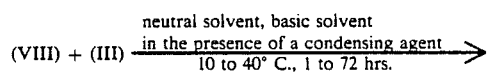

Fourth Step (Removal of the Protecting Group)

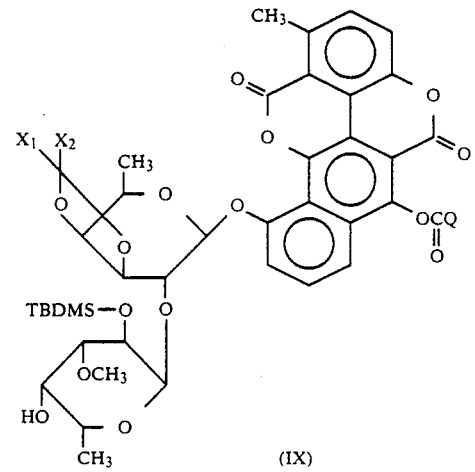

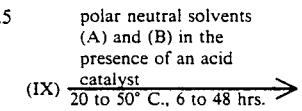

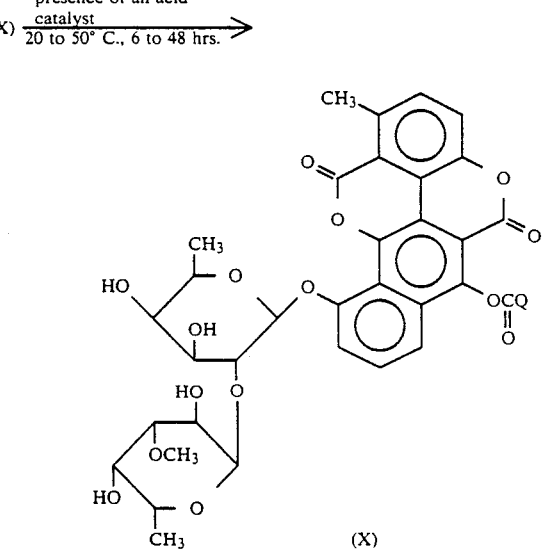

Fifth Step

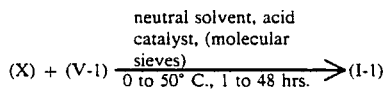

or

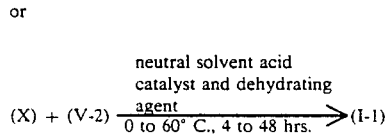

PROCESS C (VIA DISILYL FORM)

First Step

The same as the first step [(IV)→(II-1)] of the above Process A.

Second Step

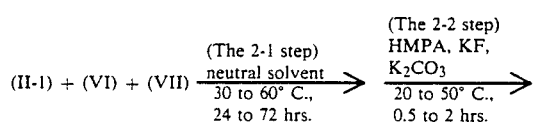

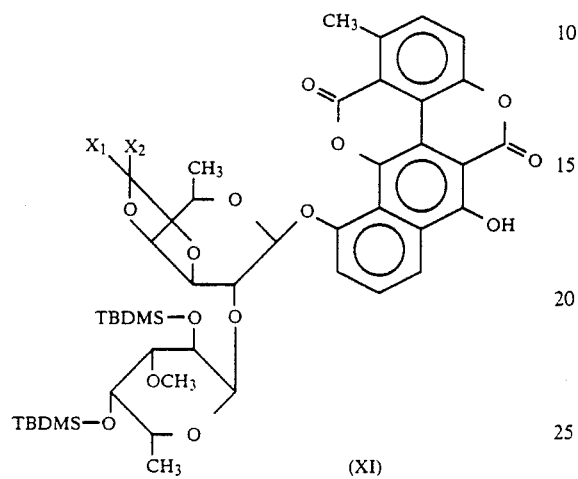

Third Step ((XII) is Synthesized by any of the Following Methods a to d)

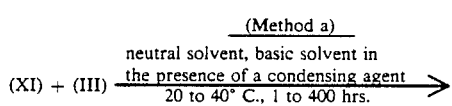

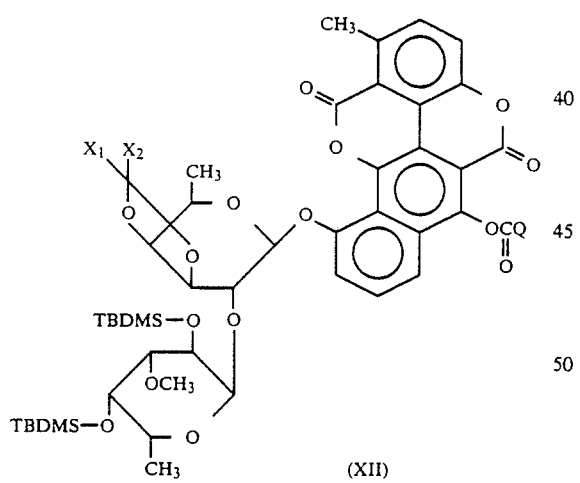

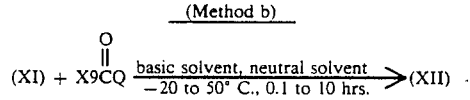

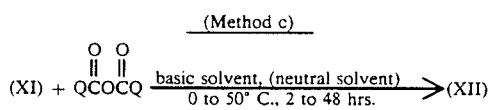

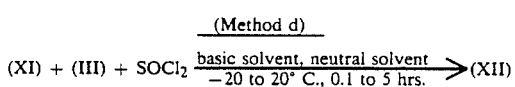

Fourth Step (Removal of the Protecting Group)

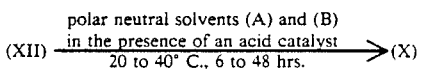

Fifth Step

The same as the fifth step [(X)→(I-1)] of the above Process B.

PROCESS D

First Step

The same as the first step [(IV)→(II-1)] of the above Process A.

Second Step

The same as the second step [(II-1)→(VIII)] of the above Process B.

Third Step (Methanesulfonylation and Removal of the Protecting Group)

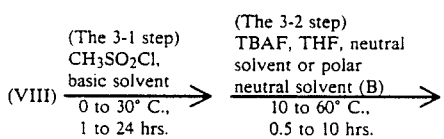

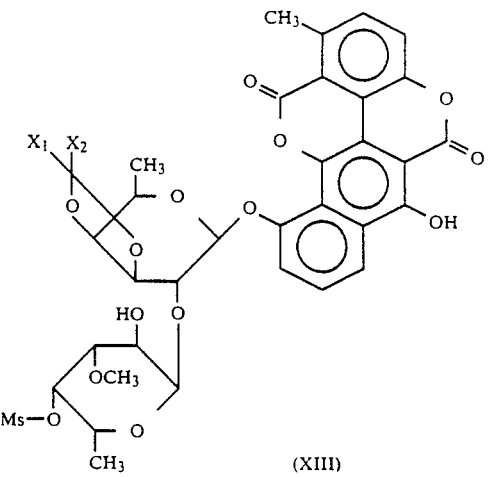

Fourth Step (Conversion into an Azide)

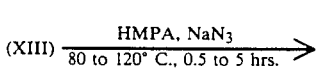

-continued

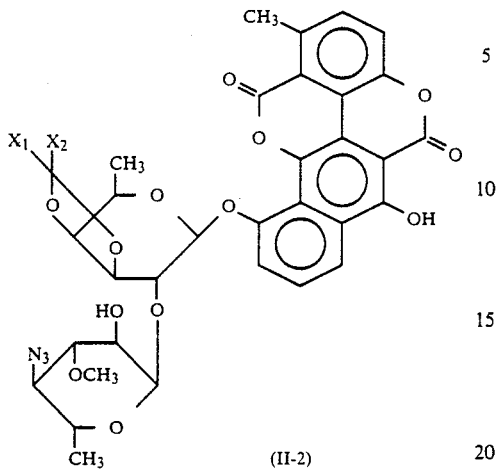

(II-2)

-continued

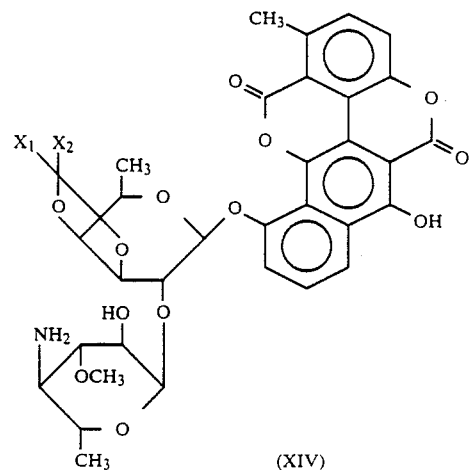

(XIV)

Fifth Step

Sixth Step

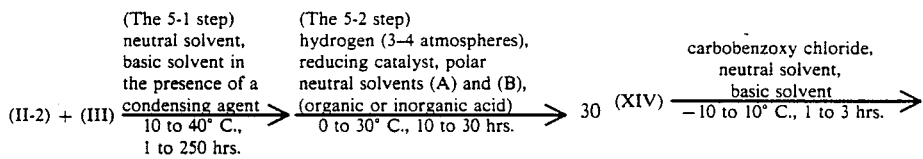

(XIV) $\xrightarrow[-10 \text{ to } 10°\text{ C.}, 1 \text{ to } 3 \text{ hrs.}]{\text{carbobenzoxy chloride, neutral solvent, basic solvent}}$

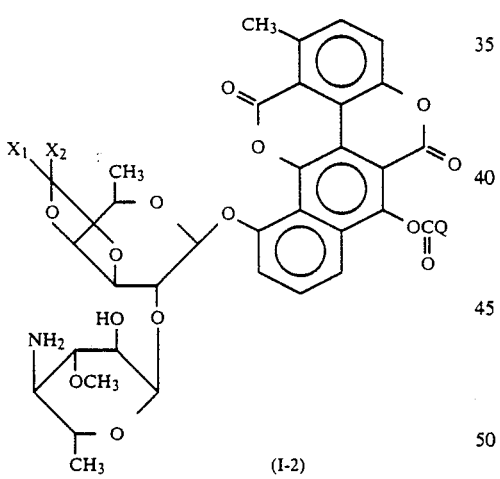

(I-2)

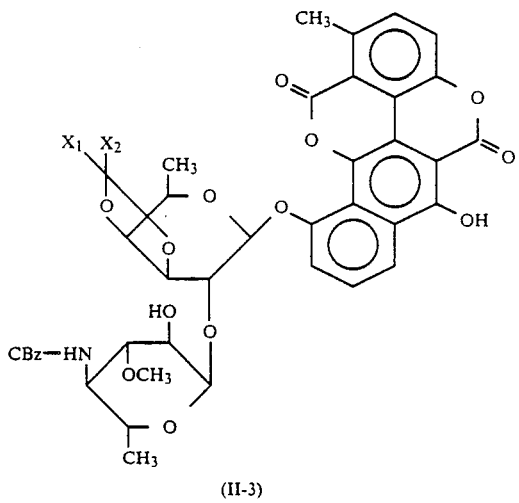

(II-3)

PROCESS E

First to Fourth Steps

The same as the first to fourth steps [(IV)→(II-2)] of the above Process D.

Fifth Step (Reduction of the Azide)

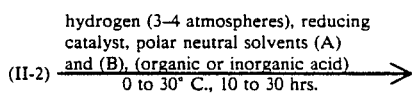

Seventh Step (The 7-1 step)
(II-3) + (III) $\xrightarrow[10 \text{ to } 40° \text{ C.}, 1 \text{ to } 250 \text{ hrs.}]{\text{neutral solvent, basic solvent in the presence of a condensing agent}}$

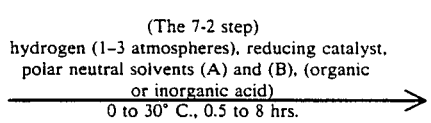

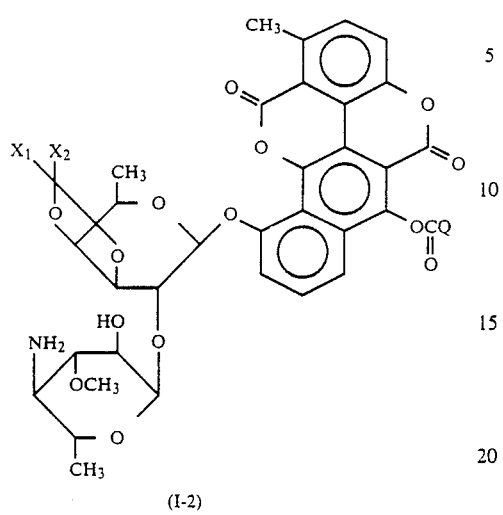

(I-2)

PROCESS F

First and Second Steps

The same as the first and second steps [(IV)→(XI)] of the above Process C.

Third Step (Removal of the Protecting Group)

$$(XI) \xrightarrow[\text{20 to 50° C., 1 to 6 hours}]{\text{polar neutral solvents (A) and (B) in the presence of an acid catalyst}}$$

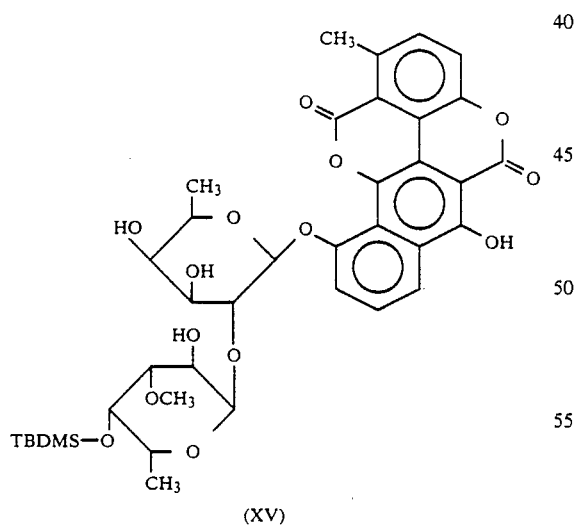

(XV)

Fourth Step $$(XV) + (V-1) \xrightarrow[\text{0 to 50° C., 1 to 48 hrs.}]{\text{neutral sovent, acid catalyst, (molecular sieves)}}$$

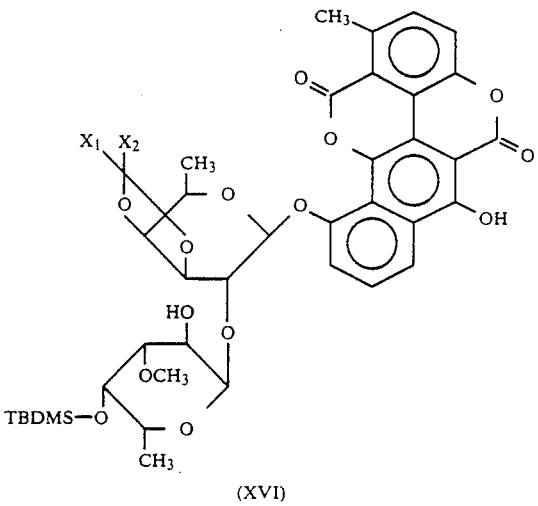

(XVI)

or $$(XV) + (V-2) \xrightarrow[\text{0 to 60° C., 4 to 48 hrs.}]{\text{neutral sovent, acid catalyst, dehydrating agent}} (XVI)$$

Fifth Step (Conversion into a Benzyl Ether Derivative)

$$(XVI) \xrightarrow[\text{10 to 50° C., 0.5 to 5 hours}]{\text{BzB, TBAF, THF, neutral solvent or polar neutral solvent (B)}}$$

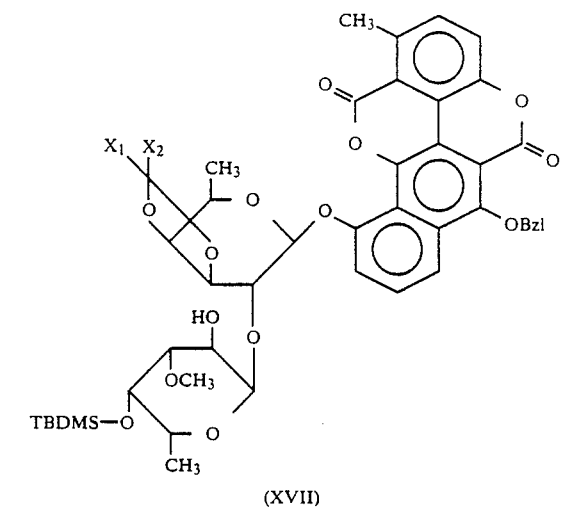

(XVII)

Sixth Step (Oxidation)

$$(XVII) \xrightarrow[\substack{\text{methylene chloride} \\ \text{room temperature,} \\ \text{0.5 to 2 hrs.}}]{\substack{\text{(Oxidation with chromic acid)} \\ \text{chromic anhydride, pyridine}}}$$

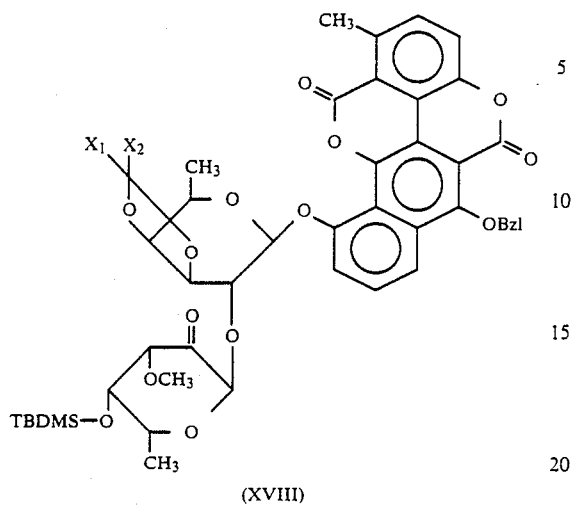
(XVIII)
or
(XVII) —Oxidation with DMSO→ (XVIII)
Seventh Step (Removal of the Protecting Group)
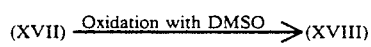
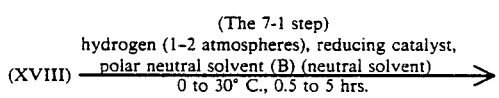
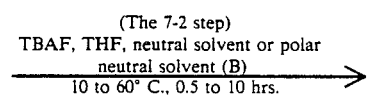
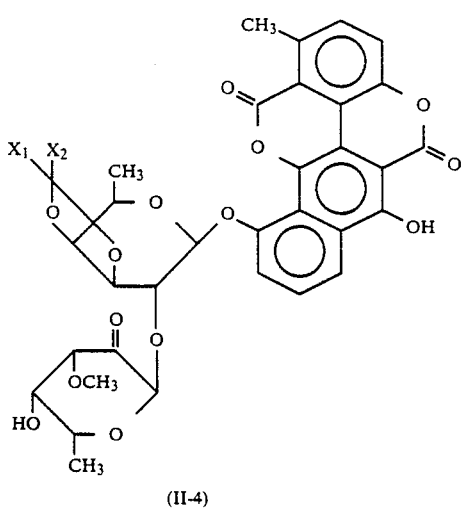
(II-4)
Eighth Step
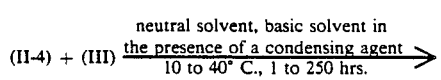
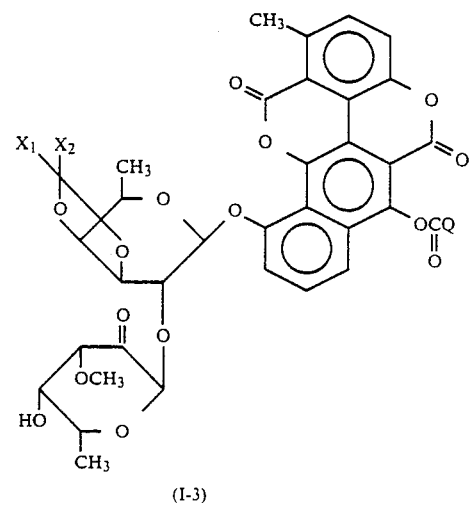
(I-3)
PROCESS G
First to Sixth Steps
The same as the first to sixth steps [(IV)→(XVIII)] of the above Process F.
Seventh Step (Reduction)
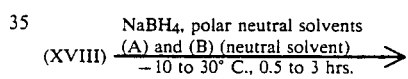
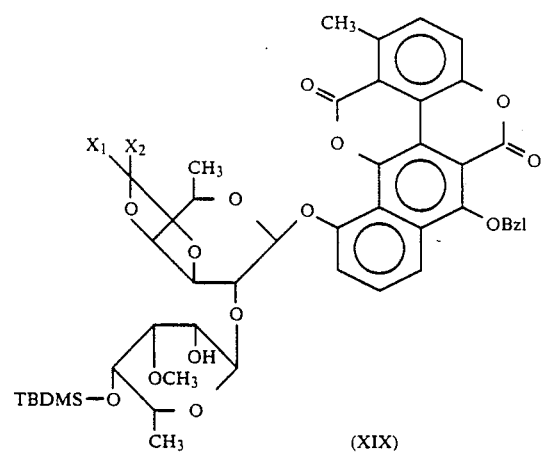
(XIX)
Eighth Step (Removal of the Protecting Group)
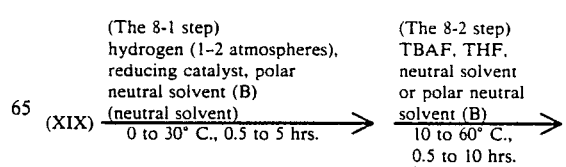

-continued

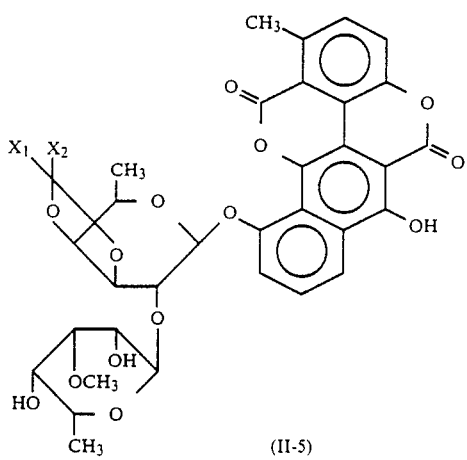

(II-5)

Ninth Step (II-5) + (III) $\xrightarrow[\text{10 to 40° C., 1 to 250 hrs.}]{\text{neutral solvent, basic solvent in the presence of a condensing agent}}$

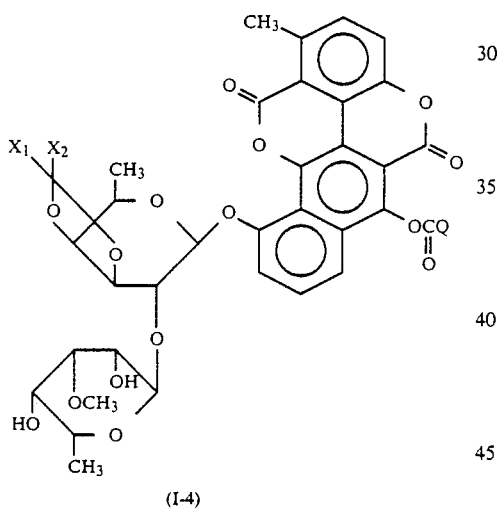

(I-4)

PROCESS H

First Step

The same as the first step [(IV)→(II-1)] of the above process A.

Second Step (Conversion into a Benzyl Ether Derivative and Acetylation)

(II-1) $\xrightarrow[\text{10 to 50° C., 0.5 to 5 hrs.}]{\substack{\text{(The 2-1 step)}\\ \text{BzB, TBAF, THF, neutral solvent}\\ \text{or polar neutral solvent (B)}}}$ $\xrightarrow[\text{0 to 50° C., 2 to 24 hrs.}]{\substack{\text{(The 2-2 step)}\\ \text{acetic anhydride, basic solvent}\\ \text{(neutral solvent)}}}$ -continued

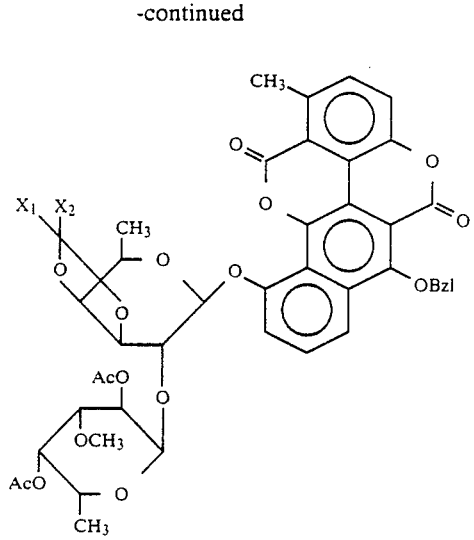

(XX)

Third Step (Removal of the Protecting Group)

(XX) $\xrightarrow[\text{20 to 50° C., 1 to 6 hours}]{\substack{\text{polar neutral solvents (A) and (B)}\\ \text{in the presence of an acid catalyst}}}$

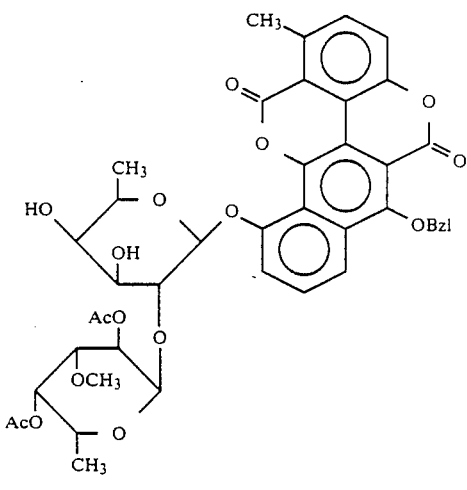

(XXI)

Fourth Step (Silylation)

(XXI) + (VI) + (VII) $\xrightarrow[\text{0 to 50° C., 5 to 24 hrs.}]{\text{neutral solvent}}$ -continued

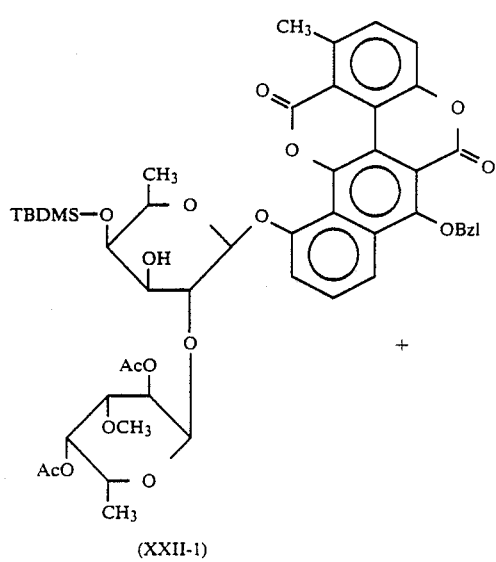

(XXII-1)

+

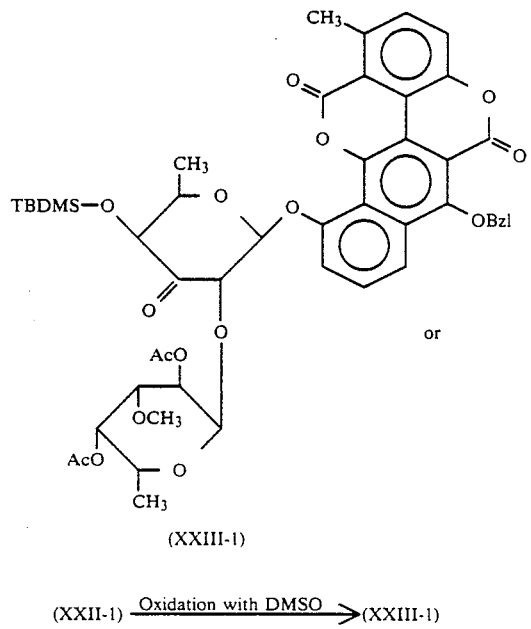

(XXIII-1)

(XXII-1) —Oxidation with DMSO→ (XXIII-1)

Sixth Step (Methylation, De-silylation, and Conversion to an Acetal)

(XXIII-1)

(The 6-1 step)
methyllithium, polar neutral
solvent (B) (neutral solvent)
$-100$ to $-50°$ C., 0.1 to 1 hr.
→

(The 6-2 step)
TBAF, THF, neutral solvent or polar
neutral solvent (B)
10 to 50° C., 0.5 to 24 hrs.
→

(The 6-3 step)
(V-1), neutral solvent, acid catalyst
(molecular sieves)
0 to 50° C., 1 to 48 hrs.
→

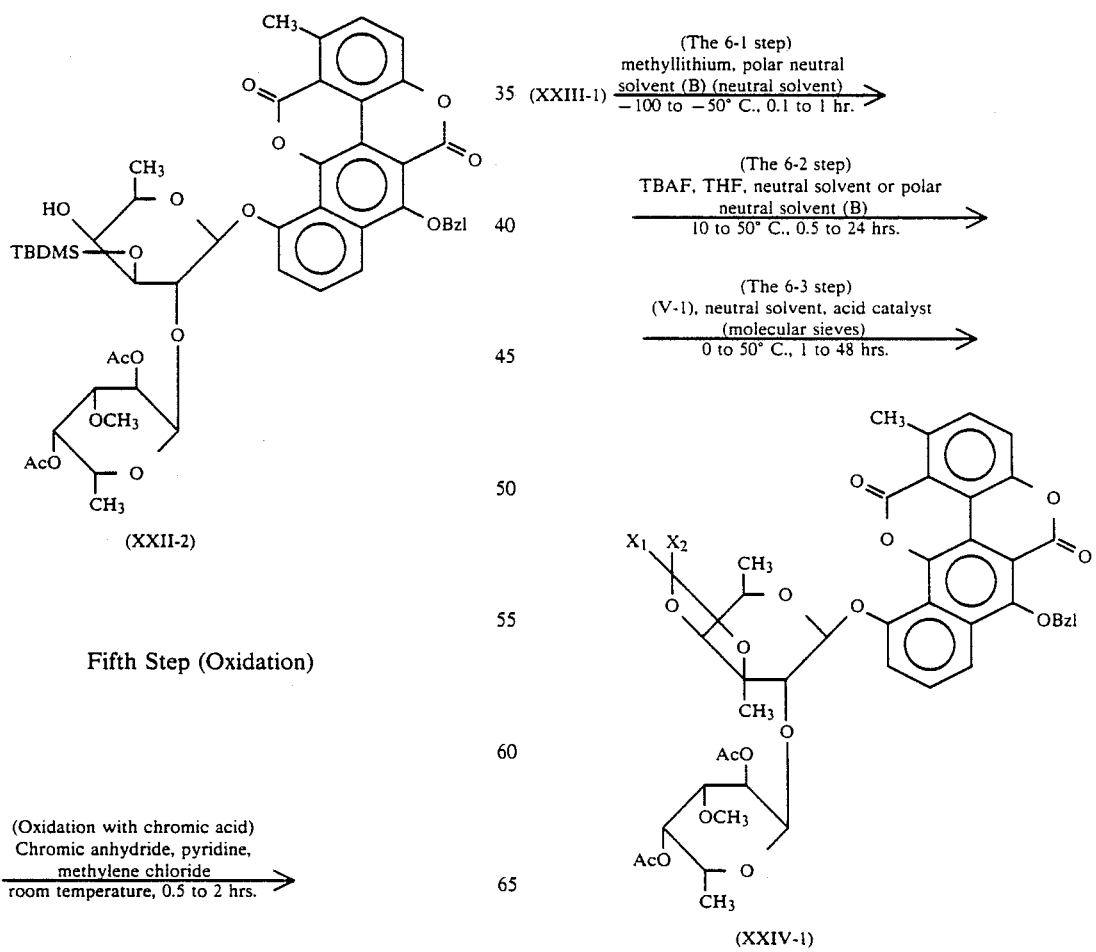

(XXII-2)

Fifth Step (Oxidation)

(XXII-1) —
(Oxidation with chromic acid)
Chromic anhydride, pyridine,
methylene chloride
room temperature, 0.5 to 2 hrs.
→

(XXIV-1)

Seventh Step (Removal of the Protecting Group)

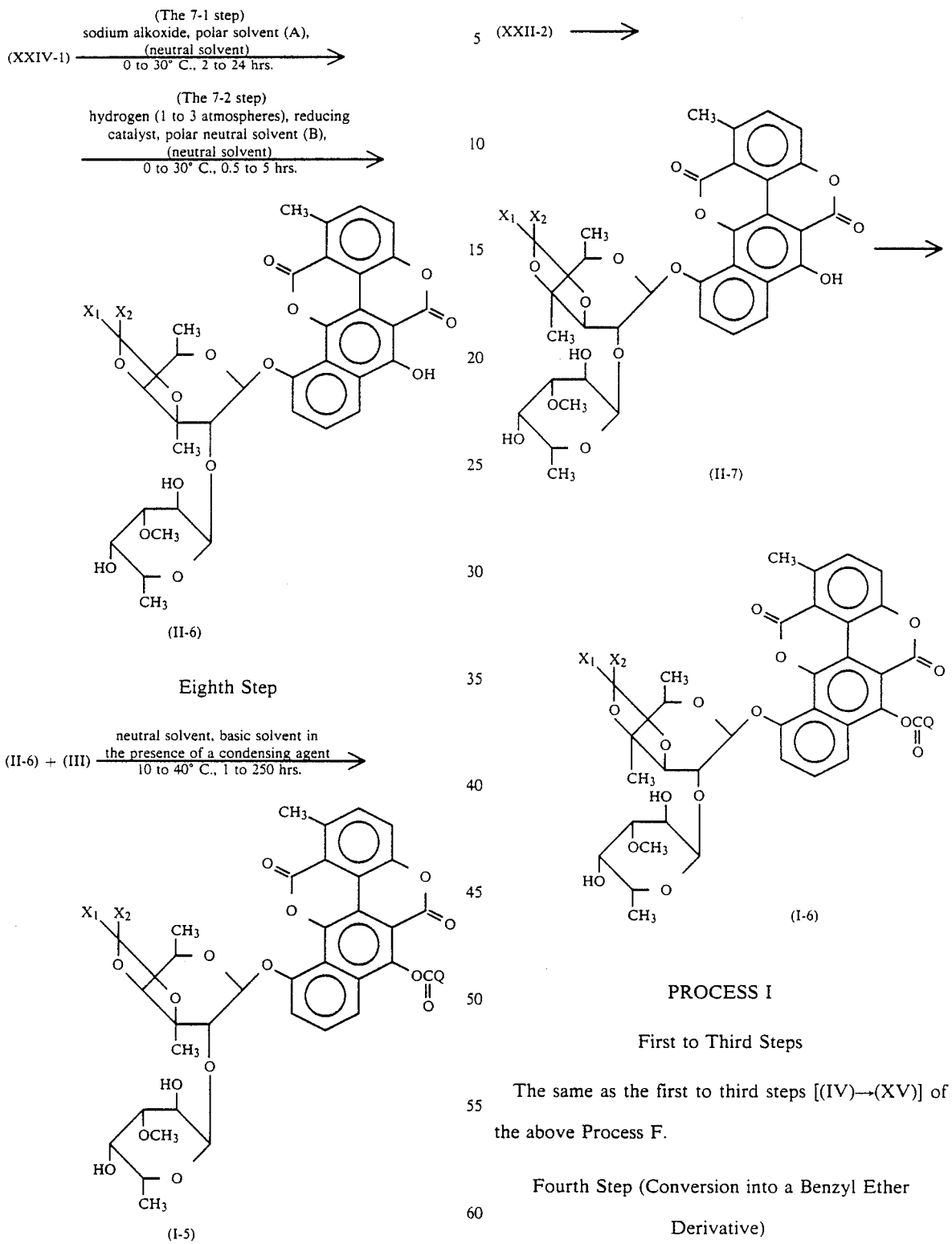

In the above Process H, a compound of this invention (I-6) having a methyl group in the 4'-position can be synthesized via the intermediate (II-7) shown below by using the compound (XXII-2) obtained in the fourth step and carrying out the fifth to eighth steps in the same manner as described above.

PROCESS I

First to Third Steps

The same as the first to third steps [(IV)→(XV)] of the above Process F.

Fourth Step (Conversion into a Benzyl Ether Derivative)

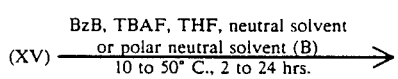

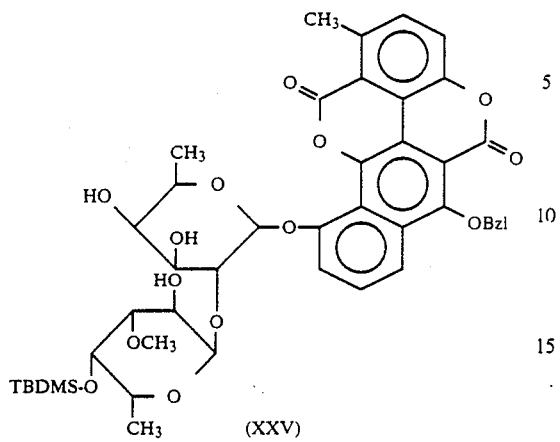

(XXV)

Fifth Step (Silylation)

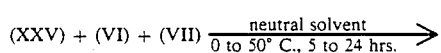

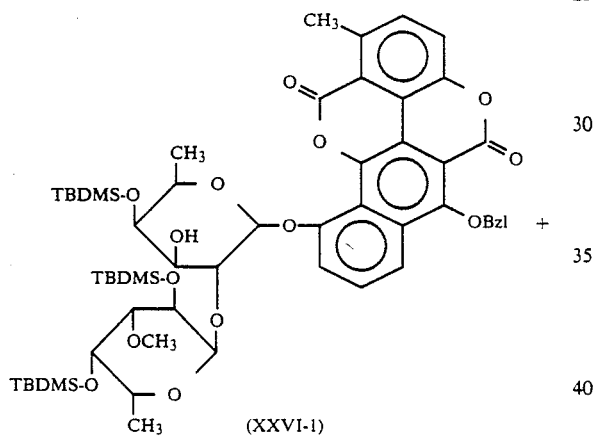

(XXVI-1)

+

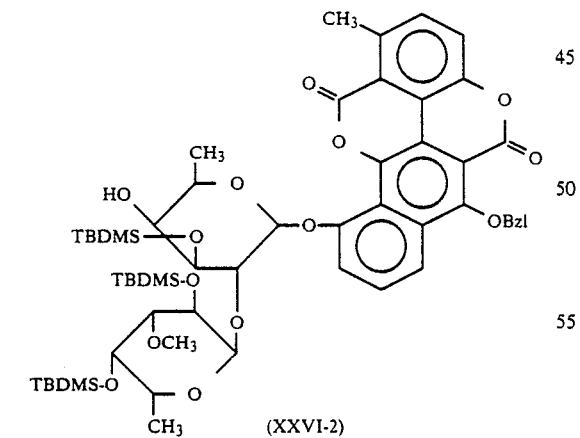

(XXVI-2)

Sixth Step (Oxidation)

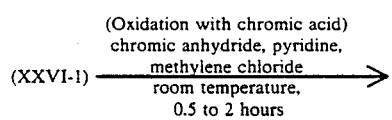

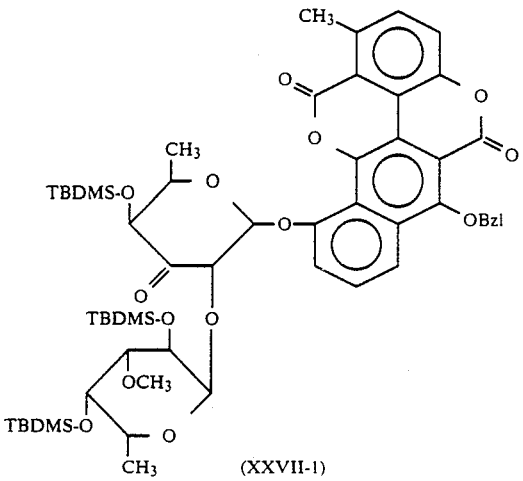

(XXVII-1)

or

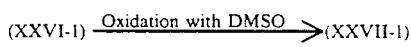

Seventh Step (Methylation, De-silylation, Conversion into an Acetal, and Removal of the Protecting Group)

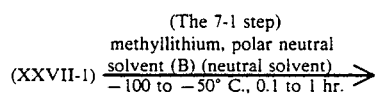

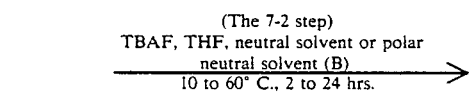

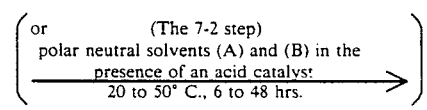

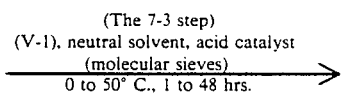

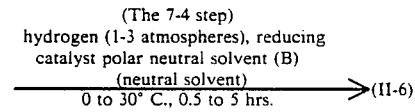

Eigth Step

The same as the eighth step [(II-6)→(I-5)] of the above Process H.

In the above Process (I), a compound of this invention (I-6) having a methyl group in the 4'-position can be synthesized via the intermediate (II-7) by using the compound (XXVI-2) obtained in the fifth step and carrying out the fifth to eigth steps in the same manner as described above.

PROCESS J (I-7) shown below can be synthesized in the following manner by using the following known substance (XXVIII) [U.S. Pat. No. 4,518,589] as a starting material.

First Step (Carbobenzyloxylation)

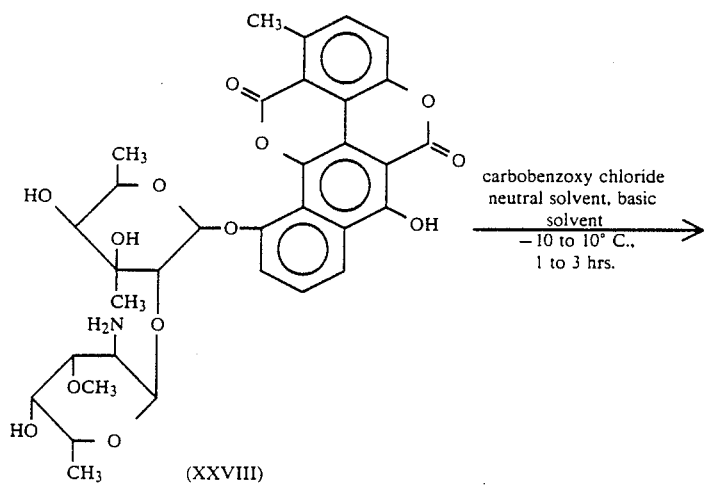

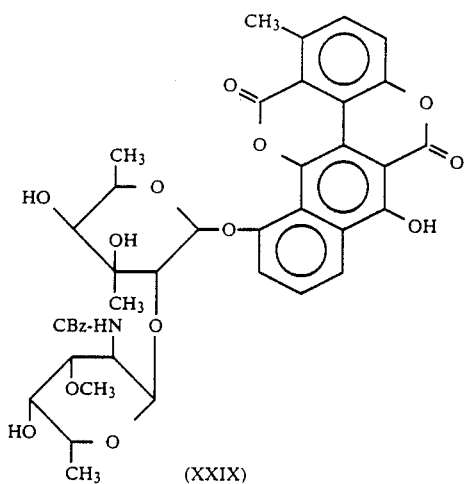

Second Step

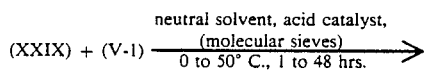

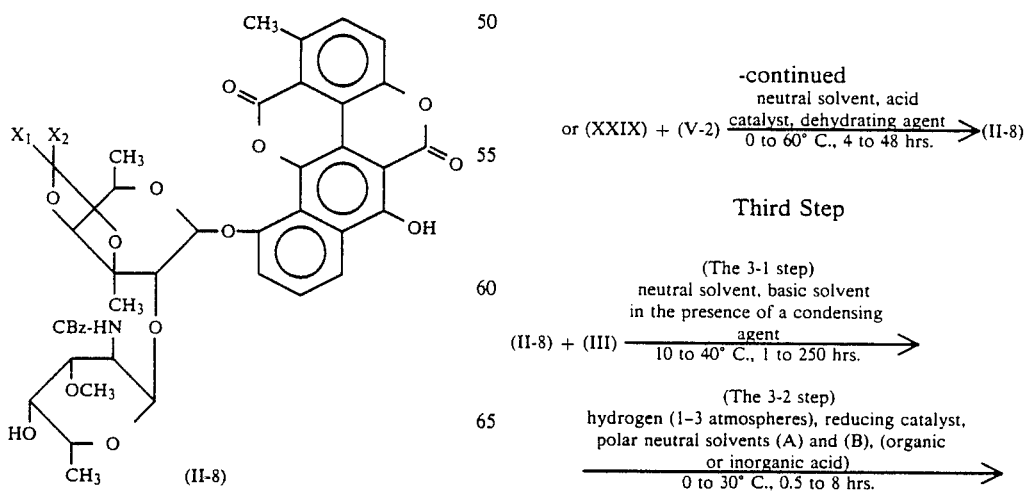

-continued $$\text{or (XXIX)} + \text{(V-2)} \xrightarrow[\text{0 to 60° C., 4 to 48 hrs.}]{\text{neutral solvent, acid catalyst, dehydrating agent}} \text{(II-8)}$$

Third Step (The 3-1 step)

$$\text{(II-8)} + \text{(III)} \xrightarrow[\text{10 to 40° C., 1 to 250 hrs.}]{\substack{\text{neutral solvent, basic solvent} \\ \text{in the presence of a condensing} \\ \text{agent}}}$$

(The 3-2 step)

$$\xrightarrow[\text{0 to 30° C., 0.5 to 8 hrs.}]{\substack{\text{hydrogen (1-3 atmospheres), reducing catalyst,} \\ \text{polar neutral solvents (A) and (B), (organic} \\ \text{or inorganic acid)}}}$$

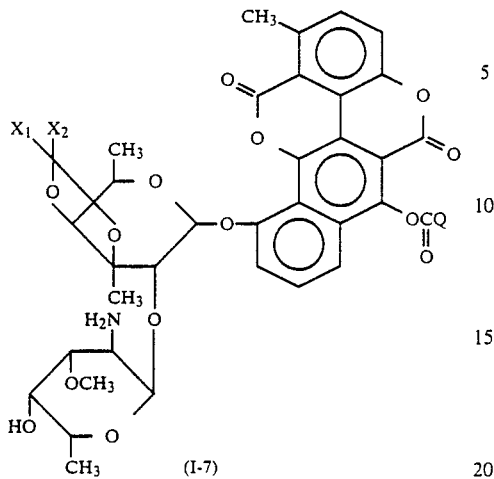

(I-7)

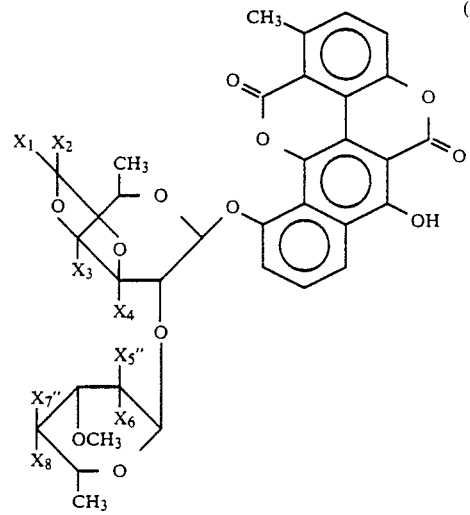

(XXX)

When separation of the stereoisomers (diastereomers) is necessary in the compounds (I-1) to (I-7) in the above Processes (B) to (J), the separation step in the first step of the above Process A is additionally carried out. If necessary, the reduction step in the second step of said Process A is also applied.

Compounds of the general formula (I) other than those synthesized by the above Processes (A) to (J) can be synthesized by property employing processes according to these Processes.

In the above Processes (A) to (J), the neutral solvent includes, for example, chloroform, benzene, toluene, ethyl acetate, dimethylformamide, etc. The polar neutral solvent (A) includes, for example, alcohols, water, etc. The polar neutral solvent (B) includes, for example, tetrahydrofuran, dioxane, dimethoxyethane, etc. The basic solvent includes, for example, pyridine, etc. The acid catalyst includes, for example, sulfonic acids such as p-toluenesulfonic acid and the like; mineral acids such as hydrochloric acid and the like; Lewis acids such as zinc chloride and the like; etc. The dehydrating agent includes, for example, anhydrous copper sulfate, sodium sulfate, molecular sieves, etc. The condensing agent includes, for example, carbodiimides such as dicyclohexylcarbodiimide and the like, etc. The reducing catalyst includes palladium-carbon, etc. The organic acid and the inorganic acid are those which form the above-mentioned physiologically acceptable organic or inorganic salts, and include, for example, formic acid, acetic acid, propionic acid, butyric acid, hydrochloric acid, sulfuric acid, phosphoric acid, etc. When a quaternary ammonium salt of the chartreusin derivative of this invention is prepared, there is used a alkyl halide such as methyl iodide, methyl bromide, methyl chloride, ethyl bromide or the like.

Among the intermediates of the compounds of this invention which can be produced by the above Processes (A) to (J), the compounds represented by the following general formula (XXX) are novel and include the compounds represented by the above general formulas (II-2), (II-3), (II-4), (II-5), (II-6), (II-7), (II-8) and (XIV):

wherein $X_1$, $X_2$, $X_3$, $X_4$, $X_6$ and $X_8$ have the same meanings as defined above; $X_5''$ is a hydrogen atom, a hydroxyl group, an amino group, an azido group or a benzyloxycarbonylamino group; $X_5''$ and $X_6$ may be bonded to the same oxygen at the same time; in the case where $X_5''$ is a hydroxyl group, an amino group, an azido group or a benzyloxycarbonylamino group, $X_6$ is a hydrogen atom; $X_7''$ is a hydrogen atom, an amino group, an azido group or a benzyloxycarbonylamino group; in the case where $X_7''$ is an amino group, azido group or a benzyloxycarbonylamino group, $X_8$ is a hydrogen atom; with the proviso that this formuala does not include the case where each of $X_3$, $X_4$, $X_6$ and $X_7''$ is a hydrogen atom and each of $X_5''$ and $X_8$ is a hydroxyl group.

Furthermore, specific synthesis examples of the intermediates (II-1), (II-1') and (II-1'') are explained below, from which intermediates the compound of this invention is synthesized by Process A (direct process).

SYNTHESIS EXAMPLE 1

Synthesis of the exo form of 3',4'-O-benzylidene-chartreusin (intermediate No. 501)

In 500 ml of anhydrous chloroform was dissolved 20 g of chartreusin, followed by adding thereto 23.8 g of benzaldehyde dimethylacetal, 2 g of p-toluenesulfonic acid and 100 g of Molecular Sieves 5A 1/16, and the resulting mixture was subjected to reaction with stirring at room temperature for 1 hour.

After completion of the reaction, 6 ml of pyridine was added and the resulting mixture was filtered through Celite, after which the filtrate was concentrated to a volume of about 250 ml, and the resulting solution was purified by a silica gel column chromatography to obtain crystals of a mixture of the exo form and the endo form of 3',4'-O-benzylidene-chartreusin.

Subsequently, the aforesaid crystals were dissolved in 200 ml of chloroform, followed by adding thereto 25 ml of a 0.01N hydrochloric acid-methanol solution prepared from concentrated hydrochloric acid and methanol, and the resulting mixture was subjected to reaction with stirring at room temperature for 18 hours.

After completion of the reaction, several milliliters of pyridin was added, and the resulting mixture was filtered, after which the filtrate was concentrated under reduced pressure to obtain a mixture of chartreusin and the exo form of 3',4'-O-benzylidene-chartreusin. Subsequently, this mixture was subjected to a silica gel column chromatography to obtain crystals of the desired compound. Said crystals were recrystallized from a mixture of chloroform and ethanol to obtain 8.6 g of crystals of the exo form.

SYNTHESIS EXAMPLE 2

Synthesis of the exo form and the endo form of 3',4'-O-benzylidene-chartreusin (intermediates Nos. 501 and 502)

In 300 ml of anhydrous chloroform was dissolved 10.0 g of chartreusin, followed by adding thereto 30 ml of benzaldehyde, 1 g of p-toluenesulfonic acid and 50 g of Molecular Sieves 4A 1/16, and the resulting mixture was subjected to reaction with stirring at room temperature for 20 hours.

After completion of the reaction, the reaction mixture was filtered through Celite and the filtrate was concentrated to a volume of about 150 ml, after which the resulting solution was separated by several repetitions of a silica gel column chromatography to obtain crystals of a mixture of the exo form and the endo form of 3',4'-O-benzylidene-chartreusin. The crystals of each isomer were recrystallized from a mixture of chloroform and ethanol, whereby 2.7 g of crystals of the exo form and 4.8 g of crystals of the endo form were obtained.

SYNTHESIS EXAMPLE 3

Synthesis of 3',4'-O-(o-fluorobenzylidene)-chartreusin (a mixture of the exo form and the endo form at a ratio of 1:6, intermediate No. 503)

In 63 ml of anhydrous chloroform was dissolved 2.0 g of chartreusin, followed by adding thereto 3.3 ml of o-fluorobenzaldehyde, 200 mg of p-toluenesulfonic acid and 6 g of Molecular Sieves 4A 1/16, and the resulting mixture was subjected to reaction with stirring at 40° to 50° C. for 24 hours.

After completion of the reaction, the reaction mixture was filtered through Celite, and the filtrate was concentrated, after which the concentrate was purified by several repetitions of a silica gel column chromatography to obtain crystals. The crystals were recrystallized from a mixture of chloroform and ethanol to obtain 630 mg of the desired compound (a mixture of the exo form and the endo form at a ratio of 1:6).

SYNTHESIS EXAMPLE 4

Synthesis of the exo form and the endo form of 3',4'-O-(m-fluorobenzylidene)-chartreusin (intermediates Nos. 504 and 505)

In 250 ml of anhydrous chloroform was dissolved 5.0 g of chartreusin, followed by adding thereto 6.7 g of m-fluorobenzaldehyde dimethylacetal, 1.4 g of p-toluenesulfonic acid and 25 g of Molecular Sieves 5A 1/16, and the resulting mixture was subjected to reaction with stirring at 40° to 45° C. for 5 hours.

After completion of the reaction, 3.0 ml of pyridine was added and the resulting mixture was filtered through Celite, after which the filtrate was concentrated and the resulting crude crystals were separated by several repetitions of a silica gel column chromatography to obtain crystals of the exo form and the endo form of 3',4'-O-(m-fluorobenzylidene)-chartreusin. The crystals of each isomer was recrystallized from a mixture of chloroform and ethanol, whereby 503 mg of crystals of the exo form and 480 mg of crystals of the endo form were obtained.

SYNTHESIS EXAMPLE 5

Synthesis of the endo form of 3',4'-O-(m-trifluoromethylbenzylidene)-chartreusin (intermediate No. 506)

In 30 ml of anhydrous chloroform was dissolved 1.0 g of chartreusin, followed by adding thereto 2.1 ml of m-trifluoromethylbenzaldehyde, 100 mg of p-toluenesulfonic acid and 3 g of Molecular Sieves 4A 1/16, and the resulting mixture was subjected to reaction with stirring at 20° to 25° C. for 20 hours.

After completion of the reaction, the reaction mixture was filtered through Celite and the filtrate was concentrated, after which the concentrate was subjected to several repetitions of a silica gel column chromatography to obtain crystals. The crystals were recrystallized from a mixture of chloroform and ethanol to obtain 580 mg of crystals of the desired compound.

SYNTHESIS EXAMPLE 6

Synthesis of 3',4'-O-(2-furylmethylene)-chartreusin (a mixture of the exo form and the endo form at a ratio of 1:1, intermediate No. 507)

In 50 ml of anhydrous chloroform was dissolved 1.8 g of chartreusin, followed by adding thereto 5.2 ml of furfural, 200 mg of p-toluenesulfonic acid and 5 g of Molecular Sieves 4A 1/16, and the reaction was carried out with stirring at 20° to 25° C. for 24 hours.

After completion of the reaction, the reaction mixture was filtered through Celite and the filtrate was concentrated, after which the concentrate was subjected to several repetitions of a silica gel column chromatography to obtain crystals. The crystals were recrystallized from a mixture of chloroform, ethanol and ether to obtain 498 mg of the desired compound (a mixture of the exo form and the endo form at a ratio of 1:1).

Intermediate Nos. 508 to 526 were synthesized according to Synthesis Examples 1 to 6 above. The structures and melting points of intermediates Nos. 501 to 526 are tabulated in Table 1, and NMR data of typical intermediates of them are shown in Table 2.

TABLE 1

| Intermediate No. | Structure ($X_1$ = hydrogen) (Note 1) $X_2$ | Isomer (Note 2) | Melting point (°C.) |
| --- | --- | --- | --- |
| 501 | Phenyl | Exo form | 165.0–200.0 |
| 502 |  | Endo form | 262.0–266.5 |
| 503 | o-Fluorophenyl | Mixture (1:6) | 258.0–269.0 |
| 504 | m-Fluorophenyl | Exo form | 159.0–165.0 |
| 505 |  | Endo form | 252.0–265.0 |
| 506 | n-Trifluoromethylphenyl | Endo form | 226.0–232.0 |
| 507 | 2-Furyl | Mixture (1:1) | 180.0–192.0 |
| 508 | p-Fluorophenyl | Exo form | 155.0–167.0 |
| 509 |  | Endo form | 235.0–245.0 |
| 510 | o-Chlorophenyl | Endo form | 225.0–234.5 |
| 511 | m-Chlorophenyl | Exo form | 158.0–163.0 |
| 512 |  | Endo form | 243.0–255.0 |
| 513 | p-Chlorophenyl | Exo form | 258.5–268.0 |
| 514 |  | Endo form | 213.5–222.0 |
| 515 | m-Bromophenyl | Endo form | 255.0–263.0 |
| 516 | p-Bromophenyl | Exo form | 275.0–282.0 |
| 517 |  | Endo form | 185.0–189.0 |
| 518 | 2,4-Dichlorophenyl | Endo form | 190.0–200.0 |
| 519 | o-Methylphenyl | Exo form | 192.0–198.0 |
| 520 |  | Endo form | 238.0–243.0 |

TABLE 1-continued

| Intermediate No. | Structure ($X_1$ = hydrogen) (Note 1) $X_2$ | Isomer (Note 2) | Melting point (°C.) |
|---|---|---|---|
| 521 | p-Methoxyphenyl | Exo form | 283.0–295.0 |
| 522 | m-Nitrophenyl | Endo form | 227.0–235.0 |
| 523 | 2-Phenylethyl | Exo form | 137.0–145.0 |
| 524 | 3-Thienyl | Exo form | 236.0–242.0 |
| 525 |  | Endo form | 260.0–272.0 |
| 526 | Pentafluorophenyl | — | oily substance |

Note 1: $X_1$ and $X_2$ represent substituents in the intermediates II-1, II-1' or II-1".
Note 2: In the mixtures, the ratio is that of exo form to endo form.

TABLE 2

| Intermediate No. | NMR Assignment (60 MHz, δ value, in CDCl$_3$) | | | | | | | | | |
|---|---|---|---|---|---|---|---|---|---|---|
|  | A | B | C | D | E | F | G | H* | I | Other (or remarks) |
| 501 | 1.30 | 1.48 | 2.83 | 3.40 | 5.27 | 5.89 | 6.32 | 7.17–8.23 (10H) | 11.70 |  |
| 502 | 1.10 | 1.48 | 2.81 | 3.40 | 5.30 | 5.77 | 5.98 | 7.22–8.23 (10H) | 11.67 |  |
| 504 | 1.33 | 1.49 | 2.84 | 3.43 | 5.31 | 5.91 | 6.33 | 7.00–8.30 (9H) | 11.65 |  |
| 505 | 1.12 | 1.48 | 2.79 | 3.41 | 5.37 | 5.76 | 5.96 | 7.00–8.29 (9H) | 11.62 |  |
| 506 | 1.11 | 1.46 | 2.74 | 3.36 | 5.28 | 5.67 | 5.93 | 7.08–8.18 (9H) | 11.68 |  |
| 508 | 1.27 | 1.45 | 2.77 | 3.40 | 5.28 | 5.86 | 6.29 | 7.00–8.17 (9H) | 11.57 |  |
| 509 | 1.09 | 1.46 | 2.79 | 3.41 | 5.31 | 5.74 | 5.94 | 7.00–8.21 (9H) | 11.60 |  |
| 510 | 1.10 | 1.51 | 2.85 | 3.45 | 5.39 | 5.84 | 6.40 | 7.26–8.46 (9H) | 11.63 |  |
| 512 | 1.15 | 1.47 | 2.79 | 3.40 | 5.31 | 5.70 | 5.90 | 7.14–8.27 (9H) | 11.67 |  |
| 514 | 1.16 | 1.48 | 2.84 | 3.43 | 5.38 | 5.79 | 5.99 | 7.22–8.35 (9H) | 11.57 |  |
| 515 | 1.17 | 1.49 | 2.80 | 3.47 | 5.41 | 5.82 | 5.98 | 7.20–8.38 (9H) | 11.63 |  |
| 519 | 1.27 | 1.45 | 2.80 | 3.37 | 5.27 | 5.87 | 6.47 | 7.04–8.27 (9H) | 11.67 | 2.48 (3H, s, Ar—CH$_3$) |
| 522 | 1.16 | 1.49 | 2.79 | 3.41 | 5.37 | 5.72 | 6.07 | 7.17–8.44 (9H) | 11.60 |  |
| 524 | 1.34 | 1.48 | 2.83 | 3.42 | 5.30 | 5.89 | 6.42 | 7.00–8.34 (8H) | 11.66 | H* includes the thienyl group |

Explanation of Table 2
A: (3H, d, J=7Hz, ,—CH$_3$), B: (3H, d, J=7Hz, —CH$_3$), C: (3H, s, Ar—CH$_3$), D: (3H, s, —O—CH$_3$), E: (1H, d, J=8Hz, anomer proton), F: (1H, d, J=4Hz, anomer proton), G: (1H, s, —O—CH̄—O—), H*: (aromatic proton), I: (1H, s, phenolic proton)

SYNTHESIS EXAMPLE 7

Synthesis of 3',4'-O-isopropylidene-chartreusin (intermediate No. 527)

In 330 ml of anhydrous chloroform was dissolved 14.0 g of chartreusin, followed by adding thereto 100 ml of 2,2-dimethoxypropane and 300 mg of p-toluenesulfonic acid, and the resulting mixture was subjected to reaction with stirring at 25° to 30° C. for 8 hours.

After completion of the reaction, the reaction mixture was filtered and an aqueous sodium hydrogencarbonate solution was added, after which the resulting mixture was extracted with chloroform. The chloroform layer was washed with an aqueous sodium chloride solution and dried over anhydrous sodium sulfate. Then the chloroform was removed by distillation under reduced pressure to obtain an oily substance. Subsequently, the oily substance was crystallized from a mixed solvent of chloroform, ethanol and hexane to obtain 12.5 g of the desired compound.

NMR; (60 MHz, δ values in CDCl$_3$), 1.20–1.73 (12H, CH$_3$×4), 2.87 (3H, s, Ar-CH$_3$), 3.43 (3H, s, o-CH$_3$), 5.23 (1H, m, anomer proton), 5.90 (1H, m, anomer proton), 7.23–8.40 (5H, aromatic proton), 11.57 (1H, phenolic proton).

SYNTHESIS EXAMPLE 8

Synthesis of 3',4'-O-isobutylidene-chartreusin (intermediate No. 528)

In 20 ml of anhydrous chloroform was dissolved 500 mg of chartreusin, followed by adding thereto 30 ml of anhydrous methyl ethyl ketone, 800 mg of anhydrous copper sulfate and 50 mg of p-toluenesulfonic acid, and the resulting mixture was subjected to reaction with stirring at 25° to 30° C. for 48 hours.

After completion of the reaction, the reaction mixture was filtered and an aqueous sodium hydrogen-carbonate solution was added to the filtrate, after which the resulting mixture was extracted with chloroform. The chloroform layer was washed with an aqueous sodium chloride solution and dried. Then the chloroform was removed by distillation under reduced pressure to obtain an oily substance. Subsequently, the oily substance was purified by a silica gel column chromatography and the crystallized from a mixed solvent of chloroform, ethanol and hexane to obtain 125 mg of the desired compound.

NMR; (60 MHz, δ values in CDCl$_3$—CD$_3$ SOCD$_3$), 1.00–1.73 (14H, 3H×4, CH$_2$×1), 2.85 (3H, s, Ar-CH$_3$), 3.33 (3H, s, O—CH$_3$), 5.25 (1H, m, anomer proton), 5.73 (1H, m, anomer proton), 7.27–8.27 (5H, aromatic proton), 11.67 (1H, phenolic proton).

Intermediate Nos. 529 to 531 were synthesized according to Synthesis Examples 7 and 8 above. The structures and melting points of the intermediate Nos. 527 to 531 are tabulated in Table 3.

TABLE 3

| Intermediate No. | Structure (Note 1) | | Melting point (°C.) |
|---|---|---|---|
|  | $X_1$ | $X_2$ |  |
| 527 | Methyl | Methyl | 168.0–170.0 |
| 528 | Methyl | Ethyl | 203.0–208.0 |
| 529 | Hydrogen | Ethyl | 197.0–206.0 |
| 530 | Hydrogen | Acetylmethyl | 192.5–202.0 |
| 531 | Pentamethylene (cyclohexylidene) | | 243.5–253.5 |

Note 1: $X_1$ and $X_2$ represent substituent in the intermediate (II-1).

Next, specific synthesis examples of the intermediates (VIII) and (XI) are described below, via which intermediate the compound of this invention is synthesized by Process B (via monosilyl form) and Process C (via disilyl form).

SYNTHESIS EXAMPLE 9

Synthesis of 3',4'-O-isopropylidene-2"-O-(tert-butyl-dimethylsilyl)-chartreusin (intermediate No. 532)

In 18.4 ml of anhydrous dimethylformamide was dissolved 500 mg of the 3',4'-O-isopropylidene-chartreusin (intermediate No. 527) obtained in Synthesis Example 7 above, after which 400 mg of imidazole and 444 mg of tert-butyldimethylchlorosilane were added, and the resulting mixture was subjected to reaction with stirring at 0° C. for 6 hours.

After completion of the reaction, the reaction mixture was poured into an aqueous sodium hydrogen-carbonate solution and the resulting mixture was extracted with chloroform. The chloroform layer was dried and the solvent was removed by distillation under reduced pressure to obtain an oily substance. The oily substance was dissolved in 10 ml of hexamethylphosphorictriamide, followed by adding thereto 85 mg of potassium fluoride and 147 mg of potassium hydrogencarbonate, and the resulting mixture was subjected to reaction with stirring at 25° C. for 30 minutes.

After completion of the reaction, the reaction mixture was poured into an aqueous sodium hydrogen-carbonate solution and the resulting mixture was extracted with chloroform. The chloroform layer was dried and the solvent was removed by distillation under reduced pressure to obtain an oily substance. Subsequently, the oily substance thus obtained was subjected to a silica gel column chromatography to obtain crystals, which were then recrystallized from a mixed solvent of ethanol, chloroform and hexane to obtain 520 mg the desired compound having a melting point of 130°–135° C.

NMR; (60 MHz, $\delta$ values in CDCl$_3$) $-0.43$ (3H, s, Si—CH$_3$), $-0.22$ (3H, s, Si—CH$_3$), 0.47 (9H, s, Si-tert-C$_4$H$_9$), 1.17–1.77 (12H, CH$_3 \times 4$), 2.90 (3H, s, Ar—CH$_3$), 3.40 (3H, s, O—CH$_3$), 5.50 (2H, m, anomer proton$\times$2), 7.23–8.40 (5H, aromatic proton), 11.66 (1H, phenolic proton).

SYNTHESIS EXAMPLE 10

Synthesis of 3',4'-O-isopropylidene-2'',4''-di(tert-butyldimethylsilyl)-chartreusin (intermediate No. 533)

In 18.4 ml of anhydrous dimethylformamide was dissolved 500 mg of 3',4'-O-isopropylidene-charreusin (intermediate No. 527) obtained in Synthesis Example 7 above, after which 800 mg of imidazole and 888 mg of tert-butyldimethylchlorosilane were added, and the resulting mixture was subjected to reaction with stirring at 55° to 60° C. for 48 hours.

After completion of the reaction, the reaction mixture was poured into an aqueous sodium hydrogen-carbonate solution and the resulting mixture was extracted with chloroform. The chloroform layer was dried and the solvent was removed by distillation under reduced pressure to obtain an oily substance.

The oily substance was dissolved in 15 ml of hexamethylphosphorictriamide phosphate, followed by adding thereto 85 mg of potassium fluoride and 147 mg of potassium hydrogencarbonate, and the resulting mixture was subjected to reaction with stirring at 25° C. for 1 hour.

After completion of the reaction, the reaction mixture was poured into an aqueous sodium hydrogencarbonate solution and the resulting mixture was extracted with chloroform. The chloroform layer was dried and the solvent was removed by distillation under reduced pressure to obtain an oily substance. Subsequently, the oily substance thus obtained was subjected to a silica gel column chromatography to obtain 608 mg of the desired compound having a melting point of 119.5°–125.0° C.

NMR; (60 MHz, $\delta$ values in CDCl$_3$) $-0.38$ (3H, s, 2''-O-Si-CH$_3$), $-0.18$ (3H, s, 2''-O-Si-CH$_3$), 0.05 (6H, s, 4''-O-CH$_3 \times 2$), 0.48 (9H, s, 2''-O-Si-tert-C$_4$H$_9$), 0.88 (9H, s, 4''-O-Si-tert-C$_4$H$_9$), 1.10–1.80 (12H, CH$_3 \times 4$), 2.28 (3H, s, Ar-CH$_3$), 3.33 (3H, s, O—CH$_3$), 5.43 (2H, m, anomer proton$\times$2), 7.30–8.30 (5H, aromatic proton), 11.63 (1H, phenolic proton).

Next, specific synthesis examples of the intermediates (II-2), (XIV) and (II-3) are discribed below, via which intermediate the compound of this invention is synthesized by Process D and process E.

SYNTHESIS EXAMPLE 11

Synthesis of the exo form of 3',4'-O-benzylidene-4''-epiazido-4''-deoxy-chartreusin (intermediate No. 534)

(1) 7.0 Grams of the exo form of 3',4'-O-benzylidene-chartreusin (intermediate No. 501) was reacted in the same manner as in Synthesis Example 9 above to obtain 4.8 g of the exo form of 3',4'-O-benzylidene-2''-O-(tert-butyldimethylsilyl)-chartreusin (intermediate No. 534-1) having a melting point of 133.0°–138.0° C.

(2) In 110 ml of anhydrous pyridine was dissolved 4.8 g of the exo form of 3',4'-O-benzylidene-2''-O-(tert-butyldimethylsilyl)-chartreusin obtained in (1) above, followed by adding thereto 6.4 g of methanesulfonyl chloride, and the resulting mixture was subjected to reaction with stirring at 25° C. for 3 hours.

After completion of the reaction, chloroform was added to the reaction mixture and the mixture thus obtained was washed with water and dried, after which the solvent was removed by distillation under reduced pressure to obtain a crude product.

Subsequently, the crude product thus obtained was subjected to a silica gel column chromatography to obtain crystals, which were then recrystallized from a mixed solvent of ethanol, chloroform and hexane to obtain 4.4 g of 6,4''-O-dimethanesulfonyl-3',4'-O-benzylidene-2''-O-(tert-butyldimethylsilyl)-chartreusin (intermediate No. 534-2) having a melting point of 235°–237° C.

(3) In 90 ml of tetrahydrofuran was dissolved 4.3 g of the 6,4''-O-dimethanesulfonyl-3',4'-O-benzylidene-2''-O-(tert-butyldimethylsilyl)-chartreusin obtained in (2) above, followed by adding thereto a 1M tetrahydrofuran solution of tetra-n-butylammonium fluoride, and the resulting mixture was subjected to reaction with stirring at 30° C. for 3 hours.

After completion of the reaction, chloroform was added, and the mixture thus obtained was washed with water and dried, after which the solvent was removed by distillation under reduced pressure to obtain a crude product.

Subsequently, the crude product obtained was subjected to a silica gel chromatography to obtain crystals, which were then recrystallized from a mixed solvent of chloroform, ethanol and hexane to obtain 3.5 g of the exo form of 3',4'-O-benzylidene-4''-O-methanesulfonyl-chartreusin (intermediate No. 534-3) having a melting point of 172°–175° C.

(4) In 48 ml of hexamethylphosphorictriamide phosphate was dissolved 2 g of the exo form of 3',4'-O-benzylidene-4''-O-methanesulfonyl-chartreusin obtained in (3) above, after which 1.56 g of sodium azide was added and the resulting mixture was subjected to reaction with stirring at 95° C. for 3 hours.

After completion of the reaction, chloroform was added and the mixture thus obtained was washed with water and then concentrated under reduced pressure to obtain a crude substance, which was then subjected to a silica gel chromatography to obtain crystals. Subsequently, said crystals were recrystallized from a mixed solvent of chloroform, ethanol and hexane to obtain 1.3 g of the desired compound having a melting point of 213°-217° C.

SYNTHESIS EXAMPLE 12

Synthesis of the exo form of 3',4'-O-benzylidene-4"-epiamino-4"-deoxy-chartreusin (intermediate No. 535)

In a mixture of 5 ml of tetrahydrofuran, 2.5 ml of ethanol and 0.33 ml of acetic acid was dissolved 250 mg of the exo form of 3',4'-O-benzylidene-4"-epiazido-4"-deoxy-chartreusin (intermediate No. 534) obtained in Synthesis Example 11 above, followed by adding thereto 125 mg of 10% palladium-carbon, and the reaction was carried out in a hydrogen stream at 3 atmospheres at room temperature for 16 hours.

After completion of the reaction, 10 ml of water was added and the resulting mixture was filtered through Celite. The filtrate was neutralized with an aqueous sodium hydrogencarbonate solution and extracted with chloroform, and the chloroform layer was dried, after which the solvent was removed by distillation under reduced pressure. The crude product thus obtained was purified by a silica gel column chromatography to obtain crystals. Then, said crystals were recrystallized from a mixture of chloroform, ethanol and hexane to obtain 150 mg of the desired compound having a melting point of 194°-200° C.

SYNTHESIS EXAMPLE 13

Synthesis of the exo form of 3',4'-O-benzylidene-4"-(N-carbobenzyloxy-epiamino)-4"-deoxy-chartreusin (intermediate No. 536)

In a mixture of 3 ml of anhydrous chloroform and 0.1 ml of anhydrous pyridine was dissolved 100 mg of the exo form of 3',4'-O-benzylidene-4"-epiamino-4"-deoxy-chartreusin obtained in Synthesis Example 12 above, after which 24 mg of carbobenzoxy chloride was added, and the resulting mixture was subjected to reaction with stirring at 0° C. for 2 hours.

After completion of the reaction, ether was added and the resulting precipitate was collected and then purified by a silica gel column chromatography to obtain crystals. Subsequently, said crystals were recrystallized from a mixture of chloroform, ether and hexane to obtain 90 mg of the desired compound having a melting point of 259°-263° C.

Intermediate Nos. 537 to 540 were synthesized according to Synthesis Example 11 above.

Intermediate No. 537: the endo form of 3',4'-O-benzylidene-4"-epiazido-4"-deoxy-chartreusin m.p. 144.0°-147.0° C.

Intermediate No. 538: the endo form of 3',4'-O-(m-bromobenzylidene)-4"-epiazido-4"-deoxy-chartreusin m.p. 138.0°-140.0° C.

Intermediate No. 539: the endo form of 3',4'-O-(m-fluorobenzylidene)-4"-epiazido-4"-deoxy-chartreusin m.p. 143.0°-146.0° C.

Intermediate No. 540: 3',4'-O-isopropylidene-4"-epiazido-4"-deoxy-chartreusin m.p. 143.0°-145.0° C.

Next NMR data of typical intermediates obtained in Process D and Process E are shown in Table 4.

TABLE 4

| Intermediate No. | A | B | C | D | E | F | G | H* | I | J | K | L | M |
|---|---|---|---|---|---|---|---|---|---|---|---|---|---|
| 534 | 1.30 | 1.45 | 2.89 | 3.56 | 5.30 | 5.94 | 6.31 | 7.28–8.30 (10H) | — | — | — | — | — |
| 534-1 | 1.30 | 1.48 | 2.90 | 3.40 | — | — | 6.39 | 7.23–8.30 (10H) | −0.36, | −0.16 | 0.49 | 5.46–5.60 | 11.66 | — | — |
| 534-2 | 1.26 | 1.45 | 2.95 | 3.70 | — | — | 6.31 | 7.25–8.40 (10H) | −0.35, | −0.13 | 0.45 | 5.37–5.68 | — | 3.10, | 3.45 |
| 534-3 | 1.30 | 1.46 | 2.91 | 3.51 | 5.31 | 5.94 | 6.35 | 7.27–8.30 (10H) | — | — | — | — | — | 3.11 | — |
| 535 | 1.25 | 1.50 | 2.89 | 3.57 | 5.41 | 5.93 | 6.40 | 7.30–8.32 (10H) | — | — | — | — | — |
| 536 | 1.24 | 1.46 | 2.90 | 3.43 | 5.35 | 6.10 | 6.38 | 7.32–8.42 (15H) | — | — | Others: 5.15 (2H, s, benzyl proton) | | |
| 537 | 1.04 | 1.50 | 2.88 | 3.58 | 5.32 | 5.80 | 5.96 | 7.38–8.33 (10H) | — | — | — | — | — |
| 538 | 1.13 | 1.51 | 2.85 | 3.57 | 5.31 | 5.73 | 5.90 | 7.32–8.26 (9H) | — | — | — | — | — |
| 539 | 1.11 | 1.51 | 2.84 | 3.60 | 5.35 | 5.78 | 5.98 | 7.34–8.30 (9H) | — | — | — | — | — |
| 540 | — | — | 2.87 | 3.50 | 5.18 | 5.81 | — | 7.35–8.30 (5H) | — | — | Others: 1.25–1.63 (12H, 3H × 4) | | |

Explanation of Table 4

A: (3H, d, J=7Hz, —CH$_3$), B: (3H, d, J=7Hz, —CH$_3$), C: (3H, s, Ar—CH$_3$), D: (3H, s, —OCH$_3$), E: (1H, d, J=8Hz, anomer proton), F: (1H, d, J=4Hz, anomer proton), G: (1H, s, —OCHO—), H*: (aromatic proton), I: (3H, s, Si—CH$_3$), J: (9H, s, Si-tert-C$_4$H$_9$), K: (2H, m, anomer proton × 2), L: (1H, phenolic proton), M: (3H, s, O—SO$_2$CH$_3$)

Next, specific synthesis examples of the intermediates (II-4) and (II-5) are described below, via which intermediate the compound of this invention is synthesized by Process F and Process G.

SYNTHESIS EXAMPLE 14

Synthesis of 3',4'-O-isopropylidene-2"-dehydro-chartreusin (intermediate No. 541)

(1) In 4.4 ml of tetrahydrofuran was dissolved 200 mg of the 3',4'-O-isopropylidene-2",4"-O-di(tert-butyldimethylsilyl)-chartreusin (intermediate No. 533) obtained in Synthesis Example 10 above, followed by adding thereto 1.1 ml of a 2.0N aqueous hydrochloric acid solution, and the resulting mixture was subjected to reaction with stirring at room temperature for 3 hours.

After completion of the reaction, the reaction mixture was neutralized with sodium hydrogencarbonate, after which water was added and the resulting mixture was extracted with chloroform. The chloroform layer was washed with an aqueous sodium chloride solution, dried over anhydrous sodium sulfate, and then concentrated under reduced pressure to obtain a crude product.

Said crude product was purified by a silica gel column chromatography to obtain 140 mg of 4"-O-(tert-butyldimehtylsilyl)-chartreusin (intermediate No. 541-1, the melting point of crystals obtained by recrystallizing a part of this purified product from a mixture of chloroform, ether and hexane being 198.0°–210.0° C.).

(2) In 1.7 ml of anhydrous chloroform was dissolved 130 mg of the 4″-O-(tert-butyldimethylsilyl)-chartreusin obtained in (1) above, followed by adding thereto 0.34 ml of 2,2-dimethoxypropane, 300 mg of Molecular Sieves 4A 1/16 and about 2 mg of p-toluenesulfonic acid, and the reaction was carried out with stirring at room temperature for 30 minutes.

After completion of the reaction post-treatment was carried out in the same manner as in Synthesis Example 7 above, and then separation by a silica gel thin-layer chromatography (abreviated hereinafter as TLC) was conducted to obtain 126 mg of 3′,4′-O-isopropylidene-4″-O-(tert-butyldimehtylsilyl)-chartreusin (the melting point of crystals obtained by recrystallizing a part of the thus obtained compound from a mixture of chloroform, ether and hexane being 147.0°–153.0° C.).

(3) In 1.5 ml of N,N-dimethylformamide was dissolved 117 mg of the 3′,4′-O-isopropylidene-4″-O-(tert-butyldimethylsilyl)-chartreusin obtained in (2) above, followed by adding thereto 0.3 ml of a 1M tetrahydrofuran solution of tetra-n-butylammonium fluoride and 50 mg of benzyl bromide, and the resulting mixture was subjected to reaction with stirring at room temperature for 1.5 hours.

After completion of the reaction, an aqueous sodium hydrogencarbonate solution was added, and the resulting mixture was extracted with chloroform. The chloroform layer was washed with water and then with an aqueous sodium chloride solution, dried over anhydrous sodium sulfate, and then concentrated under reduced pressure to obtain a crude product.

Subsequently, said crude product was subjected to TLC to obtain 104 mg of 6-O-benzyl-3′,4′-O-isopropylidene-4″-O-(tert-butyldimethylsilyl)-chartreusin (intermediate No. 541-2, the melting point of crystals obtained by recrystallizing a part of the thus obtained compound from a mixture of chloroform, ether and hexane being 163.0°–166.0° C.).

(4) To a mixture of 1.0 ml of anhydrous pyridine and 10 ml of anhydrous methlene chloride was added 630 mg of chromic anhydride, and the reaction was carried out with stirring at room temperature for 30 minutes to prepare a complex of chromic acid and pyridine. Then, a solution prepared by dissolving the 6-O-benzyl-3′,4′-O-isopropylidene-4″-O-(tert-butyldimethylsilyl)-chartreusin obtained in (3) above in 5 ml of anhydrous methylene chloride was added all at once to the complex solution thus prepared, and the resulting mixture was subjected to reaction with stirring at room temperature for 30 minutes.

After completion of the reaction, ether and a small amount of chloroform were added, after which the resulting mixture was filtered through a silica gel column to remove insoluble chromic acid, and the filtrate was concentrated under reduced pressure to obtain a crude product.

Said crude product was subjected to a silica gel column chromatography and then recrystallized from a mixture of chloroform and ethanol to obtain 410 mg of 6-O-benzyl-3′,4′-O-isopropylidene-2″-dehydro-4″-O-(tert-butyldimethylsilyl)-chartreusin (intermediate No. 541-3) having a melting point of 216.0°–220.0° C.

(5) In a mixture of 3.0 ml of tetrahydrofuran and 3.0 ml of ethyl acetate was dissolved 262 mg of the 6-O-benzyl-3′,4′-O-isopropylidene-2″-dehydro-4″-o-(tert-butyldimethylsilyl)-chartreusin obtained in (4) above, after which 78 mg of palladium-carbon was added, and the reaction was carried out with stirring in a hydrogen stream at room temperature for 1.5 hours.

After completion of the reaction, the reaction mixture was filtered and the filtrate was concentrated under reduced pressure to obtain 260 mg of crude 3′,4′-O-isopropylidene-2″-dehydro-4″-O-(tert-butyldimethylsilyl)-chartreusin.

Subsequently, 260 mg of this crude compound was dissolved in 1.7 ml of tetrahydrofuran, followed by adding thereto 1.7 ml of a 1M tetrahydrofuran solution of tetra-n-butylammonium fluoride, and the resulting solution was subjected to reaction with stirring at 50° C. for 45 minutes.

After completion of the reaction, an aqueous sodium hydrogencarbonate solution was added, and the resulting mixture was extracted with chloroform. The chloroform layer was washed with an aqueous sodium chloride solution, dried, and then concentrated under reduced pressure to obtain a crude product. Then, said crude product was subjected to a silica gel column chromatography to obtain 190 mg of the desired compound (the melting point of crystals obtained by recrystallizing a part of the thus obtained compound from a mixture of chloroform, ether and ethanol being 184.0°–188.0° C.).

Intermediate Nos. 542 and 543 were synthesized according to Synthesis Example 14 above.

Intermediate No. 542: the exo form of 3′,4′-O-benzylidene-2″-dehydro-chartreusin
m.p. 218.0°–221.0° C.

Intermediate No. 543: the endo form of 3′,4′-O-benzylidene-2″-dehydro-chartreusin
m.p. 232.0°–237.0° C.

SYNTHESIS EXAMPLE 15

Synthesis of 3′,4′-O-isopropylidene-2″-epi-chartreusin (intermediate No. 544)

(1) In 20 ml of anhydrous tetrahydrofuran was dissolved 1.8 g of the 6-O-benzyl-3′,4′-O-isopropylidene-2″-dehydro-4″-O-(tert-butyldimethylsilyl)-chartreusin obtained in Synthesis Example 14 (4) above, and then a solution of 55 mg of sodium boron hydride in 3.5 ml of absolute methanol prepared at 0° C. was added dropwise to the tetrahydrofuran solution thus obtained over a period of 15 minutes. After completion of the dropwise addition, the reaction was carried out with stirring at 0° C. for 45 minutes.

After completion of the reaction, the reaction solution was made weakly acidic with diluted hydrochlric acid, after which an aqueous sodium hydrogen carbonate solution was added, and the resulting mixture was extracted with chloroform. The chloroform layer was washed with water and then with an aqueous sodium chloride solution, dried, and then concentrated under reduced pressure to obtain a crude product.

Said crude product was subjected to a silica gel column chromatography to obtain 816 mg of 6-O-benzyl-3′,4′-O-isopropylidene-2″-epi-4″-O-(tert-butyldimethylsilyl)-chartreusin (intermediate No. 544-1, the melting point of crystals obtained by recrystallizing a part of the thus obtained compound from a mixture of chloroform, hexane and ethyl acetate being 151.0°–155.0° C.).

(2) 174 Milligrams of the 6-O-benzyl-3′,4′-O-isopropylidene-2″-epi-4″-O-(tert-butyldimethylsilyl)-chartreusin obtained in (1) above was subjected to debenzylation and de-silylation according to Synthesis Example 14 (5) above, and recrystallized from a mixture of chloroform, ethyl acetate and hexane to obtain 102 mg of the desired compound having a melting point of 208.0°–210.0° C.

Intermediate Nos. 545 and 546 were synthesized according to Synthesis Example 15 above.

Intermediate No. 545: the exo form of 3',4'-O-benzylidene-2''-epi-chartreusin
m.p. 165.0°–168.0° C.

Intermediate No. 546: the endo form of 3',4'-O-benzylidene-2''-epi-chartreusin
m.p. 167.0°–170.0° C.

Next, NMR data of typical intermediates obtained in Process F and Process G are shown in Table 5.

thus obtained compound from a mixture of chloroform and hexane being 148.0°–152.0° C.).

(2) In 18 ml of anhydrous pyridine was dissolved 8.7 g of the 6-O-benzyl-3',4'-O-isopropylidene-chartreusin obtained in (1) above, followed by adding thereto 12 ml of acetic anhydride (acid anhydride), and the resulting mixture was subjected to reaction with stirring at room temperature for 16 hours.

After completion of the reaction, an aqueous sodium hydrogencarbonate solution was added and the resulting mixture was stirred at room temperature for 30 minutes, after which water was added and the mixture thus obtained was extracted with chloroform. The chloroform layer was washed successively with water, an

TABLE 5

| Intermediate No. | NMR Assignment (60 MHz, δ value, in CDCl₃) | | | | | | | | | | |
|---|---|---|---|---|---|---|---|---|---|---|---|
| | A | B | C | D | E | F | G | H* | I | J | Others (remarks) |
| 541 | — | — | 1.41, 1.48 | 1.42, 1.70 | 2.80 | 3.77 | — | — | 7.13–8.30 (5H) | — | 5.00 (1H, d, J = 8Hz), 5.12 (1H, d, d, J = 7Hz, 2Hz) 5.62 (1H, d, J = 2Hz) 6.00 (1H, s, anomer proton) |
| 541-1 | 0.08 | 0.92 | 1.31, 1.52 | — | 2.79 | 3.32 | 5.32 | 5.78 | 7.26–8.18 (5H) | 11.57 | — |
| 541-2 | 0.06 | 0.92 | 1.26, 1.46 | 1.42, 1.70 | 2.87 | 3.35 | — | 5.93 | 7.23–8.27 (10H) | — | 5.10–5.33 (3H, benzyl proton and anomer proton) |
| 541-3 | 0.04 | 0.84 | 1.33, 1.51 | 1.45, 1.72 | 2.85 | 3.24 | 5.08 | — | 7.18–8.30 (10H) | — | 5.23 (2H, s, benzyl proton) 5.85 (1H, s, anomer proton) |
| 544-1 | 0.07 | 0.88 | 1.27, 1.47 | 1.45, 1.71 | 2.86 | 3.22 | 5.06 | — | 7.29–8.22 (10H) | — | 5.22 (2H, s, benzyl proton) 5.86 (1H, d, J = 0–1 Hz, anomer proton) |
| 544 | — | — | — | —, 1.69 | 2.83 | 3.33 | 5.11 | — | 7.13–8.37 (5H) | 11.60 | 1.33–1.60 (9H, CH₃ × 3) 5.90 (1H, d, J = 0–1 Hz, anomer proton) |

Explanation of Table 5
A: (6H, s, Si—CH₃ × 2),
B: (9H, s, Si—C₄H₉),
C: (3H, d, J = 7Hz, CH₃),
D: (3H, s, —CH₃),
E: (3H, s, Ar—CH₃),
F: (3H, s, O—CH₃),
G: (1H, d, J = 8Hz, anomer proton),
H*: (1H, d, J = 4Hz, anomer proton),
I: (aromatic proton),
J: (1H, s, phenolic proton)

Next, specific synthesis examples of the intermediates (II-6) and (II-7) are described below, via which intermediate the compound of this invention is synthesized by Process H and Process I.

SYNTHESIS EXAMPLE 16

Synthesis of
3',4'-O-isopropylidene-3'-methyl-chartreusin
(intermediate No. 547)

(1) In 125 ml of dimethylformamide was dissolved 8.4 g of the 3',4'-O-isopropylidene-chartreusin (intermediate No. 527) obtained in Synthesis Example 7 above, followed by adding thereto 3.0 ml of benzyl bromide and 25.0 ml of a 1M tetrahydrofuran solution of tetra-n-butylammonium fluoride, and the resulting mixture was subjected to reaction with stirring at room temperature for 18 hours.

After completion of the reaction, an aqueous sodium hydrogencarbonate solution was added and the resulting mixture was extracted with chloroform. The chloroform layer was washed with water and then with an aqueous sodium chloride solution, dried, and then concentrated under reduced pressure to obtain a crude product. Said crude product was subjected to a silica gel column chromatography to obtain 8.7 g of 6-O-benzyl-3',4'-O-isopropylidene-chartreusin (the melting point of crystals obtained by recrystallizing a part of the aqueous sodium hydrogen-carbonate solution and an aqueous sodium chloride solution, dried, and then concentrated under reduced pressure to obtain a crude product. Said crude product was subjected to a silica gel column chromatography to obtain 8.3 g of 6-O-benzyl-3',4'-O-isopropylidene-2'',4''-O-diacetyl-chartreusin (intermediate No. 547-1, the melting point of crystals obtained by recrystallizing a part of the thus obtained compound from a mixture of ethyl acetate and hexane being 160.0°–163.0° C.).

(3) In 100 ml of tetrahydrofuran was dissolved 8.3 g of the 6-O-benzyl-3',4'-O-isopropylidene-2'',4''-O-diacetyl-chartreusin obtained in (2) above, after which 27 ml of a 2N aqueous hydrochloric acid solution was added, and the resulting mixture was subjected to reaction with stirring at room temperature for 3.5 hours.

After completion of the reaction, the reaction solution was neutralized with an aqueous sodium hydrogencarbonate solution and extracted with chloroform. The chloroform layer was washed with water and then with an aqueous sodium chloride solution, dried, and then concentrated under reduced pressure to obtain 7.92 g of crude 6-O-benzyl-2'',4''-diacetyl-chartreusin (the melting point of crystals obtained by recrystallizing a part of the thus obtained compound being 168.0°–173.0° C.).

(4) In 100 ml of dimethylformamide was dissolved 7.9 g of the crude 6-O-benzyl-2'',4''-O-diacetyl-chartreusin obtained in (3) above, followed by adding thereto 13.2 g of imidazole and 14.7 g of tert-butyldimethylchlorosilane, and the resulting mixture was subjected to reaction with stirring at room temperature for 15 hours.

After completion of the reaction, an aqueous sodium hydrogencarbonate solution was added and the resulting mixture was extracted with chloroform. The chloroform layer was washed with water and then with an aqueous sodium chloride solution, dried, and then concentrated under reduced pressure to obtain a crude product. Said crude product was subjected to a silica gel column chromatography, and there were obtained 2.09 g of 6-O-benzyl-3'-O-(tert-butyldimethylsilyl)-2'',4''-O-diacetyl-chartreusin (intermediate No. 547-2) having a melting point of 145.0°-148.0° C. from the nonpolar fraction and 3.98 g of 6-O-benzyl-4'-O-(tert-butyldimethylsilyl)-2'',4''-O-diacetyl-chartreusin (intermediate No. 547-3) having a melting point of 153.0°-155.0° C. from the polar fraction.

(5) In the same manner as in Synthesis Example 14 (4) above, 1.74 g of the 6-O-benzyl-4'-O-(tert-butyldimethylsilyl)-2'',4''-O-diacetyl-chartreusin obtained as polar fraction in (4) above was oxidized with chromic acid to obtain 1.27 g of 6-O-benzyl-3'-dehydro-4'-O-(tert-butyldimethylsilyl)-2'',4''-O-diacetyl-chartreusin (intermediate No. 547-4, the melting point of crystals obtained by recrystallizing a part of the thus obtained compound being 158.0°-159.5° C.).

There are described below physical properties of 6-O-benzyl-3'-O-(tert-butyldimethylsilyl)-4'-dehydro-2'',4''-O-diacetyl-chartreusin obtained by oxidizing the 6-O-benzyl-3'-O-(tert-butyldimethylsilyl)-2'',4''-O-diacetyl chartreusin obtained as nonpolar fraction in (4) above, in the same manner as in Synthesis Example 14 (4) above. Melting point 128.0°-130.0° C.

NMR: (400 MHz, $\delta$ values in CDCl$_3$), 0.16 (3H, s, Si—CH$_3$), 0.19 (3H, s, Si—CH$_3$), 1.03 (9H, s, Si—C$_4$H$_9$), 1.19 (3H, d, J=6.4 Hz, 5''-CH$_3$), 1.50 (3H, s, 2''-OAc), 1.51 (3H, d, J=7 Hz, 5'-CH$_3$), 2.07 (3H, s, 4''-OAc), 2.90 (3H, s, Ar—CH$_3$), 3.31 (3H, s, O—CH$_3$), 3.73 (1H, d, d, J=10.5 Hz, 3.4 Hz, 3''-H), 4.37 (1H, q, J=7 Hz, 5'-H), 4.44 (1H, q, d, J=6.4 Hz, −1 Hz, 5''-H), 4.69 (1H, d, J=10 Hz, 3'-H), 4.76 (1H, d, d, J=10 Hz, 5.3 Hz, 2'-H), 4.85 (1H, d, J=10.5 Hz, 3.7 Hz, 2''-H), 5.25 (2H, s, benzyl proton), 5.33 (1H, d, d, J=3.4 Hz, −1 Hz, 4''-H), 5.68 (1H, d, J=3.7 Hz, 1''-H), 5.80 (1H, d, J=5.3 Hz, 1'-H), 7.35-8.15 (10H, aromatic proton).

(6) In 8.0 ml of anhydrous tetrahydrofuran was dissolved 1.07 g of the 6-O-benzyl-3'-dehydro-4'-O-(tert-butyldimethylsilyl)-2'',4''-O-diacetyl-chartreusin obtained in (5) above, and 1.3 ml of 0.78M ethereal solution of methyllithium was added dropwise at −78° C. After the completion of the dropwise addition, the resulting mixture was stirred for several minutes. After the stirring, the mixture was neutralized with about 10 ml of a 0.1N aqueous hydrochloric acid solution, after which an aqueous sodium hydrogencarbonate solution was added and the mixture thus obtained was extracted with chloroform. The chloroform layer was washed with water and then with an aqueous sodium chloride solution, dried, and then concentrated under reduced pressure to obtain a crude product. Subsequently, said crude product was dissolved in 5.8 ml of tetrahydrofuran, followed by adding thereto a 1M tetrahydrofuran solution of tetra-n-butylammonium fluoride, and the resulting solution was subjected to reaction with stirring at room temperature for 10 minutes.

After completion of the reaction, an aqueous sodium hydrogencarbonate solution was added and the resulting mixture was extracted with chloroform. The chloroform layer was washed with water and then with an aqueous sodium chloride solution, dried, and then concentrated to obtain 950 mg of crude 6-O-benzyl-3'-methyl-2'',4''-O-diacetyl-chartreusin.

(7) According to Synthesis Example 14 (2) above, 950 mg of the crude 6-O-benzyl-3'-methyl-2'',4''-O-diacetyl-chartreusin was converted to an acetal, and the crude product thus obtained was separated and purified by a silica gel column chromatography, followed by TLC to obtain 193 mg of 6-O-benzyl-3',4'-O-isopropylidene-3'-methyl-2'',4''-O-diacetyl-chartreusin (intermediate No. 547-5, the melting point of crystals obtained by recrystallizing a part of the thus obtained compound from a mixture of ethyl acetate and hexane being 167.0°-170.0° C.).

(8) In a mixture of 1.0 ml of absolute methanol and 0.4 ml of anhydrous toluene was dissolved 30 mg of the 6-O-benzyl-3',4'-O-isopropylidene-3'-methyl-2'',4''-O-diacetyl-chartreusin obtained in (7) above, followed by adding thereto 0.1 ml of a 0.7N methanolic solution of sodium methoxide, and the resulting mixture was subjected to reaction with stirring at room temperature for 24 hours.

After completion of the reaction, the reaction mixture was neutralized with diluted hydrochloric acid, after which an aqueous sodium hydrogencarbonate solution was added and the resulting mixture was extracted with chloroform. The chloroform layer was washed with an aqueous sodium chloride solution, dried and then concentrated under reduced pressure to obtain a crude product. Said crude product was subjected to TLC to obtain 10 mg of 6-O-benzyl-3',4'-O-isopropylidene-3'-methyl-chartreusin (intermediate No. 547-6, the melting point of crystals obtained by recrystallizing a part of the thus obtained compound from a mixture of ethyl acetate and hexane being 167.0°-168.5° C.).

(9) In 1.0 ml of tetrahydrofuran was dissolved 10 mg of the 6-O-benzyl-3',4'-O-isopropylidene-3'-methyl-chartreusin obtained in (8) above, after which 2 mg of palladium-carbon was added, and the resulting mixture was subjected to reaction with stirring in a hydrogen stream at room temperature for 1.5 hours.

After completion of the reaction, the reaction mixture was filtered and then the filtrate was concentrated under reduced pressure to obtain a crude product. Subsequently, said crude product was subjected to a silica gel column chromatography to obtain 8 mg of the desired compound (the melting point of crystals obtained by recrystallizing a part of the thus obtained compound from a mixture of chloroform, ethanol and hexane being 264.0°-266.0° C.).

Next, NMR data of typical intermediates obtained in Process H and Process I are shown in Table 6.

TABLE 6

| Intermediate No. | A | B | C | D | E | F | G | H | Others (remarks) |
|---|---|---|---|---|---|---|---|---|---|
| 547 | — — | — — | 1.42, 1.46 1.71 | 2.84 | 3.41 | — | 5.85 | 7.29–8.36 (5H) | 1.29–1.52 (3H × 2, CH$_3$ × 2) 5.22 (1H, d, J = 8Hz, anomer proton) |

TABLE 6-continued

| Inter-mediate No. | NMR Assignment (60 MHz, δ value, in CDCl₃) | | | | | | | | Others (remarks) |
|---|---|---|---|---|---|---|---|---|---|
| | A | B | C | D | E | F | G | H | |
| 547-1 | 0.85, 2.13 | 1.24, 1.49 | 1.45, 1.73 | 2.97 | 3.27 | 5.15–5.45 | 5.98 | 7.10–8.25 (10H) | 11.62 (1H, s, phenolic proton) — |
| 547-2 | 1.12, 2.08 | 1.22, 1.37 | — — | 2.92 | 3.25 | 5.17–5.40 | 6.15 | 7.17–8.30 (10H) | 0.22 (6H, s, Si—CH₃ × 2) 1.02 (9H, s, Si—C₄H₉) |
| 547-3 | 0.83, 2.10 | 1.17, 1.33 | — — | 2.93 | 3.23 | 5.20–5.50 | 5.95 | 7.33–8.23 (10H) | 0.15 (3H, s, Si—CH₃) 0.23 (3H, s, Si—CH₃) 1.00 (9H, s, Si—C₄H₉) |
| 547-4 | 0.82, 2.10 | 1.12, 1.41 | — — | 2.93 | 3.27 | — | 5.92 | 7.27–8.25 (10H) | 0.17 (6H, s, Si—CH₃ × 2) 0.97 (9H, s, Si—C₄H₉) 5.22 (2H, s, benzyl proton) |
| 547-5 | 0.82, 2.08 | 2.24, — | 1.71, — | 2.92 | 3.22 | 5.09–5.24 | 6.03 | 7.06–8.22 (10H) | 1.36–1.59 (9H, —CH₃ × 3) |
| 547-6 | — — | — — | 1.44, 1.48 1.72 | 2.88 | 3.43 | — | 5.89 | 7.26–8.26 (10H) | 1.29–1.53 (3H, × 2, CH₃ × 2) 5.19 (2H, s, benzyl proton) 5.24 (1H, d, J = 8Hz, anomer proton) |

Explanation of TABLE 6
A: (3H, s, —OA),
B: (3H, d, J = 7Hz, CH₃),
C: (3H, s, —CH₃),
D: (3H, s, Ar—CH₃),
E: (3H, s, O—CH₃),
F: (3H, benzyl proton and anomer proton),
G: (1H, d, J = 4Hz, anomer proton),
H: (anomer proton)

Next, typical examples of the intermediate (X) via which the compound of this invention is synthesized are listed in Table 7.

TABLE 7

| Intermediate No. | Q Note 1 | Rf value Note 2 | Melting point (°C.) |
|---|---|---|---|
| 548 | —CH₂N(CH₃)(COCF₃) | 0.32 | — |
| 549 | —(CH₂)₂NHCHO | 0.16 | — |
| 550 | —(CH₂)₂NHCOCH₃ | 0.20 | 212.0–219.0 |
| 551 | —(CH₂)₂NHCOCCl₃ | 0.28 | 193.5–199.0 |
| 552 | —(CH₂)₂NHCOOCH₂-(phenyl) | 0.32 | — |
| 553 | —(CH₂)₃NHCOOCH₂-(phenyl) | 0.33 | 229.0–234.5 |
| 554 | —(CH₂)₄NHCOCF₃ | 0.25 | — |
| 555 | —(CH₂)₅NHCOOCH₂-(phenyl) | 0.33 | 243.5–249.0 |
| 556 | —(CH₂)₁₁NHCOCH₃ | 0.23 | 218.5–227.5 |
| 557 | —CH(CH₃)(CH₂NHCOCF₃) | 0.26 | 222.0–230.5 |
| 558 | —CH(CH₃)(CH₂NHCO-(phenyl)) | 0.28 | 157.0–176.0 |
| 559 | —CH(CH₃)(CH₂NHCOOCH₂-(phenyl)) | 0.32 | — |
| 560 | —CH₂CH(CH₃)(NHCOCF₃) | 0.26 | — |
| 561 | —(CH₂)₂NHCOCH₂NHCOOCH₂-(phenyl) | 0.25 | — |
| 562 | —CH₃ | 0.28 | 231.0–252.5 |
| 563 | —CH₂CH(CH₃)₂ | 0.33 | — |
| 564 | —(CH₂)₄CH₃ | 0.27 | 245.0–250.5 |

TABLE 7-continued

| Intermediate No. | Q Note 1 | Rf value Note 2 | Melting point (°C.) |
|---|---|---|---|
| 565 | —CH₂CH(CH₃)(CH₂C(CH₃)₃) | 0.28 | 190.5–194.5 |
| 566 | —CH(CH₂CH₃)((CH₂)₃CH₃) | 0.35 | 216.5–225.0 |
| 567 | —CH(CH₂)(CH—CH₃) (cyclopropyl with methyl) | 0.31 | — |
| 568 | —(CH₂)₂-(cyclohexyl) | 0.32 | 224.0–227.5 |
| 569 | —CH=CHCH=CHCH₃ | 0.33 | 188.0–204.0 |
| 570 | 3-cyclohexenyl | 0.30 | — |
| 571 | —(CH₂)₂C≡CH | 0.28 | 245.5–256.0 |
| 572 | —CH(Br)(CH(CH₃)₂) | 0.30 | — |
| 573 | —CH=C(CF₃)(CH₃) | 0.29 | — |
| 574 | —CH₂O-(phenyl) | 0.32 | 208.5–227.0 |
| 575 | —(CH₂)₃OCH₂-(phenyl) | 0.32 | — |
| 576 | —CH₂S-(phenyl) | 0.31 | — |
| 577 | —CH₂OCOCH₃ | 0.32 | — |
| 578 | —(CH₂)₂COCH₃ | 0.29 | 261.0–268.5 |
| 579 | —(CH₂)₂COOCH₃ | 0.29 | — |
| 580 | —(o-chlorophenyl) | 0.28 | 245.5–249.5 |
| 581 | —(p-cyanophenyl) | 0.32 | 231.5–235.0 |
| 582 | —(p-trifluoromethylphenyl) | 0.30 | 255.0–272.5 |

Note 1: Q is a substituent in the intermediate (x).
Note 2: Rf values were measured by a silica gel thin-layer chromatography (Merck Silica Gel 60GF$_{254}$) using a mixed solvent of chloroform and methanol (8:1) as a developing solvent.

Next, specific synthesis examples of the compounds of this invention are described below.

SYNTHESIS EXAMPLE 17

Synthesis of the exo form of 6-O-(2-thienyl-carbonyl)-3',4'-O-benzylidene-chartreusin (referred to hereinafter as compound No. 11)

In a mixture of 0.7 ml of anhydrous pyridine, 0.7 ml of anhydrous chloroform and 0.7 ml of anhydrous ethyl acetate was dissolved 50 mg of the exo form of 3',4'-O-benzylidene-chartreusin (intermediate No. 501) obtained in Synthesis Example 1 above, followed by adding thereto 36 mg of 2-thiophenecarboxylic acid and 84 mg of dicyclohexylcarbodiimide, and the resulting mixture was subjected to reaction with stirring at room temperature for 9 hours.

After completion of the reaction, a small amount of methanol was added, after which the resulting mixture was filtered and the filtrate was concentrated under reduced pressure. The oily substance thus obtained was subjected to TLC to obtain crude crystals. Subsequently, said crude crystals were recrystallized from a mixture of chloroform, ethanol and ether to obtain 52 mg of crystals of the desired compound.

SYNTHESIS EXAMPLE 18

Synthesis of the exo form of 6-O-{2-(5-methoxyindolyl)-carbonyl}-3',4'-O-benzylidene-chartreusin (referred to hereinafter as compound No. 19)

In a mixture of 0.96 ml of anhydrous pyridine and 0.48 ml of anhydrous chloroform was dissolved 70 mg of the exo form of 3',4'-O-benzylidene-chartreusin (intermediate No. 501) obtained in Synthesis Example 1 above, followed by adding thereto 55 mg of 5-methoxyindole-2-carboxylic acid and 79 mg of dicyclohexylcarbodiimide, and the resulting mixture was subjected to reaction with stirring at room temperature for 26 hours.

After completion of the reaction, 0.1 ml of methanol and 5 ml of ethyl acetate were added, after which the resulting mixture was filtered and the filtrate was concentrated under reduced pressure. The oily substance thus obtained was subjected to TLC to obtain crystals. Then, said crystals were recrystallized from a mixture of chloroform and ethyl acetate to obtain 49 mg of the desired compound.

SYNTHESIS EXAMPLE 19

Synthesis of the endo form of 6-O-(2-indolyl-carbonyl)-3',4'-O-(m-fluorobenzylidene)-chartreusin (referred to hereinafter as compound No. 30)

In a mixture of 1.4 ml of anhydrous pyridine and 0.7 ml of anhydrous chloroform was dissolved 100 mg of the endo form of 3',4'-O-(m-fluorobenzylidene)-chartreusin (intermediate No. 505) obtained in Synthesis Example 4 above, followed by adding thereto 65 mg of indole-2-carboxylic acid and 83 mg of dicyclohexylcarbodiimide, and the resulting mixture was subjected to reaction with stirring at room temperature for 2 hours.

After completion of the reaction, a small amount of methanol was added, after which the resulting mixture was filtered and the filtrate was concentrated under reduced pressure. The oily substance thus obtained was subjected to TLC to obtain crystals. Subsequently, said crystals were recrystallized from a mixture of chloroform and hexane to obtain 45 mg of the desired compound.

SYNTHESIS EXAMPLE 20

Synthesis of 6-O-{2-(5-bromofuryl)-carbonyl}-3',4'-O-isopropylidene-chartreusin (referred to hereinafter as compound No. 8)

(1) In a mixture of 2.5 ml of anhydrous chloroform, 2.5 ml of anhydrous pyridine and 2.5 ml of anhydrous ethyl acetate was dissolved 200 mg of the 3',4'-O-isopropylidene-2''-O-(tert-butyldimethylsilyl)-chartreusin (intermediate No. 532) obtained in Synthesis Example 9 above, followed by adding thereto 120 mg of 2-(5-bromofuran)-carboxylic acid and 182 mg of dicyclohexylcarbodiimide, and the resulting mixture was subjected to reaction with stirring at room temperature for 4 hours.

After completion of the reaction, post-treatment and separation were carried out in the same manner as in Synthesis Example 17 above to obtain 180 mg of 6-O-{2-(5-bromofuryl)-carbonyl}-3',4'-O-isopropylidene-2''-O-(tert-butyldimethylsily)-chartreusin.

(2) In a mixture of 3.7 ml of tetrahydrofuran and 1.9 ml of a 3N aqueous hydrochloric acid solution was dissolved 180 mg of the 6-O-{2-(5-bromofuryl)-carbonyl}-3',4'-O-isopropylidene-2''-O-(tert-butyldimethylsilyl)-chartreusin obtained in (1) above, and the resulting solution was subjected to reaction with stirring at room temperature for 2 hours.

After completion of the reaction, the reaction solution was neutralized with sodium hydrogencarbonate and then extracted with chloroform. The chloroform layer was washed with an aqueous sodium chloride solution, dried over anhydrous sodium sulfate, and then concentrated under reduced pressure to obtain 150 mg of crude 6-O-{2-(5-bromofuryl)-carbonyl}-chartreusin.

(3) In 9.3 ml of anhydrous chloroform was dissolved 150 mg of the 6-O-{2-(5-bromofuryl)-carbonyl}-chartreusin obtained in (2) above, followed by adding thereto 1.1 ml of 2,2-dimethoxypropane and 5 mg of p-toluenesulfonic acid, and the resulting mixture was subjected to reaction with stirring at room temperature for 16 hours.

After completion of the reaction, an aqueous sodium hydrogencarbonate solution was added and the resulting mixture was extracted with chloroform. Subsequently, the chloroform layer was washed with an aqueous sodium chloride solution, dried over anhydrous sodium sulfate, and then concentrated under reduced pressure to obtain an oily substance. The oily substance was subjected to TLC to obtain crystals. Then, said crystals were recrystallized from a mixture of chloroform, ethanol, ether and hexane to obtain 75 mg of the desired compound.

SYNTHESIS EXAMPLE 21

Synthesis of 6-O-(N-carbobenzyloxy-prolyl)-3',4'-O-isopropylidene-chartreusin (referred to hereinafter as compound No. 3)

(1) In a mixture of 1.7 ml of anhydrous chloroform and 1.7 ml of anhydrous pyridine was dissolved 150 mg of the 3',4'-O-isopropylidene-2'',4''-di(tert-butyldimethylsilyl)-chartreusin (intermediate No. 533) obtained in Synthesis Example 10 above, after which 123 mg of N-carbobenzyloxy-proline was added, followed by adding thereto dropwise 0.07 ml of thionyl chloride at 0° C. Subsequently, the resulting mixture was subjected to reaction with stirring at 0° C. for 1 hour.

After completion of the reaction, an aqueous sodium hydrogencarbonate solution was added and the resulting mixture was extracted with chloroform. The chloroform layer was washed with an aqueous sodium chloride solution, dried over anhydrous sodium sulfate and then concentrated under reduced pressure. The ether-soluble fraction alone was concentrated under reduced pressure again to obtain 200 mg of crude 6-O-(N-carbobenzyloxyprolyl)-3',4'-O-isopropylidene-2'',4''-di(-tert-butyldimethylsilyl)-chartreusin.

(2) In a mixture of 5.1 ml of tetrahydrofuran and 1.7 ml of a 3N aqueous hydrochloric acid solution was dissolved 200 mg of the 6-O-(N-carbobenzyloxy-prolyl)-3',4'-O-isopropylidene-2'',4''-di(tert-butyldimethylsilyl)-chartreusin obtained in (1) above, and the resulting solution was subjected to reaction with stirring at room temperature for 24 hours.

After completion of the reaction, post-treatment was carried out in the same manner as in Synthesis Example 20 (2) above to obtain 142 mg of crude 6-O-(N-carbobenzyloxy-prolyl)-chartreusin.

(3) In 8.2 ml of anhydrous chloroform was dissolved 142 mg of the 6-O-(N-carbobenzyloxy-prolyl)-chartreusin obtained in (2) above, after which 1.0 ml of 2,2-dimethoxypropane and 5 mg of p-toluenesulfonic acid were added and the resulting mixture was subjected to reaction with stirring at room temperature for 2.5 hours.

After completion of the reaction, post-treatment and separation were carried out in the same manner as in Synthesis Example 20 (3) above to obtain 77 mg of the desired compound.

SYNTHESIS EXAMPLE 22

Synthesis of the exo form of 6-O-(N-trifluoroacetyl-6-amino-n-hexanoyl)-3',4'-O-benzylidene-4''-epiamino-4''-deoxy-chartreusin hydrochloride (referred to hereinafter as compound No. 37)

(1) In a mixture of 3.3 ml of anhydrous pyridine and 1.6 ml of anhydrous chloroform was dissolved 250 mg of the exo form of 3',4'-O-benzylidene-4''-epiazido-4''-deoxy-chartreusin (intermediate No. 534) obtained in Synthesis Example 11 above, followed by adding thereto 187 mg of N-trifluoroacetyl-6-amino-n-caproic acid and 238 mg of dicyclohexylcarbodiimide, and the resulting mixture was subjected to reaction with stirring at room temperature for 4 hours.

After completion of the reaction, a small amount of methanol was added, after which the reaction mixture was filtered and the filtrate was concentrated under reduced pressure. The oily substance thus obtained was subjected to a silica gel column chromatography to obtain crystals. Then, said crystals were recrystallized from a mixture of chloroform and hexane to obtain 260 mg of 6-O-(N-trifluoroacetyl-6-amino-n-hexanoyl)-3',4'-O-benzylidene-4''-epiazido-4''-deoxy-chartreusin [intermediate (I) of compound No. 37].

(2) In a mixture of 5.4 ml of tetrahydrofuran and 0.27 ml of acetic acid was dissolved 260 mg of the exo form of 6-O-(N-trifluoroacetyl-6-amino-n-hexanoyl)-3',4'-O-benzylidene-4''-epiazido-4''-deoxy-chartreusin obtained in (1) above, followed by adding thereto 130 mg of 10% palladium-carbon, and the resulting mixture was subjected to reaction with shaking in a hydrogen stream (3 atmospheres) at room temperature for 15 hours.

After completion of the reaction, 5 ml of water was added and the resulting mixture was filtered through Celite. The filtrate was neutralized with an aqueous sodium hydrogencarbonate solution and extracted with chloroform, after which the chloroform layer was dried, and the solvent was removed by distillation under reduced pressure. The crude product thus obtained was subjected to a silica gel column chromatography to obtain crystals. Subsequently, the crystals obtained were recrystallized from a mixture of chloroform, methanol and ether to obtain 124 mg of the exo form of 6-O-(N-trifluoroacetyl-6-amino-n-hexanoyl)-3',4'-O-benzylidene-4''-epiamino-4''-deoxy-chartreusin [intermediate (II) of compound No. 37].

(3) In a mixture of 1.3 ml of a 0.1N aqueous hydrochloric acid solution and 10 ml of water was dissolved 124 mg of the exo form of 6-O-(N-trifluoroacetyl-6-amino-n-hexanoyl)-3',4'-O-benzylidene-4''-epiamino-4''-deoxy-chartreusin obtained in (2) above, and the resulting mixture was freeze-dried to obtain 124 mg of the desired compound.

SYNTHESIS EXAMPLE 23

Synthesis of the exo form of
6-O-(3-methyl-n-butyryl)-3',4'-O-benzylidene-4''-epiamino-4''-deoxy-chartreusin hydrochloride (referred to hereinafter as compound No. 39)

(1) In a mixture of 3.9 ml of anhydrous pyridine and 2 ml of anhydrous chloroform was dissolves 300 mg of the exo form of 3',4'-O-benzylidene-4''-epiazido-4''-deoxy-chartreusin (intermediate No. 534) obtained in Synthesis Example 11 above, followed by adding thereto 177 mg of 3-methyl-n-butyric acid and 281 mg of dicyclohexylcarbodiimide, and the resulting mixture was subjected to reaction with stirring at room temperature for 3 hours.

After completion of the reaction, a small amount of methanol was added, after which the resulting mixture was filtered, and the filtrate was concentrated under reduced pressure. The oily substance thus obtained was subjected to a silica gel column chromatography to obtain crystals. Subsequently, the crystals obtained were recrystallized from a mixture of chloroform, ethanol and hexane to obtain 200 mg of the exo form of 6-O-(3-methyl-n-butyryl)-3',4'-O-benzylidine-4''-epiazido-4''-deoxy-chartreusin [intermediate (I) of compound No. 39].

(2) In a mixture of 3 ml of tetrahydrofuran and 0.2 ml of acetic acid was dissolved 190 mg of the exo form of 6-O-(3-methyl-n-butyryl)-3',4'-O-benzylidene-4''-epiazido-4''-deoxy-chartreusin obtained in (1) above, followed by adding thereto 95 mg of 10% palladium-carbon, and the resulting mixture was subjected to reaction with shaking in a hydrogen stream (3 atmospheres) at room temperature for 20 hours.

After completion of the reaction, 5 ml of water was added and the resulting mixture was filtered through Celite. The filtrate was neutralized with an aqueous sodium hydrogencarbonate solution and extracted with chloroform, after which the chloroform layer was dried, and the solvent was removed by distillation under reduced pressure. The crude product thus obtained was subjected to a silica gel column chromatography to obtain crystals. Then, the crystals obtained were recrystallized from a mixture of chloroform and hexane to obtain 57 mg of the exo form of 6-O-(3-methyl-n-butyryl)-3',4'-O-benzylidene-4''-epiamino-4''-deoxy-chartreusin [intermediate (II) of compound No. 39].

(3) In a mixture of 0.4 ml of 0.1N hydrochloric acid and 10 ml of water was dissolved 40 mg of the exo form of 6-O-(3-methyl-n-butyryl)-3',4'-O-benzylidene-4''-epiamino-4''-deoxy-chartreusin obtained in (2) above, and the resulting solution was freeze-dried to obtain 40 mg of the desired compound.

SYNTHESIS EXAMPLE 24

Synthesis of the exo form of
6-O-(β-amino-isobutyryl)-3',4'-benzylidene-4''-epiamino-4''-deoxy-chartreusin dihydrochloride (referred to hereinafter as compound No. 34)

(1) In a mixture of 2.4 ml of anhydrous pyridine and 1.2 ml of anhydrous chloroform was dissolved 200 mg of the exo form of 3',4'-O-benzylidene-4''-(N-carbobenzyloxy-epiamino)-4''-deoxy-chartreusin (intermediate No. 536) obtained in Synthesis Example 13 above, followed by adding thereto 82 mg of N-carbobenzyloxy-β-amino-isobutyric acid and 179 mg of dicyclohexylcarbodiimide, and the reaction was carried out with stirring at room temperature for 4 hours.

After completion of the reaction, a small amount of methanol was added, after which the resulting mixture was filtered and the filtrate was concentrated under reduced pressure. The oily substance thus obtained was subjected to a silica gel column chromatography to obtain crystals. Subsequently, the crystals obtained were recrystallized from a mixture of chloroform and ether to obtain 140 mg of the exo form of 6-O-(N-carbobenzyloxy-β-amino-isobutyryl)-3',4'-O-benzylidene-4''-(N-carbobenzyloxy-epiamino)-4''-deoxy-chartreusin [intermediate (I) of compound No. 34].

(2) In a mixture of 25 ml of tetrahydrofuran and 2 ml of 0.1N hydrochloric acid was dissolved 140 mg of the 6-O-(N-carbobenzyloxy-β-amino-isobutyryl)-3',4'-O-benzylidene-4''-(N-carbobenzyloxy-epiamino)-4''-deoxy-chartreusin obtained in (1) above, followed by adding thereto 75 mg of 10% palladium-carbon, and the resulting mixture was subjected to reaction with stirring in a hydrogen stream at 0° C. for 6 hours.

After completion of the reaction, 15 ml of water was added and the resulting mixture was filtered through Colite. The filtrate was washed three times with ethyl acetate and then once with chloroform, after which the filtrate (the aqueous layer) was freeze-dried obtain 65 mg of the desired compound.

SYNTHESIS EXAMPLE 25

Synthesis of the exo form of 6-O-(m-methoxybenzoyl)-3',4'-O-benzylidene-4''-epiamino-4''-deoxy-chartreusin (referred to hereinafter as compound No. 51)

(1) In a mixture of 2.4 ml of anhydrous pyridine and 1.2 ml of anhydrous chloroform was dissolved 100 mg of the exo form of 3',4'-O-benzylidene-4''-(N-carbobenzyloxy-epiamino)-4''-deoxy-chartreusin (intermediate No. 536) obtained in Synthesis Example 13 above, followed by adding thereto 27 mg of m-anisic acid and 74 mg of dicyclohexylcarbodiimide, and the reaction was carried out with stirring at room temperature for 20 hours.

After completion of the reaction, a small amount of methanol was added, after which the resulting mixture was filtered and the filtrate was concentrated under reduced pressure. The oily substance thus obtained was subjected to a silica gel column chromatography to obtain crystals. Subsequently, the crystals obtained were recrystallized from a mixture of chloroform, methanol and ether to obtain 90 mg of the exo form of 6-O-(m-methoxybenzoyl)-3',4'-O-benzylidene-4''-(N-carbobenzyloxy-epiamino)-4''-deoxy-chartreusin [intermediate (I) of compound No. 51].

(2) In a mixture of 10 ml of tetrahydrofuran and 5 ml of methanol was dissolved 90 mg of the exo form of 6-O-(m-methoxybenzoyl)-3',4'-O-benzylidene-4''-(N-carbobenzyloxy-epiamino)-4''-deoxy-chartreusin obtained in (1) above, followed by adding thereto 45 mg of 10% palladium-carbon, and the resulting mixture was subjected to reaction with stirring in a hydrogen stream at 0° C. for 6 hours.

After completion of the reaction, the reaction mixture was filtered through Celite and the solvent was removed by distillation under reduced pressure, after which the crude product thus obtained was subjected to a silica gel column chromatography to obtain crystals. Subsequently, the crystals obtained were recrystallized from a mixture of chloroform, methanol and ether to obtain 39 mg of the desired compound.

SYNTHESIS EXAMPLE 26

Synthesis of the exo form of 6-O-($\beta$-1-pyrrolidinylpropionyl)-3',4'-O-benzylidene-4''-epiamino-4''-deoxy-chartreusin dihydrochloride (referred to hereinafter as compound No. 36)

(1) In a mixture of 3.5 ml of anhydrous pyridine and 1.8 ml of anhydrous chloroform was dissolved 300 mg of the exo form of 3',4'-O-benzylidene-4''-(N-carbobenzyloxy-epiamino)-4''-deoxy-chartreusin (intermediate No. 536) obtained in Synthesis Example 13 above, followed by adding thereto 150 mg of $\beta$-1-pyrrolidinylpropionic acid and 290 mg of dicyclohexylcarbodiimide, and the reaction was carried out with stirring at room temperature for 15 hours.

After completion of the reaction, a small amount of methanol and ethyl acetate were added, after which the resulting mixture was filtered and the filtrate was concentrated under reduced pressure. The oily substance thus obtained was dissolved in chloroform and the resulting solution was washed successively with water, diluted hydrochloric acid and water. The chloroform solution thus washed was mixed with an equal volume or more of ethyl acetate, and then insoluble materials were collected and dissolved again in chloroform containing a small amount of methanol. The resulting chloroform solution was washed with water and then with an aqueous sodium chloride solution, dried, and then concentrated under reduced pressure to obtain 179 mg of the exo form of 6-O-($\beta$-1-pyrrolidinyl-propionyl)-3',4'-O-benzylidene-4''-(N-carbobenzyloxy-epiamino)-4''-deoxy-chartreusin in a crude form.

(2) In a mixture of 7.2 ml of tetrahydrofuran, 3.6 ml of a 0.1N aqueous hydrochloric acid solution and 1.8 ml of water was dissolved 179 mg of the exo form of 6-O-($\beta$-1-pyrrolidinyl-propionyl)-3',4'-O-benzylidene-4''-(N-carbobenzyloxy-epiamino)-4''-deoxy-chartreusin obtained in (1) above, followed by adding thereto 75 mg of 5% palladium-carbon, and the resulting mixture was subjected to reaction with stirring in a hydrogen stream (1 atmosphere) at 0° to 4° C. for 14 hours.

After completion of the reaction, the reaction mixture was filtered through Celite, after which water was added to the filtrate and the resulting solution was washed with chloroform. The organic solvent in the aqueous solution thus obtained was removed under reduced pressure, and then the residue was freeze-dried to obtain 130 mg of the desired compound.

SYNTHESIS EXAMPLE 27

Synthesis of the exo form of 6-O-{4-(5-methyl-3-phenylisoxazolyl)-carbonyl}-3',4'-O-benzylidene-chartreusin (referred to hereinafter as compound No. 14)

In a mixture of 8.2 ml of anhydrous pyridine and 6 ml of anhydrous chloroform was dissolved 600 mg of the exo form of 3',4'-O-benzylidene-chartreusin (intermediate No. 501) obtained in Synthesis Example 1 above, followed by adding thereto 500 mg of 5-methyl-3-phenylisoxazole-4-carboxylic acid and 680 mg of dicyclohexylcarbodiimide, and the resulting mixture was subjected to reaction with stirring at room temperature for 20 hours.

After completion of the reaction, post-treatment and separation were carried out in the same manner as in Synthesis Example 17 above, after which recrystallization from a mixture of chloroform, ethanol and hexane was conducted to obtain 400 mg of crystals of the disired compound.

SYNTHESIS EXAMPLE 28

Synthesis of the exo form of 6-O-(2-indolyl-carbonyl)-3',4'-O-benzylidene-chartreusin (referred to hereinafter as compound No. 17)

In a mixture of 4.1 ml of anhydrous pyridine and 2 ml of anhydrous chloroform was dissolved 300 mg of the exo form of 3',4'-O-benzylidene-chartreusin (intermediate No. 501) obtained in Synthesis Example 1 above, followed by adding thereto 199 mg of indole-2-carboxylic acid and 422 mg of dicyclohexylcarbodiimide, and the resulting mixture was subjected to reaction with stirring at room temperature for 4 hours.

After completion of the reaction, post-treatment and separation were carried out in the same manner as in Synthesis Example 17 above, after which recrystallization from a mixture of chloroform, ethanol and hexane was conducted to obtain 190 mg of crystals of the desired compound.

SYNTHESIS EXAMPLE 29

Synthesis of the exo form of 6-O-{3-(1,4-dihydro-1-ethyl-7-methyl-4-oxo-1,8-naphthyridinyl)-carbonyl}-3',4'-O-benzylidene-chartreusin (referred to hereinafter as compound No. 33)

In a mixture of 4 ml of anhydrous pyridine and 6 ml of anhydrous chloroform was dissolved 300 mg of the exo form of 3',4'-O-benzylidene-chartreusin (intermediate No. 501) obtained in Synthesis Example 1 above, followed by adding thereto 287 mg of 1,4-dihydro-1-ethyl-7-methyl-4-oxo-1,8-naphthyridine-3-carboxylic acid (Nalidixic acid) and 500 mg of dicyclohexylcarbodiimide, and the resulting mixture was subjected to reaction with stirring at room temperature for 72 hours.

After completion of the reaction, post-treatment and separation were carried out in the same manner as in Synthesis Example 17 above, after which recrystallization from a mixture of chloroform, ethanol and hexane was conducted to obtain 270 mg of crystals of the desired compound.

NMR data of typical intermediates are shown in Table 8, via which intermediate the final desired compounds were synthesized in Synthesis Examples 17 to 29 above.

After completion of the reaction, the methanol and the unreacted pyrrolidine were removed under reduced pressure, after which water was added to the residue and the resulting aqueous solution was adjusted to pH 9 to 10 with an aqueous sodium hydroxide solution. The solution thus adjusted was washed with ethyl acetate and thin adjusted to pH 1 to 2 with hydrochloric acid. The acidic aqueous solution thus obtained was washed with ethylacetate and then adjusted to pH 6.0 again with an aqueous sodium hydroxide solution. Subsequently, the weakly acidic aqueous solution thus obtained was filtered, after which the filtrate was concentrated under reduced pressure to remove water, whereby white powder was obtained. The white powder was dissolved in a mixture of ethanol and a small amount of water, and the resulting solution was filtered, after which the filtrate was concentrated under reduced pressure to obtain 280 mg of the desired compound.

NMR; (60 MHz, $\delta$ value in $CD_3OD$), 2.08 (4H, m, $-CH_2-CH_2-$), 2.54 (2H, t, J=6 Hz, $-COCH_2-$), 3.37 (6H, m,

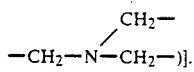].

TABLE 8

| Intermediate No. | NMR Assignment (60 MHz, δ value) | | | | | | | | | |
|---|---|---|---|---|---|---|---|---|---|---|
| | A | B | C | D | E | F | G | H* | I | J |
| Intermediate (I) of compound No. 37 | — | 1.26, 1.49 | 2.90 | 3.54 | — | 5.37 | 5.91 | 6.42 | 7.43–7.90 (10H) | $S_2$ |
| Intermediate (II) of compound No. 37 | — | 1.21, 1.48 | 2.90 | 3.51 | — | 5.30 | 5.90 | 6.36 | 7.29–7.93 (10H) | $S_1$ |
| Intermediate (I) of compound No. 39 | 1.18 | 1.29, 1.49 | 2.93 | 3.60 | — | 5.36 | 5.96 | 6.35 | 7.29–8.01 (10H) | " |
| Intermediate (II) of compound No. 39 | 1.20 | 1.29, 1.50 | 2.93 | 3.58 | — | 5.37 | 5.91 | 6.40 | 7.31–8.01 (10H) | " |
| Intermediate (I) of compound No. 34 | — | 1.17, 1.40 1.47 | 2.85 | 3.73 | 5.02 5.10 | 5.22 | 5.86 | 6.28 | 7.24–7.85 (20H) | $S_2$ |
| Intermediate (I) of compound No. 51 | — | 1.25, 1.49 | 2.92 | 3.68 3.90 | 5.10 | 5.42 | 6.01 | 6.41 | 7.37–8.08 (19H) | " |

A: (6H, d, J=7Hz, $CH_3 \times 2$),
B: (3H, d, J=7Hz, $CH_3$),
C: (3H, s, Ar—$CH_3$),
D: (3H, s, —$OCH_3$),
E: (2H, s, benzyl proton),
F: (1H, d, J=8Hz, anomer proton),
G: (1H, d, J=4Hz, anomer proton), H*: (1H, s, $-O\overset{|}{C}HO-$),
I: (aromatic proton),
J: $S_1$ = measured in $CDCl_3$, $S_2$ = measured in $CDCl_3-CD_3OD$ The amino acid, the amino acid deivatives, the carboxylic acid and the carboxylic acid derivatives of the general formula (III) are easily available or can be synthesized by a conventional process. Examples of processes for the syntheiss of these compounds are described below.

SYNTHESIS EXAMPLE 30

Synthesis of β-(1-pyrrolidinyl)-propionic acid

In 5 ml of absolute methanol were dissolved 500 mg of acrylic acid and 800 mg of pyrrolidine, and the resulting solution was subjected to reaction with stirring at room temperature for 24 hours.

The following amino acid derivative was synthesized according to Synthesis Example 30 above:

β-Morpholino-propionic acid

NMR; (60 MHz, δ values in $CD_3OD$), 2.45 (2H, t, J=6 Hz, $-COCH_2-$), 2.92–3.32 (6H, m,

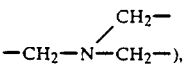

3.83 (4H, m, $-CH_2OCH_2-$).

SYNTHESIS EXAMPLE 31

Synthesis of N-trifluoroacetyl-β-amino-isobutyric acid

To 2.0 ml of trifluoroacetic anhydride was added 300 mg of β-amino-isobutyric acid in small portions, and the resulting mixture was stirred at 0° C. for 30 minutes and then subjected to reaction with stirring at room temperature for 3 hours.

After completion of the reaction, the unreacted trifluoroacetic anhydride was removed under reduced pressure, after which water was added to the residue and the resulting mixture was extracted with ethyl acetate. The ethyl acetate layer obtained was washed with an aqueous sodium chloride solution, dried, and then concentrated under reduced pressure to obtain a white crude product. Subsequently, the crude product was washed with a mixed solvent of hexane and ether and then dried to obtain 480 mg of the desired compound having a melting point of 61.0°–65.0° C.

NMR; 60 MHz, δ value in CDCl$_3$), 1.25 (3H, d, J=7 Hz, CH$_3$), 2.80 (1H, m,

3.53 (2H, t, J=7 Hz, —CH$_2$—N—), 7.47 (1H, m, —NH—), 10.97 (1H, s, —COOH).

The following amino acid derivatives were synthesized according to Synthesis Example 31 above.

N-trifluoroacetyl-β-alanine m.p. 115.0°–120.0° C.

N-trifluoroacetyl-β-amino-n-butyric acid m.p. 126.0°–130.0° C.

N-trifluoroacetyl-6-amino-n-caproic acid m.p. 88.0°–90.0° C.

N-trifluoroacetyl-8-amino-n-caprylic acid m.p. 58.0°–61.0° C.

N-trifluoroacetyl-5-amino-n-valeric acid m.p. 89.0°–92.0° C.

N-methyl-N-trifluoroacetyl-glycine

NMR; (60 MHz, δ values in CDCl$_3$), 3.22 (3H, s, N—CH$_3$), 4.17 (2H, s, —CO—CH$_2$—N—), 10.47 (1H, s, —COOH).

N-trifluoroacetyl-4-amino-n-butyric acid

NMR; (60 MHz, δ values in CDCl$_3$), 2.00 (2H, m, —CH$_2$—), 2.32 (2H, t, J=7 Hz, —CO—CH$_2$—), 3.22–3.62 (2H, m, —CH$_2$—N—).

N-trifluoroacetyl-2-amino-cyclohexanecarboxylic acid

NMR; (60 MHz, δ values in CDCl$_3$), 1.14–2.17 (8H, m, CH$_2$×4), 2.91 (1H, m, —CH—CO—), 4.11 (1H, m, —CH—N—).

SYNTHESIS EXAMPLE 32

Synthesis of N-trichloroacetyl-β-alanine

To 5.6 ml of anhydrous chloroform was dissolved 500 mg of β-alanine, and 1.3 ml of trichloroacetyl chloride was dropped thereinto with stirring at 0° C. After completion of the dropping, the resulting mixture was subjected to reaction with stirring at room temperature for 5 hours.

After completion of the reaction, water was added and the mixture thus obtained was extracted with ethyl acetate. The ethyl acetate layer obtained was washed with an aqueous sodium chloride solution and then concentrated to obtain an oily substance. The oily substance was recrystallized from a mixed solvent of ethyl acetate and hexane to obtain 270 mg of the desired compound having a melting point of 102.0°–110.5° C.

The following amino acid derivative was synthesized according to Synthesis Example 32 above.

N-benzoyl-β-amino-isobutyric acid

SYNTHESIS EXAMPLE 33

Synthesis of N-carbobenzyloxy-β-amino-isobutyric acid

In a mixture of 10 ml of pyridine and 10 ml of water was dissolved 500 mg of β-amino-isobutyric acid, and 1.5 ml of benzyloxycarbonyl chloride was dropped thereinto with stirring at 0° C. After completion of the dropping, the resulting mixture was stirring of room temperature for 3 hours, after which the pyridine was removed under reduced pressure. Then, hydrochloric acid was added to the residue, and the resulting mixture was extracted with ethyl acetate. The ethyl acetate layer obtained was washed successively with diluted hydrochloric acid, water and an aqueous sodium chloride solution, and then concentrated to obtain an oily substance. Subsequently, the oily substance was washed with a mixed solvent of ether and hexane to obtain 380 mg of the desired compound.

NMR; (60 MHz, δ values in CDCl$_3$), 1.17 (3H, d, J=7 Hz, CH$_3$), 2.69 (1H, m, —CH—), 3.36 (2H, t, J=7 Hz, —CH$_2$—N—), 5.11 (2H, s, benzyl proton), 7.30 (5H, s, aromatic proton), 9.97 (1H, s, —COOH).

The following amino acid derivatives were synthesized according to Synthesis Example 33 above:

N-carbobenzyloxy-6-amino-n-caproic acid m.p. 54.0°–56.0° C.

N-carbobenzyloxy-N-isopropyl-β-amino-isobutyric acid

NMR; (60 MHz, δ values in CDCl$_3$), 1.10 (3H×3, d, J=7 Hz, CH$_3$×3), 5.08 (2H, s, benzyl proton), 7.25 (5H, aromatic proton).

N-carbobenzyloxy-2-amino-cyclohexanecarboxylic acid

NMR; (60 MHz, δ values in CDCl$_3$), 1.11–2.17 (8H, m, CH$_2$×4), 2.34–2.91 (1H, m, —CH—CO—), 3.84–4.27 (1H, m, —CH—N<), 4.97–5.21 (2H, benzyl proton), 6.91 (1H, s, —NH—CO—), 7.27 (5H, s, aromatic proton), 10.57 (1H, s, —COOH).

SYNTHESIS EXAMPLE 34

Synthesis of N-carbobenzyloxy-α-isopropyl-β-alanine (1) In 20 ml of absolute methanol was dissolved 520 mg of metallic sodium, and 2.12 g of ethyl cyanoacetate was added thereto with stirring at room temperature, after which 4.0 g of isopropyl iodide was added dropwise over a period of 10 minutes. After completion of the dropwise addition, the resulting mixture was stirred at room temperature for 3 hours, refluxed for 1 hour, subjected to a conventional post-treatment, and then distilled under reduced pressure to obtain 2.1 g of methyl α-isopropylcyanoacetate.

NMR; (60 MHz, δ values in CDCl$_3$), 1.10 (3H, d, J=7 Hz, CH$_3$), 1.13 (3H, d, J=7 Hz, CH$_3$), 2.37 (1H, m, CH), 3.46 (1H, d, J=6 Hz, CH), 3.81 (3H, s, —COOCH$_3$).

(2) In 6.0 ml of acetic acid was dissolved 560 mg of the methyl α-isopropyl-cyanoacetate obtained in (1) above, after which 0.15 ml of concentrated sulfuric acid and 50 mg of platinum oxide (Adams catalyst) were added, and the resulting mixture was subjected to catalytic reduction in a hydrogen stream at 3 to 4 atmospheres for 4 hours.

After completion of the reaction, the reaction mixture was filtered. Then, water was added to the filtrate and the resulting mixture was concentrated under reduced pressure, after which the acetic acid was removed to obtain an oily substance. Subsequently, the oily substance was dissolved in water, and the resulting solution was neutralized with about 0.1N barium hydroxide and then filtered, after which the filtrate was concentrated under reduced pressure to obtain 570 mg of crude methyl ester of α-isopropyl-β-alanine.

(3) The crude methyl ester of α-isopropyl-β-alanine obtained in (2) above was treated according to Synthesis Example 33 above to obtain methyl ester of N-carbobenzyloxy-α-isopropyl-β-alanine.

NMR; (60 MHz, δ values in CDCl₃), 0.94 (3H×2, d, J=7 Hz, CH₃×2), 3.65 (3H, s, —COOCH₃), 5.05 (2H, s, benzyl proton), 7.28 (5H, s, aromatic proton).

(4) In a mixture of 18 ml of methanol and 2.7 ml of a 2N aqueous potassium hydroxide solution was dissolved 450 mg of the methyl ester of N-carbobenzyloxy-α-isopropyl-β-alanine obtained in (3) above, and the resulting solution was stirred at 40° to 50° C. for 5 hours.

After completion of the reaction, the reaction mixture was neutralized with diluted hydrochloric acid, after which the methanol was removed under reduced pressure, and the residue was acidified with diluted hydrochloric acid and then extracted with ethyl acetate. The ethyl acetate layer was washed with water and then with an aqueous sodium chloride solution, thereafter dried, and then concentrated under reduced pressure to obtain crude crystals. The crude crystals were recrystallized from a mixture of ethyl acetate and hexane to obtain 310 mg of the desired compound having a melting point of 75.5°–78.5° C.

NMR; (60 MHz, δ values in CDCl₃), 0.96 (3H×2, d, J=7 Hz, CH₃×2), 5.05 (2H, s, benzyl proton), 7.26 (5H, s, aromatic proton), 10.69 (1H, s, —COOH).

SYNTHESIS EXAMPLE 35

Synthesis of 3-chloropropionyloxyacetic acid

In a mixture of 5.0 ml of anhydrous pyridine and 3.0 ml of anhydrous chloroform was dissolved 2.0 g of glycolic acid, and 2.5 ml of 3-chloropropionyl chloride was added dropwise at 0° C. After completion of the dropwise addition, the resulting mixture was subjected to reaction with stirring at 30° to 35° C. for 2 hours.

After completion of the reaction, the reaction mixture was added to 300 ml of a saturated aqueous sodium chloride solution, and the resulting mixture was extracted with ethyl acetate. The ethyl acetate layer was dried, after which the solvent was removed by distillation under reduced pressure to obtain 2.8 g of the desired compound.

NMR; (60 MHz, δ values in CDCl₃), 2.89 (2H, t, J=6 Hz, —CH₂—CO—), 3.73 (2H, t, J=6 Hz, —CH₂Cl), 4.66 (2H, s, —O—CH₂—CO—), 10.81 (1H, s, —COOH).

SYNTHESIS EXAMPLE 36

Synthesis of 3-methylsulfinyl-propionic acid

In 50 ml of water was dissolved 5.4 g of sodium metaperiodate, and 3.0 g of 3-methylthiopropionic acid was added dropwise at 1° to 3° C. over a period of 20 minutes. After completion of the dropwise addition, the resulting mixture was subjected to reaction with stirring at 1° to 3° C. for 2 hours.

After completion of the reaction, the reaction mixture was filtered and the filtrate was concentrated under reduced pressure to obtain a solid. Subsequently, the solid was dissolved in 30 ml of ethanol, followed by adding thereto 3.0 g of anhydrous sodium sulfate, and the resulting mixture was stirred at room temperature for 2 hours, after which the mixture was filtered and the filtrate was concentrated under reduced pressure to obtain 3.2 g of the desired compound.

NMR; (60 MHz, δ values in CD₃OD), 2.63 (3H, CH₃SO—), 2.81 (2H, t, J=4 Hz, —CH₂—CO—), 2.96 (2H, t, J=4 Hz, —CH₂—SO—).

SYNTHESIS EXAMPLE 37

Synthesis of N,N-dimethyl-β-amino-isobutyric acid

In 1.0 ml of water was dissolved 1.5 g of methylmalonic acid, after which 1.26 g of a 50% aqueous dimethylamine solution and 0.96 ml of a 37% aqueous formaldehyde solution were added with stirring at 0° C., and the resulting mixture was stirred at 0° to 5° C. for 3 hours and then at 80° C. for 30 minutes.

After completion of the reaction, the solvent was removed under reduced pressure, after which anhydrous sodium sulfate was added to the residue, and the resulting mixture was extracted with methanol. The methanolic solution thus obtained was filtered and the filtrate was concentrated under reduced pressure to obtain a white solid. The solid was recrystallized from a mixture of methanol and acetone to obtain 610 mg of the desired compound having a melting point of 169.0°–174.0° C.

NMR; (60 MHz, δ values in D₂O, internal standard DSS), 1.14 (3H, d, J=7 Hz, CH₃), 2.86 (3H×2, s,

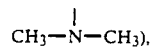

2.98 (1H, d, J=10 Hz,

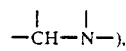

3.21 (1H, d, J=10 Hz,

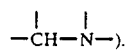

The following amino acids were synthesized according to Synthesis Example 37 above:

N,N-dimethyl-2-ethyl-β-alanine

NMR; (% C MHz, δ values in CDCl₃), 0.96 (3H, t, J=7 Hz, CH₃), 1.45–1.88 (2H, m, —CH₂—), 2.69 (3H×2, s,

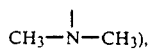

2.87 (1H, d, J=11 Hz,

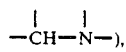

3.26 (1H, d, J=11 Hz, $$-\overset{|}{\text{CH}}-\overset{|}{\text{N}}-).$$

N-isopropyl-$\beta$-amino-isobutyric acid (used for preparing N-carbobenzyloxy-N-isopropyl-$\beta$-amino-isobutyric acid) m.p. 175.5°–176.0° C.

SYNTHESIS EXAMPLE 38

Synthesis of N-(N',N'-dimethyl-glycyl)-$\beta$-amino-isobutyric acid (1) In a mixture of 3.0 ml of dioxane and 3.0 ml of pyridine were dissolved 103 mg of N,N-dimethylglycine and 117 mg of methyl $\beta$-amino-isobutyrate, followed by adding thereto 227 mg of dicyclohexylcarbodiimide, and the resulting mixture was subjected to reaction with stirring at room temperature for 24 hours.

After completion of the reaction, the reaction mixture was filtered and the filtrate was concentrated under reduced pressure, after which the concentrate was dissolved in a small amount of water, and only the soluble fraction was concentrated under reduced pressure and dissolved in a small amount of methanol. Only the soluble fraction thus obtained was concentrated under reduced pressure to obtain 186 mg of crude methyl N-(N',N'-dimethyl-glycyl)-$\beta$-amino-isobutyrate.

(2) In a mixture of 1.0 ml of methanol and 1.0 ml of a 1.2N aqueous sodium hydroxide solution was dissolved 186 mg of the methyl ester, and the resulting solution was subjected to reaction with stirring at room temperature for 1 hour.

After completion of the reaction, the reaction mixture was neutralized with diluted hydrochloric acid and then subjected to post-treatment in the same manner as in (1) above to obtain 211 mg of crude N-(N',N'-dimethyl-glycyl)-$\beta$-amino-isobutyric acid.

The following amino acid derivative was synthesized according to Synthesis Example 38 above:

N-(N'-carbobenzyloxy-glycyl)-$\beta$-amino-irobutyric acid

NMR; (60 MHz, $\delta$ values in $CD_3Cl_3$—$CD_3OD$), 1.13 (3H, d, J=7 Hz, $CH_3$), 5.05 (2H, s, benzyl proton), 7.27 (5H, aromatic proton).

SYNTHESIS EXAMPLE 39

Synthesis of 2,2-dimethyl-4-oxo-tetrahydropyran-6-carboxylic acid

In 8 ml of tetrahydrofuran was dissolved 0.5 g of 3,4-dihydro-2,2-dimethyl-4-oxo-2H-pyran-6-carboxylic acid, followed by adding thereto 50 mg of 10% palladium-carbon, and the reaction was carried out with stirring in a hydrogen stream at room temperature for 3 hours.

After completion of the reaction, the reaction mixture was filtered through Celite, after which the filtrate was concentrated under reduced pressure to obtain 0.5 g of the desired compound in oily form.

SYNTHESIS EXAMPLE 40

Synthesis of 4-acetyloxy-2,2-dimethyl-tetrahydropyran-6-carboxylic acid

In 5 ml of absolute methanol was dissolved 0.5 g of 3,4-dihydro-2,2-dimethyl-4-oxo-2H-pyran-6-carboxylic acid, and 220 mg of sodium borohydride was added, after which the reaction was carried out with stirring at room temperature for 20 hours.

After completion of the reaction, the reaction mixture was neutralized with diluted hydrochloric acid, after which water was added and the resulting mixture was extracted with ethyl acetate. The ethyl acetate layer was washed successively with water, an aqueous sodium hydrogencarbonate solution and an aqueous sodium chloride solution dried, and then concentrated to obtain a crude reduced product.

The reduced product was dissolved as it was in 3 ml of anhydrous pyridine, and 0.5 ml of acetic anhydride was added, after which the resulting mixture was subjected to reaction with stirring at room temperature for 20 hours.

After completion of the reaction, the reaction mixture was concentrated and then subjected to a silica gel column chromatography to obtain 85 mg of the desired compound.

SYNTHESIS EXAMPLE 41

Synthesis of 3-(3,4-methylenedioxy-phenyl)-propionic acid

In 5 ml of absolute methanol was dissolved 500 mg of 3,4-methylenedioxy-cinnamic acid, followed by adding thereto 50 mg of 10% palladium-carbon, and the reaction was carried out with stirring in a hydrogen stream at room temperature for 5 hours.

After completion of the reaction, the reaction mixture was filtered and the filtrate was concentrated under reduced pressure to obtain a crude product. The crude product was recrystallized from methanol to obtain 285 mg of the desired compound.

NMR; (60 MHz, $\delta$ values in $CDCl_3$), 2.71 (4H, —$CH_2$—$CH_2$—), 5.82 (2H, s, —O—$CH_2$—O—), 6.57 (3H, aromatic proton).

Specific examples of the compounds included in this invention are described below. General formula (I):

TABLE 9

| Compound No. | X₁ | X₂ | X₃ | X₄ | X₅ | X₆ | X₇ | X₈ | Isomer | Q¹⁾ | Salt | Melting point (°C.) |
|---|---|---|---|---|---|---|---|---|---|---|---|---|
| 1 | H | Phenyl | H | H | OH | H | H | OH | Exo | -(2-pyrrolyl) | — | 193.0–200.0 |
| 2 | " | " | " | " | " | " | " | " | Exo | -(2-pyrrolyl)CH₃(1) | — | 181.0–185.0 |
| 3 | CH₃ | CH₃ | " | " | " | " | " | " | — | -(2-pyrrolidinyl)CBZ(1) | — | 161.0–165.0 |
| 4 | H | Phenyl | " | " | " | " | " | " | Exo | -(2-pyrrolidinyl)-COCH₂NHCOCH₂NHCBZ(1) | — | 163.0–169.0 |
| 5 | CH₃ | CH₃ | " | " | " | " | " | " | — | -(2-furyl) | — | 185.0–195.0 |
| 6 | H | Phenyl | " | " | " | " | " | " | Exo | " | — | 190.0–195.0 |
| 7 | CH₃ | CH₃ | " | " | " | " | " | " | — | -(3-furyl) | — | 184.0–192.0 |
| 8 | " | " | " | " | " | " | " | " | — | -(2-furyl)Br(5) | — | 182.0–192.0 |
| 9 | " | " | " | " | " | " | " | " | — | —CH=CH—(2-furyl) | — | 182.0–188.0 |
| 10 | " | " | " | " | " | " | " | " | — | -(2-thienyl) | — | 186.0–195.0 |
| 11 | H | Phenyl | " | " | " | " | " | " | Exo | " | — | 186.0–191.0 |
| 12 | CH₃ | CH₃ | " | " | " | " | " | " | — | -(2-thienyl)CH₃(5) | — | 180.0–186.0 |
| 13 | " | " | " | " | " | " | " | " | — | —CH₂(2-thienyl) | — | 195.0–202.0 |
| 14 | H | Phenyl | H | H | OH | H | H | OH | Exo | -(4-isoxazolyl)CH₃(5)phenyl(3) | — | 178.0–182.0 |
| 15 | " | " | " | " | " | " | " | " | " | —(CH₂)₄{3-(1,2-ditiolanyl)} | — | 183.0–186.0 |
| 16 | " | " | " | " | " | " | " | " | " | —CH=CH—(4-imidazolyl) | — | 213.0–216.0 |
| 17 | " | " | " | " | " | " | " | " | " | -(2-indolyl) | — | 198.0–204.0 |
| 18 | " | " | " | " | " | " | " | " | " | -(5-indolyl) | — | 215.0–220.0 |
| 19 | " | " | " | " | " | " | " | " | " | -(2-indoyl)OCH₃(5) | — | 202.0–206.0 |
| 20 | " | " | " | " | " | " | " | " | " | —CH₂(3-indolyl) | — | 181.0–185.0 |
| 21 | " | " | " | " | " | " | " | " | Mixture | —CH=CH—(phenyl)methylenedioxy(3,4) | — | 186.0–191.0 |
| 22 | " | " | " | " | " | " | " | " | Exo | —(CH₂)₂—(phenyl)methylenedioxy(3,4) | — | 177.0–183.0 |
| 23 | CH₃ | CH₃ | | | | | | | — | -(4-piperidyl)COCF₃(1) | — | 173.5–176.5 |
| 24 | H | Phenyl | " | " | " | " | " | " | Exo | -(3-piperidyl)CH₃(1) | — | 196.0–204.0 |
| 25 | " | " | " | " | " | " | " | " | " | -(3-piperidyl)NHCOCF₃(2) | — | 202.0–205.0 |
| 26 | " | " | " | " | " | " | " | " | " | -(2-tetrahydropyranyl)OAc(4)(CH₃)₂(6,6) | — | 199.0–202.0 |
| 27 | CH₃ | CH₃ | H | H | OH | H | H | OH | — | -(2-quinolyl) | — | 208.0–216.0 |
| 28 | H | Phenyl | " | " | " | " | " | " | Exo | -(4-quinolyl)phenyl(2) | — | 192.0–196.0 |
| 29 | " | " | " | " | " | " | " | " | " | —CH₂(phenyl)methylenedioxy(3,4) | — | 178.0–181.0 |
| 30 | " | m-Fluorophenyl | " | " | " | " | " | " | Endo | -(2-indolyl) | — | 204.0–208.0 |
| 31 | " | m-Bromophenyl | " | " | " | " | " | " | " | -(2-pyrrolyl) | — | 191.0–194.0 |
| 32 | " | Phenyl | " | " | " | " | " | " | Exo | -{2-(4-oxo-tetrahydropyranyl)}(CH₃)₂(6,6) | — | 197.0–201.0 |
| 33 | " | " | " | " | " | " | " | " | " | -{3-(1,4-dihydro-4-oxo-1,8-naphthyridinyl)}C₂H₅(1)CH₃(7) | — | 203.0–205.0 |
| 34 | " | " | " | " | " | " | NH₂ | H | Exo | —CH(CH₃)(CH₂NH₂) 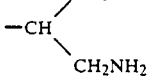 | 2HCl | 186.0–190.0 |
| 35 | " | " | " | " | " | " | " | " | " | —(CH₂)₂OCH₂CH₃ | — | 182.0–185.0 |
| 36 | " | " | " | " | " | " | " | " | " | —(CH₂)₂—(1-pyrrolidinyl) | 2HCl | 195.0–199.0 |
| 37 | H | Phenyl | H | H | OH | H | NH₂ | H | Exo | —(CH₂)₅NHCOCF₃ | HCl | 181.0–183.0 |
| 38 | " | m-Bromophenyl | " | " | " | " | " | " | Endo | —(CH₂)₂NHCHO | — | 167.0–172.0 |
| 39 | " | Phenyl | " | " | " | " | " | " | Exo | —CH₂CH(CH₃)₂ 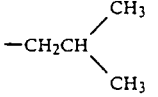 | HCl | 205.0–210.0 |
| 40 | " | " | " | " | " | " | " | " | " | —CH(CH₃)(CH₂NHCOCF₃) 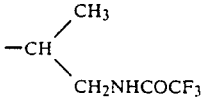 | " | 195.0–209.0 |
| 41 | " | " | " | " | " | " | " | " | " | —CH₂CH(CH₃)(NHCOCF₃) 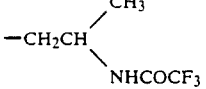 | " | 267.0–270.0 |
| 42 | " | " | " | " | " | " | " | " | " | —(CH₂)₂NHCHO | " | 187.0–190.0 |

TABLE 9-continued

| Compound No. | X₁ | X₂ | X₃ | X₄ | X₅ | X₆ | X₇ | X₈ | Isomer | Q[1] | Salt | Melting point (°C.) |
|---|---|---|---|---|---|---|---|---|---|---|---|---|
| 43 | " | " | " | " | " | " | " | " | " | $-(CH_2)_2NHCH_3$ | 2HCl | 189.0–193.0 |
| 44 | " | " | " | " | " | " | " | " | " | $-CH\begin{smallmatrix}CH_3\\CH_2-NHCH_3\end{smallmatrix}$ | " | 156.0–161.0 |
| 45 | " | " | " | " | " | " | " | " | " | $-CH\begin{smallmatrix}CH(CH_3)_2\\CH_2NH_2\end{smallmatrix}$ | " | 205.0–211.0 |
| 46 | " | " | " | " | " | " | " | " | " | $-(CH_2)_2NHCOCH_2NH_2$ | " | 165.0–168.0 |
| 47 | " | " | " | " | " | " | " | " | " | $-CH_2OCO\text{-(phenyl)}$ | — | 143.0–147.0 |
| 48 | H | Phenyl | H | H | OH | H | NH₂ | H | Exo | $-(CH_2)_2COCH_3$ | HCl | 192.0–199.0 |
| 49 | " | " | " | " | " | " | " | " | " | -(cyclopropyl)CH₃(2) | — | 167.0–169.0 |
| 50 | " | " | " | " | " | " | " | " | " | $-(CH_2)\text{(phenyl)}$ | — | 197.0–202.0 |
| 51 | " | " | " | " | " | " | " | " | " | -(phenyl) OCH₃(m) | — | 163.0–165.0 |
| 52 | " | " | " | " | " | " | " | " | " | -(phenyl) Cl(p) | — | 184.0–186.0 |
| 53 | " | " | " | " | " | " | " | " | " | -(phenyl) CF₃(m) | — | 172.0–175.0 |
| 54 | " | " | " | " | " | " | " | " | " | $-(CH_2)_4CH_3$ | — | 208.0–213.0 |
| 55 | " | m-Fluoro-phenyl | " | " | " | " | " | " | Endo | $-(CH_2)_2NHCO\text{-(phenyl)}$ | — | 158.0–163.0 |
| 56 | CH₃ | CH₃ | " | " | " | " | " | " | — | $-CH\begin{smallmatrix}CH_3\\CH_2NHCOCF_3\end{smallmatrix}$ | HCl | 189.0–193.0 |
| 57 | H | Phenyl | " | " | " | " | " | " | Exo | -(2-indolyl) | — | — |
| 58 | " | " | " | " | " | " | " | " | " | -(4-isoxazolyl)CH₃(5)-phenyl(3) | — | — |
| 59 | " | " | " | " | " | " | " | " | " | -{3-(1,4-dihydro-4-oxo-1,8-naphthyridinyl)}C₂H₅(1)CH₃(7) | — | — |
| 60 | H | Phenyl | H | H | OH | H | H | OH | Exo | -(2-pyrrolyl)COCH₂NH₂(1) | HCl | — |
| 61 | " | " | " | " | " | " | " | " | " | -(2-pyrrolidinyl)-COCH₂NHCOCH₂NH₂(1) | " | — |
| 62 | CH₃ | CH₃ | " | " | H | OH | " | " | — | -(2-thienyl) | — | 177.0–181.0 |
| 63 | H | Phenyl | " | " | " | " | " | " | Exo | " | — | — |
| 64 | " | " | " | " | " | " | " | " | " | -(2-indolyl) | — | — |
| 65 | " | " | " | " | " | " | " | " | " | -(4-isoxazolyl)-CH₃(5)phenyl(3) | — | — |
| 66 | " | " | " | " | " | " | " | " | " | -{3-(1,4-dihydro-4-oxo-1,8-naphthyridinyl)}-C₂H₅(1)CH₃(7) | — | — |
| 67 | " | " | " | " | " | " | " | " | " | $-CH_2CH\begin{smallmatrix}CH_3\\CH_3\end{smallmatrix}$ | — | — |
| 68 | " | " | " | " | " | " | " | " | " | $-(CH_2)_2COCH_3$ | — | — |
| 69 | " | " | " | " | " | " | " | " | " | $-CH\begin{smallmatrix}CH_3\\CH_2-NH_2\end{smallmatrix}$ | HCl | — |
| 70 | " | " | " | " | " | " | " | " | " | $-(CH_2)_2NHCO\text{-phenyl}$ | — | — |
| 71 | H | Phenyl | H | H | H | OH | H | OH | Exo | $-CH\begin{smallmatrix}CH_3\\CH_2NHCOCF_3\end{smallmatrix}$ | — | — |
| 72 | " | " | " | " | OH | H | " | " | " | -(4-thiazolidinyl)CBZ(3) | — | — |
| 73 | " | " | " | " | " | " | " | " | " | -(4-thiazolidinyl) | HCl | — |
| 74 | " | " | " | " | " | " | " | " | " | -{4-(2,6-dioxo-1,2,3,6-tetrahydropyrimidinyl)} | — | — |
| 75 | " | " | " | " | " | " | " | " | " | $-CH_2$(3-indolyl)-CH₃(2)OCH₃(5)-(4-chlorobenzoyl)(1) | — | — |

TABLE 9-continued

| Compound No. | X₁ | X₂ | X₃ | X₄ | X₅ | X₆ | X₇ | X₈ | Isomer | Q¹⁾ | Salt | Melting point (°C.) |
|---|---|---|---|---|---|---|---|---|---|---|---|---|
| 76 | " | " | " | " | " | " | " | " | " | -{5-(2-oxopyranyl)} | — | — |
| 77 | " | " | " | " | " | " | " | " | " | -(2-indolyl)Cl(5) | — | — |
| 78 | " | " | " | " | " | " | " | " | " | —CH₂(2-indolyl)Br(5) | — | — |
| 79 | " | " | " | " | " | " | " | " | " | -{6-(5,8-dihydro-5-oxopyrido[2,3-d]pyrimidinyl)}(2-pyrrolidinyl)-(2)C₂H₅(8) | — | — |
| 80 | " | " | " | " | " | " | " | " | " | -{6-(5,8-dihydro-5-oxopyrido[2,3-d]pyrimidinyl)}{1-(4-methyl-piperazinyl)}(2)C₂H₅(8) | — | — |
| 81 | H | Phenyl | H | H | OH | H | H | OH | Exo | -{3-(1,4-dihydro-4-oxo-1,8-naphtyridinyl)}-C₂H₅(1)F(6)(1-piperazinyl)(7) | — | — |
| 82 | " | " | " | " | " | " | " | " | " | -(4-quinolyl) | — | — |
| 83 | " | " | " | " | " | " | " | " | " | -(3-quinolyl) | — | — |
| 84 | " | " | " | " | " | " | " | " | " | -(2-quinoxalyl) | — | — |
| 85 | " | " | " | " | " | " | " | " | " | -{6-(5,8-dihydro-5-oxopyrido[2,3-d]-pyrimidinyl}NHCOCF₃-(2)C₂H₅(8) | — | — |
| 86 | CH₃ | CH₃ | " | " | —O— | " | " | " | — | —(CH₂)₂NHCO(phenyl) | — | 154.0–160.0 |
| 87 | " | " | " | " | " | " | " | " | — | —CH₂CH(CH₃)CH₃ 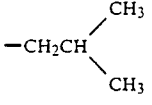 | — | 254.0–257.0 |
| 88 | " | " | " | CH₃ | OH | H | " | " | — | -(2-thienyl) | — | 192.0–195.0 |
| 89 | H | Phenyl | " | " | " | " | " | " | Exo | -{3-(1,4-dihydro-4-oxo-1,8-naphthyridinyl)}C₂H₅(1)CH₃(7) | — | — |
| 90 | " | " | " | " | " | " | " | " | " | -(2-indolyl) | — | — |
| 91 | " | " | " | " | " | " | " | " | " | —(CH₂)₂COCH₃ | — | — |
| 92 | H | Phenyl | H | CH₃ | OH | H | H | OH | Exo | —CH(CH₃)CH₂NH₂ 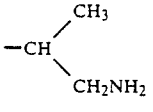 | HCl | — |
| 93 | " | " | " | " | " | " | " | " | " | —(CH₂)₂NHCH₃ | " | — |
| 94 | " | " | " | " | " | " | " | " | " | -(4-isoxazolyl)-CH₃(5)phenyl(3) | — | — |
| 95 | " | " | " | " | NH₂ | " | " | " | " | -(4-isoxazolyl)-CH₃(5)phenyl(3) | — | — |
| 96 | " | " | " | " | " | " | " | " | " | -{3-(1,4-dihydro-4-oxo-1,8-naphthyridinyl)}-C₂H₅(1)CH₃(7) | — | — |
| 97 | " | " | " | " | " | " | " | " | " | -(2-indolyl) | — | — |
| 98 | " | " | " | " | " | " | " | " | " | —(CH₂)₂NHCH₃ | 2HCl | — |
| 99 | " | " | " | " | " | " | " | " | " | —CH(CH₃)CH₂NHCOCF₃ 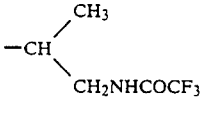 | HCl | — |
| 100 | " | " | " | " | " | " | " | *" | " | —CH₂CH(CH₃)CH₃ 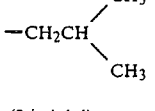 | " | — |
| 101 | " | " | " | H | OH | " | " | " | " | -(2-indolyl)-benzyloxy(5) | — | 181.0–183.0 |
| 102 | H | Phenyl | H | H | OH | H | H | OH | Exo | -(2-indolyl)hydroxy(5) | — | 199.0–201.0 |
| 103 | " | " | " | " | " | " | " | " | " | -(5-oxazolyl)CH₃(4) | — | 196.0–197.0 |
| 104 | " | " | " | " | " | " | " | " | " | —(CH₂)₃-(3-indolyl) | — | 166.0–168.0 |
| 105 | " | " | " | " | " | " | " | " | " | -{6-(5,8-dihydro-5-oxopyrido[2,3-d]pyrimidinyl}(1-pyrrolidinyl)(2)-C₂H₅(8) | — | 215.0–217.0 |
| 106 | " | " | " | " | " | " | " | " | " | -{6-(5,8-dihydro-5-oxopyrido[2,3-d]pyrimidinyl}(1-piperazinyl)(2)-C₂H₅(8) | HCl | 218.0–221.0 |
| 107 | CH₃ | CH₃ | " | " | " | " | " | " | — | -{3-(1,4-dihydro-4-oxo- | — | 208.0–210.0 |

TABLE 9-continued

| Compound No. | X₁ | X₂ | X₃ | X₄ | X₅ | X₆ | X₇ | X₈ | Isomer | Q¹⁾ | Salt | Melting point (°C.) |
|---|---|---|---|---|---|---|---|---|---|---|---|---|
| 108 | H | Phenyl | " | " | " | " | " | " | Endo | 1,8-naphthyridinyl)}-C₂H₅(1)CH₃(7)-{3-(1,4-dihydro-4-oxo-1,8-naphthyridinyl)}-C₂H₅(1)CH₃(7) | — | 207.0–209.0 |
| 109 | " | " | " | " | " | " | " | " | Exo | -(2-furyl)NHCBZ(5) | — | 188.0–189.0 |
| 110 | " | " | " | " | " | " | " | " | " | -(2-furyl)NH₂(5) | HCl | 206.0–209.0 |
| 111 | " | " | " | " | " | " | " | " | " | -(2-thienyl)NH(CH₃)₂(5) | HCl | — |
| 112 | " | " | " | " | " | " | " | " | " | -(2-furyl)N⊕H(CH₃)₃(5) | I⊖ | — |
| 113 | H | Phenyl | H | H | OH | H | NH₂ | H | Exo | —CH₂N⊕(CH₃)₃ | I⊖, HCl | — |
| 114 | " | " | " | " | " | " | " | " | " | -(2-thienyl)NHCH₃(5) | 2HCl | — |
| 115 | " | " | " | CH₃ | NH₂ | " | H | OH | " | —CH₂N⊕(CH₃)₃ | I⊖, HCl | — |
| 116 | " | " | " | " | " | " | " | " | " | -(2-furyl)NH₂(5) | 2HCl | — |
| 117 | " | " | " | H | OH | " | " | " | " | -(2-thienyl)NHCH₃(5) | HCl | — |

Note:
¹⁾The symbols (5) and (3) in -(4-isoxazolyl)CH₃(5)phenyl(3) of the compound No. 14 indicate that the isoxazolyl group is substituted by a metal group in the 5-position and by a phenyl group in the 3-position. The symbol (m) in -(phenyl)OCH₃(m) of the compound No. 51 indicates that the phenyl group is substituted by a OCH₃ group in the m-position. The other symbols are interpreted according to the above.

Next, NMR data of typical compounds of the above-mentioned compounds of this invention are shown below.

TABLE 10

| Compound No. | A | B | C | D | E | F | G | H* | Others (or remarks) | I |
|---|---|---|---|---|---|---|---|---|---|---|
| 2 | 1.30 | 1.46 | 2.85 | 3.40 | 5.33 | 5.92 | 6.35 | 6.20–8.08 (13H) | 3.93 (3H, s, N—CH₃) H* includes the prolyl group | S₁ |
| 3 | — | — | 2.82 | 3.39 | — | — | — | 7.13–8.26 (10H) | 1.16–1.80 (16H, CH₃ × 4, CH₃ × 2) 5.17 (2H, s, benzyl proton) 5.20–5.82 (4H, anomer proton × 2) | S₁ |
| 6 | 1.28 | 1.45 | 2.79 | 3.30 | 5.24 | 5.79 | 6.24 | 6.46–8.08 (13H) | H* includes the furyl group | S₁ |
| 8 | — | — | 2.90 | 3.45 | 5.25 | 5.90 | — | 6.65–8.15 (7H) | 1.30–1.89 (12H, CH₃ × 4) H* includes the furyl group | S₁ |
| 11 | 1.29 | 1.48 | 2.83 | 3.38 | 5.30 | 5.88 | 6.30 | 6.89–8.26 (13H) | H* includes the thienyl group | S₂ |
| 14 | 1.29 | 1.43 | 2.93 | 3.35 | 5.23 | 5.89 | 6.28 | 6.21–7.92 (15H) | 2.89 (3H, s, CH₃) | S₁ |
| 17 | 1.27 | 1.42 | 2.84 | 3.36 | 5.19 | 5.90 | 6.21 | 6.91–8.00 (15H) | — | S₁ |
| 18 | 1.37 | 1.40 | 2.82 | 3.42 | 5.20 | 5.96 | — | 6.92–8.70 (15H) | — | S₁ |
| 19 | 1.37 | 1.58 | 2.90 | 3.43 | 5.25 | 5.99 | 6.28 | 6.67–8.08 (14H) | 3.84 (3H, s, O—CH₃) | S₁ |
| 24 | — | — | 2.91 | 3.44 | 5.34 | 5.93 | 6.38 | 7.10–8.69 (10H) | 1.34–2.12 (2H × 4, CH₃ × 2) 2.95 (3H, s, N—CH₃) | S₁ |
| 25 | 1.37 | 1.55 | 2.89 | 3.42 | 5.30 | 5.95 | 6.46 | 6.50–8.67 (13H) | — | S₁ |
| 30 | 1.14 | 1.45 | 2.87 | 3.39 | 5.28 | 5.72 | 5.91 | 7.16–7.89 (14H) | — | S₁ |
| 33 | — | — | 2.91 | 3.42 | 5.32 | 6.00 | — | 7.30–8.63 (13H) | 1.15–1.69 (9H, CH₃ × 3) 2.70 (3H, s, Ar—CH₃) | S₁ |
| 62 | — | — | 2.86 | 3.33 | 5.11 | — | — | 7.20–8.20 (8H) | 1.28–1.61 (9H, CH₃ × 3) 1.61 (3H, s) 5.93 (d, J=0–1Hz, anomer proton) H* includes the thienyl group | S₁ |
| 86 | 1.42 | 1.50 | 2.83 | 3.46 | 5.02 | — | — | 7.23–8.00 (10H) | 1.10 (3H, s), 1.72 (3H, s) 5.67 (1H, d, J=2Hz) 6.03 (1H, s, anomer proton) | S₁ |
| 87 | 1.42 | 1.50 | 2.82 | 3.47 | 5.02 | — | — | 7.17–8.97 (5H) | 1.14 (6H, d, J=7Hz, CH₃ × 2) 1.42 (3H, s), 1.72 (3H, s), 5.67 (1H, d, J=2Hz), 6.03 (1H, s, anomer proton) | S₁ |
| 88 | — | — | 2.91 | 3.44 | 5.23 | 5.84 | — | 7.06–8.23 (8H) | 1.26–1.56 (3H × 2, CH₃ × 2) 1.43 (3H, s), 1.46 (3H, s), 1.73 (3H, s) | S₁ |

TABLE 10-continued

| Compound No. | NMR Assignement (60 MHz, δ value) | | | | | | | | |
|---|---|---|---|---|---|---|---|---|---|
| | A | B | C | D | E | F | G | H* | Others (or remarks) | I |
| | | | | | | | | | H* includes the thienyl group | |

Explanation of Table 10
A: (3H, d, J=7Hz, —CH₃), B: (3H, d, J=7Hz, —CH₃), C: (3H, s, Ar—CH₃), D: (3H, s, —O—CH₃), E: (1H, d, J=8Hz, anomer proton), F: (1H, d, J=4Hz, anomer proton), G: (1H, s, —O—CH—O—),
H*: (aromatic proton) I: $S_1$ = measured in $CDCl_3$, $S_2$ = measured in $CDCl_3$—$CD_3OD$ As shown in the experimental examples hereinafter described, the compounds of this invention have excellent antitumor activity in mice implanted with p-388 leukemia cells, L-1210 leukemia cells, and B-16 melanoma cells.

The antitumor activity, acute toxicity, dose and administration routes of the compounds of this invention are described below.

(1) Antitumor activity (1-1) Antitumor activity against P-388 leukemia cells $BDF_1$ mice were implanted intraperitoneally with P-388 leukemia cells at a rate of $1 \times 10^6$ cells/mouse, and each drug to be tested was administered intravenously on the first, fifth and ninth days, or on the first and fifth days after the implantation. Whether the mice were alive or dead was observed for 30 days. The T/C (%) was calculated based on the following equation:

$$T/C\ (\%) = \frac{MST^* \text{ of treated group}}{MST \text{ of control group}} \times 100$$

(*MST is median survival time (days))

The results obtained are shown in Table 11.

The drugs tested were as follows: solutions prepared by dissolving each of compound Nos. 34, 36 and 43 to 46 in physiological saline; suspension or solutions prepared by dissolving each of compound Nos. 35, 38 and 49 to 55 in dimethylacetamide, followed by adding thereto a small amount of a surface active agent (e.g., Tween-80) and then physiological saline; and suspension or solutions prepared by mixing each of the other compounds and a small amount of a surface active agent (e.g., Tween-80), followed by adding thereto physiological saline.

TABLE 11

| Compound No. | Dose¹⁾ (mg/kg) | T/C of MST (%) |
|---|---|---|
| 1 | b' | 154 |
| | c' | 188 |
| 2 | b | 189 |
| | c | 230 |
| 3 | c | 139 |
| | f | 195 |
| 4 | b | 138 |
| 5 | f | 217 |
| 6 | b | 199 |
| | c | 217 |
| 7 | c | 149 |
| | f | 194 |
| 8 | f | 178 |
| 9 | f | 194 |
| 10 | c | 162 |
| | f | 207 |
| 11 | b | 217 |
| | c | |
| 12 | f | 194 |
| 13 | c | 134 |
| | f | 182 |
| 14 | b | 207 |
| | c | 250 |

TABLE 11-continued

| Compound No. | Dose¹⁾ (mg/kg) | T/C of MST (%) |
|---|---|---|
| 15 | b | 153 |
| | c | 201 |
| 16 | c | 148 |
| 17 | b | 199 |
| | c | 255 |
| 18 | b | 167 |
| | c | 242 |
| 19 | b | 131 |
| | c | 165 |
| 20 | b | 148 |
| | c | 286 |
| 21 | b | 131 |
| | c | 176 |
| 22 | b | 142 |
| | c | 222 |
| 23 | c | 127 |
| 24 | b' | 152 |
| | c' | 186 |
| 25 | c | 187 |
| 27 | c | 142 |
| | f | 192 |
| 28 | b | 197 |
| 29 | b | 201 |
| | c | 255 |
| 30 | f | 142 |
| 31 | c | 128 |
| 32 | b' | 185 |
| | c' | 213 |
| 33 | b | 218 |
| | c | 274 |
| 34 | b | 140 |
| | c | 219 |
| 35 | b | 188 |
| | c | 244 |
| 36 | b | 168 |
| 37 | b | 148 |
| | c | 191 |
| 38 | f | 133 |
| 39 | c | 207 |
| | e | 240 |
| 40 | b | 142 |
| | c | 219 |
| 41 | c | 187 |
| 42 | b | 130 |
| | c | 199 |
| 43 | b | 150 |
| | c | 230 |
| 44 | b | 138 |
| | c | 148 |
| 45 | j | 131 |
| 46 | c | 148 |
| 48 | b | 166 |
| | c | 219 |
| 49 | c' | 153 |
| 50 | b' | 165 |
| | c' | 208 |
| 51 | b | 185 |
| | c | 244 |
| 52 | b | 167 |
| 53 | b | 131 |
| | c | 165 |
| 54 | b' | 165 |
| 55 | f | 133 |
| 56 | f | 138 |
| 62 | f | 131 |
| 101 | e | 191 |

TABLE 11-continued

| Compound No. | Dose[1] (mg/kg) | T/C of MST (%) |
|---|---|---|
| 102 | e | 256 |
| 103 | e | 236 |
|  | j | 210 |
| 104 | e | 256 |
|  | j | 219 |
|  | b | 185 |
| 105 | e | 256 |
|  | j | 165 |
| 106 | e | 244 |
|  | j | 188 |
| 107 | f | 134 |
| 108 | f | 158 |

Note:
[1]Symbols a to j denote the following doses:
a: 10 mg/kg/d × 3
b: 20 mg/kg/d × 3
c: 40 mg/kg/d × 3
d: 50 mg/kg/d × 3
e: 60 mg/kg/d × 3
f: 80 mg/kg/d × 3
g: 100 mg/kg/d × 3
h: 120 mg/kg/d × 3
i: 160 mg/kg/d × 3
j: 30 mg/kg/d × 3
b': 20 mg/kg/d × 2
c': 40 mg/kg/d × 2

For comparison, the same treatment as described above was carried out using, at a dose of 50 mg/ml/day×3, a chartreusin suspension, which was prepared by the preparation method described in "Cancer Research, Vol. 37, p. 1666–1672 (1977)" [a method comprising dissolving chartreusin in a mixed solution of 0.2M Na$_2$HPO$_4$ and N,N-dimethylacetamide (4:1 by volume) at a concentration of 5 mg/ml]. In this case, T/C (%) was calculated as 105%.

(1-2) Antitumor activity against L-1210 leukemia cells

BDF$_1$ mice were implanted intraperitoneally with L-1210 leukemia cells at a rate of 1×10$^5$ cells/mouse, and each drug to be tested was administered intravenously on the first, fifth and ninth days after the implantation. Whether the mice were alive or dead was observed for 30 days. The T/C (%) was calculated in the same manner as aforementioned (1-1). The results obtained are shown in Table 12.

The drugs tested were suspensions or solutions which prepared by mixing each compound to be tested and a small amount of a surface active agent (e.g., Tween-80), followed by adding thereto physiological saline.

TABLE 12

| Compound No. | Dose (mg/kg) | T/C (%) of MST |
|---|---|---|
| 2 | 40 × 3 | 243 |
| 10 | 80 × 3 | 140 |
| 14 | 40 × 3 | 208 |
| 17 | 40 × 3 | 181 |

(1-3) Antitumor activity against B-16 melanoma

BDF$_1$ mice were implanted intraperitoneally with a B-16 melanoma cell suspension in an amount of 0.5 ml/mouse, and each drug to be tested was administered intravenously on the first, fifth and ninth days after the implantion. Whether the mixe were alive or dead was observed for 60 days. The T/C (%) was calculated in the same manner as aforementioned (1-1). The results obtained are shown in Table 13.

The B-16 melanoma cell suspension was prepared as follows. Tumor fragment, maintained by subcutaneous passages in C57BL/6 mice, were aseptically removed and passed through a sterile stainless-steel mesh. Thus obtained tumor was dispersed in a culture medium or physiological saline in an amount of 9 ml per 1 g of tumor. The drugs tested were suspensions or solutions which prepared by mixing each compound to be tested and a small amount of a surface active agent (e.g., Tween-80), followed by adding thereto physiological saline.

TABLE 13

| Code No. | Compound No. | Dose (mg/kg) | T/C (%) of MST |
|---|---|---|---|
| 403 | 2 | 60 × 3 | 141 |
| 269 | 6 | 60 × 3 | 159 |
| 270 | 11 | 60 × 3 | 143 |
| 405 | 14 | 60 × 3 | 143 |
| 429 | 17 | 60 × 3 | 141 |
| 434 | 33 | 40 × 3 | 142 |

(1-4) Intestinal excretion percentage of drugs

Each drug to be tested was administered to DDY mice intravenously at a dose of 40 mg/kg-b.w., and after 2 hours, contents of the small intestine and the large intestine and feces were extracted with a mixed solvent of chloroform and methanol. The extract was concentrated and each compound to be tested was quantitatively determined by high-speed liquid chromatography. The results obtained are shown in Table 14.

The drug tested was solution which prepared by dissolving the compound No. 17 in a small amount of dimethylacetoamide, followed by adding thereto a small amount of a surface active agent (e.g., Tween-80) and physiological saline.

TABLE 14

| Compound No. | Intestinal excretion percentage (%) [(total amount of excretion/dose) × 100] |
|---|---|
| 17 | 5.4 |
| Chartreusin | 37.6 |

Results similar to that obtained for compound 17 are obtained for other compounds in this invention.

(2) Acute toxicity

In Table 15 are shown acute toxicity values (LD$_{50}$, mg/kg) in day mice in the case of intravenously administering (once) each of the compounds of this invention in the form of preparations shown in the Preparation Examples shown in Table 16.

TABLE 15

| Compound No. | Preparation Example No. | LD$_{50}$ (mg/kg) |
|---|---|---|
| 4, 26 | 2 | 20 or more |
| 28 | 1 |  |
| 36 | 8 |  |
| 52 | 6 |  |
| 45 | 8 | 30 or more |
| 1, 31, 33, 37, 40, 41, 42, 48 | 1 | 40 or more |
| 15, 16, 18, 19, 20, 21, 22, 24, 25, 29, 32 | 2 |  |
| 23 | 3 |  |
| 35, 49, 51, 53 | 6 |  |
| 34, 43, 44, 46 | 8 |  |
| 50, 54 | 7 |  |
| 2, 6, 11, 101, 103, 104, 105 | 2 | 60 or more |
| 14, 17, 102, 106 | 1 |  |
| 39 | 9 |  |
| 5, 10, 107, 108 | 4 | 80 or more |
| 7, 8, 9, 12, 13 | 3 |  |

TABLE 15-continued

| Compound No. | Preparation Example No. | LD$_{50}$ (mg/kg) |
|---|---|---|
| 30, 62 | 2 | |
| 27 | 5 | |
| 38, 55 | 6 | |
| 56 | 1 | |
| 3 | 3 | 160 or more |

(3) Dose and administration routes

As to administration routes in the case of animals, the compounds of this invention are administered as injections such as intraperitoneal injection, intravenous injection, local injection and the like, or as oral drugs. In the case of human beings, said compounds are administered as injections such as intravascular (intravenous or intraarterial) injection, local injection and the like, or as oral drugs, suppositories or the like. As to the dose, said compounds can be administered continuously or intermittently in a range in which the total dose does not exceed a certain level, in consideration of the results of animal experiments and various conditions. However, the dose may, of course, be properly varied depending on the administration route, and on the conditions of a patient or an animal to be treated (for example, age, body weight, sex, sensitivity, food and the like), interval of administration, drugs used in combination with said compounds and the degree of disease. An optimum dose and the number of administrations under certain conditions should be determined by medical specialists.

The antitumorous composition of this invention are prepared in the same manner as for conventional drugs. For example, they are prepared from an active ingredient and various pharmacologically acceptable adjuvants such as inactive diluent and the like. Intravenous administration of these antitumorous compositions is most suitable.

The content of active ingredient in the antitumorous compositions of active ingredient in the antitumorous compositions of this invention may vary depending on various conditions and cannot be determined uniquely. It is sufficient that the active ingredient is contained similarly to the case of conventional antitumorous compositions. For example, the active ingredient may be contained in an amount of at least 0.001%.

Next, Preparation Examples of the antitumorous compositions of this invention are shown in Table 16.

TABLE 16

| Preparation Example No. | Active ingredient | | Active surface agent | | Using amount of physiological saline (ml) | Condition (Note 1) |
|---|---|---|---|---|---|---|
| | Compound No. | Using amount (mg) | Using amount of Tween-80 (ml) | Others | | |
| 1 | 1 | 5.2 | 0.10 | — | 2.5 | Soln. |
| 2 | 2 | " | " | — | " | Sus. |
| 3 | 3 | 16 | 0.16 | — | 2.0 | " |
| 4 | 5 | " | 0.24 | — | 1.8 | " |
| 5 | 27 | " | " | — | " | Soln. |
| 6 | 35 | 5.2 | 0.1 | Dimethylacetamide 0.25 ml | 2.2 | " |
| 7 | 50 | " | " | Dimethylacetamide 0.25 ml | " | Sus. |
| 8 | 34 | 3.2 | — | — | 1.6 | Soln. |
| 9 | 39 | 7.6 | — | 0.2 ml of physiological saline containing 80 mg of HCO-60* | 1.7 | Sus. |

Note 1:
Soln.: solution, Sus.: suspension
*polyoxyethylene (60) hardened castor oil

What is claimed is:
1. A chartreusin derivative of the formula (I) or a salt thereof;

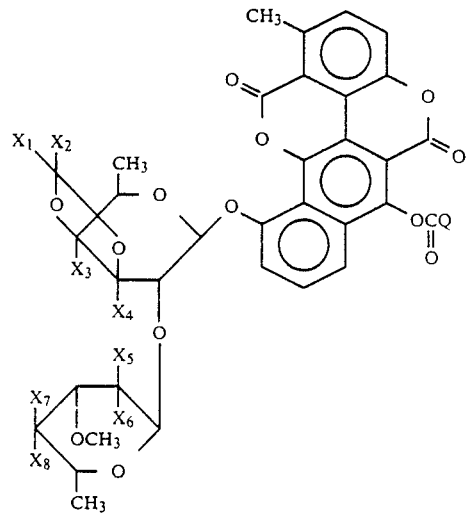

wherein
X$_1$ is a hydrogen atom or a C$_{1-3}$ alkyl group which may be substituted by a substituent selected from the group consisting of a halogen atom, a C$_{1-2}$ alkoxy group, and a C$_{1-2}$ alkylthio group;
X$_2$ is a C$_{1-3}$ alkyl group which may be substituted by a substituent selected from the group consisting of a halogen atom, a C$_{1-2}$ alkoxy group and a C$_{1-2}$ alkylthio group;
a C$_{1-2}$ alkylcarbonyl-C$_{1-2}$ alkyl group which may be substituted by a halogen atom;
a phenyl group;
a phenyl-C$_{1-2}$ alkyl group;
a furyl group; or
a thienyl group
wherein each of the phenyl group, the phenyl-C$_{1-2}$ alkyl group, the furyl group and the thienyl group may be substituted by a substituent selected from the group consisting of a halogen atom, a cyano group, a nitro group, a C$_{1-3}$ alkyl group, a C$_{1-3}$ alkoxy group, a $C_{1-3}$ alkylthio group, a $C_{1-3}$ alkylcarbonyl group, a $C_{1-3}$ alkoxycarbonyl group and a di-$C_{1-3}$ alkylamino group wherein each of the $C_{1-3}$ alkyl group, the $C_{1-3}$ alkoxy group, the $C_{1-3}$ alkylthio group, the $C_{1-3}$ alkylcarbonyl group, the $C_{1-3}$ alkoxycarbonyl group and the di-$C_{1-3}$ alkylamino group may be substituted by a halogen atom;

where both $X_1$ and $X_2$ are said alkyl groups, the total number of carbon atoms of these alkyl groups is 4 or less;

$X_1$ is a hydrogen atom where $X_2$ is said phenyl group; said phenyl-$C_{1-2}$ alkyl group, said furyl group, or said thienyl group;

$X_1$ and $X_2$, when taken together with the adjacent carbon atom, may form a $C_{3-7}$ cycloalkylidene which may be substituted by a halogen atom, a $C_{1-2}$ alkoxy group or a $C_{1-2}$ alkylthio group;

each of $X_3$, $X_4$, $X_6$ and $X_7$ is a hydrogen atom;

each of $X_5$ and $X_8$ is a hydroxyl group; and

Q is a substituent represented by any one of the formulas (d) to (i):

(d), $+R)_m\underset{Z_3}{\overset{Z_5}{\diagdown}}Z_4$ (e), $+R)_m\underset{Z_7\diagdown Z_3}{\overset{Z_6-Z_5}{\Big|}}Z_4$ (f), $+R)_m\underset{Z_8\diagdown Z_3}{\overset{Z_6\diagdown Z_5}{\Big|}}Z_4$ (g), $+R)_m\underset{Z_8\diagdown Z_3}{\overset{Z_7—Z_{11}—Z_6}{Z_{12}\diagdown Z_4\diagdown Z_5}}$ (h), $+R)_m\underset{Z_9\diagdown Z_3}{\overset{Z_8—Z_{11}\diagup Z_7\diagdown Z_6}{Z_{12}\diagdown Z_4\diagdown Z_5}}$ (i), $+R)_m\underset{Z_{10}\diagdown Z_3}{\overset{Z_8\diagup Z_{11}\diagup Z_7\diagdown Z_6}{Z_9 \quad Z_{12}\diagdown Z_4\diagdown Z_5}}$ wherein R is selected from the group consisting of
a $C_{1-11}$ alkanediyl group;
a $C_{2-11}$ alkenediyl group;
a $C_{2-11}$ alkynediyl group;
a $C_{3-10}$ cycloalkanediyl group; and
a $C_{5-10}$ cycloalkenediyl group wherein each of the $C_{1-11}$ alkanediyl group, the $C_{2-11}$ alkenediyl group, the $C_{2-11}$ alkynediyl group, the $C_{3-10}$ cycloalkanediyl group and the $C_{5-10}$ cycloalkenediyl group which may be substituted by a substituent selected from the group consisting of a halogen atom, a hydroxyl group, a mercapto group, a $C_{1-6}$ alkoxy group, a $C_{1-6}$ alkylthio group, a $C_{1-6}$ alkylsulfinyl group, a $C_{1-6}$ alkylsulfonyl group, an aminocarbonyl group, a hydroxycarbonyl group, a $C_{1-5}$ alkoxycarbonyl group, a phenyl group which may be substituted by a substituent selected from the group consisting of halogen, hydroxyl, mercapto, $C_{1-3}$ alkoxy and $C_{1-3}$ alkylthio, and a 3-indolyl group which may be substituted by halogen;

or R is a phenylene group which may be substituted by a substituent selected from the group consisting of a halogen atom, a hydroxyl group, a mercapto group, a $C_{1-6}$ alkoxy group, a $C_{1-6}$ alkylthio group, a $C_{1-6}$ alkylsulfinyl group, a $C_{1-6}$ alkylsulfonyl group, an aminocarbonyl group, a hydroxycarbonyl group, and a $C_{1-5}$ alkoxycarbonyl group;

m is zero or 1;

each of $Z_3$ through $Z_{10}$ is a $—CH_2—$ group, a $\underset{}{-\overset{|}{C}H-}$ group, a $\underset{}{-\overset{Y_1}{\overset{|}{C}}H-}$ group, a $\underset{}{-\overset{O}{\overset{\|}{C}}-}$ group, a $=CH—$ group, a $=\overset{|}{C}-$ group, a $=\overset{Y_1}{\overset{|}{C}}-$ group, a $—NH—$ group, a $-\overset{Y_2}{\overset{|}{N}}-$ group, a $-\overset{COY_3}{\overset{|}{N}}-$ group, a $=N—$ group, an oxygen atom or a sulfur atom;

each of $Z_{11}$ and $Z_{12}$ is a $-\overset{|}{C}H-$ group, a $-\overset{|}{\underset{Y_4}{\overset{|}{C}}}-$ group, a $=\overset{|}{C}-$ group or a $-\overset{|}{N}-$ group;

any one of $Z_3$ through $Z_{10}$ is a $-\overset{|}{C}H-$ group or a $=\overset{|}{C}-$ group each of the others being a substituent other than these two substituents, and any one of $Z_3$ through $Z_{10}$ is a $—NH—$ group, a $-\overset{Y_2}{\overset{|}{N}}-$ group, a $-\overset{COY_3}{\overset{|}{N}}-$ group, a $=N—$ group, an oxygen atom or a sulfur atom, $Y_1$ is selected from the group consisting of a halogen atom;
a hydroxyl group;
a mercapto group;
a nitro group;
a cyano group;
an amino group which may be substituted by a $C_{1-6}$ alkyl group which may be substituted by a substituent selected from the group consisting of halogen, hydroxyl, mercapto, $C_{1-3}$ alkoxy, and $C_{1-3}$ alkylthio, a $C_{1-3}$ alkylcarbonyl group which may be substituted by halogen, or a substituted carbonyl group having as the substituent any of the substituents represented by any one of the following formulas (a) to (c),

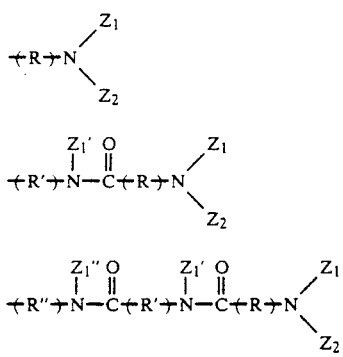

wherein each of R' and R" is the same as R,
each of $Z_1$, $Z'_1$ and $Z''_1$ is a hydrogen atom, or a $C_{1-6}$ alkyl group which may be substituted by a substituent selected from the group consisting of a halogen atom, a hydroxyl group, a mercapto group, a $C_{1-3}$ alkoxy group and a $C_{1-3}$ alkylthio group,
$Z_2$ is selected from the group consisting of a hydrogen atom;
a formyl group;
a $C_{1-6}$ alkyl group;
a $C_{1-6}$ alkylcarbonyl group; and
a benzoyl group
wherein each of the $C_{1-6}$ alkyl group, the $C_{1-6}$ alkylcarbonyl group and the benzoyl group may be substituted by the same substituent as substituent for said $C_{1-6}$ alkyl group as each of $Z_1$, $Z'_1$ and $Z''_1$,
or $Z_2$ is a benzyloxycarbonyl group which may be substituted by a halogen atom,
$Z_1$ and $Z_2$, when taken together with the nitrogen atom, may form a nitrogen-containing $C_{2-10}$ heterocyclic group which may be substituted by a substituent selected from the group consisting of a halogen atom, a hydroxyl group, a mercapto group, a $C_{1-3}$ alkyl group, a $C_{1-3}$ alkoxy group and a $C_{1-3}$ alkylthio group;
a $C_{1-3}$ alkyl group;
a $C_{1-3}$ alkoxy group;
a $C_{1-3}$ alkylthio group;
a $C_{1-3}$ alkylcarbonyloxy group;
a $C_{1-3}$ alkylcarbonylthio group;
a phenyl group;
wherein each of the $C_{1-3}$ alkyl group, the $C_{1-3}$ alkoxy group, the $C_{1-3}$ alkylthio group, the $C_{1-3}$ alkylcarbonyloxy group, the $C_{1-3}$ alkylcarbonylthio group and the phenyl group may be substituted by a substituent selected from the group consisting of a halogen atom, a hydroxyl group, a mercapto group, a cyano group, a $C_{1-3}$ alkylcarbonyl group which may be substituted by halogen and an amino group which may be substituted by a substituted carbonyl group having as the substituent any of the substituents represented by any one of the above formulas (a) to (c);
and a nitrogen-containing $C_{2-5}$ heterocyclic group may be substituted by a substituent selected from the group consisting of a halogen atom, a hydroxyl group, a mercapto group, a $C_{1-3}$ alkyl group, a $C_{1-3}$ alkoxy group, and a $C_{1-3}$ alkylthio group;

$Y_2$ is a $C_{1-3}$ alkyl group which may be substituted by the same substituent as substituent for said $C_{1-3}$-alkyl group as $Y_1$;
$Y_3$ is
a $C_{1-3}$ alkyl group,
a benzyloxy group,
wherein each of the $C_{1-3}$ alkyl group and the benzyloxy group may be substituted by a halogen atom, or a substituent represented by any one of formulas (a) to (c); and
$Y_4$ is a $C_{1-3}$ alkyl group which may be substituted by a halogen atom; the total number of atoms of Q other than the hydrogen atoms being 30 or less.

2. A chartreusin derivative according to claim 1, wherein the derivative is the exo form of 6-O-(2-(1-methylpyrrolyl)carbonyl)-3',4'-O-benzylidene-chartreusin.

3. A chartreusin derivative according to claim 1, wherein the derivative is the exo form of 6-O-(2-furylcarbonyl)-3',4'-O-benzylidene-chartreusin.

4. A chartreusin derivative according to claim 1, wherein the derivative is the exo form of 6-O-(2-thienylcarbonyl)-3',4'-O-benzylidene-chartreusin.

5. A chartreusin derivative according to claim 1, wherein the derivative is the exo form of 6-O-(4-(5-methyl-3-phenyl-isoxazolyl)-carbonyl)-3',4'-O-benzylidene-chartreusin.

6. A chartreusin derivative according to claim 1, wherein the derivative is the exo form of 6-O-(3-(1,2-dithiolanyl)pentanoyl)-3',4'-O-benzylidene-chartreusin.

7. A chartreusin derivative according to claim 1, wherein the derivative is the exo form of 6-O-(2-indolylcarbonyl)-3',4'-O-benzylidene-chartreusin.

8. A chartreusin derivative according to claim 1, wherein the derivative is the exo form of 6-O-(5-indolylcarbonyl)-3',4'-O-benzylidene-chartreusin.

9. A chartreusin derivative according to claim 1, wherein the derivative is the exo form of 6-O-(3-indolyl-acetyl)-3',4'-O-benzylidene-chartreusin.

10. A chartreusin derivative according to claim 1, wherein the derivative is the exo form of 6-O-(3,4-methylenedioxyphenylacetyl-3',4'-O-benzylidene-chartreusin.

11. A chartreusin derivative according to claim 1, wherein the derivative is the exo form of 6-O-(3-(1,4-dihydro-1-ethyl-4-oxo-1,8-naphthyridinyl)-carbonyl)-3',4'-O-benzylidene-chartreusin.

12. A chartreusin derivative according to claim 1, wherein the derivative is the exo form of 6-O-(2-(5-hydroxyindolyl)-carbonyl)-3',4'-O-benzylidene-chartreusin.

13. A chartreusin derivative according to claim 1, wherein the derivative is the exo form of 6-O-(5-(4-methyloxazolyl)-carbonyl)3',4'-O-benzylidene-chartreusin.

14. A chartreusin derivative according to claim 1, wherein the derivative is the exo form of 6-O-(4-(3-indolyl)-butanoyl)-3',4'-O-benzylidene-chartreusin.

15. A chartreusin derivative or a salt thereof according to claim 1, wherein $X_1$ is a hydrogen atom; $X_2$ is selected from the group consisting of a phenyl group, a furyl group, and a thienyl group
wherein each of the phenyl group, the furyl group and the thienyl group may be substituted by a substituent selected from the group consisting of a halogen atom, a cyano group, a nitro group, a $C_{1-3}$ alkyl group, a $C_{1-3}$ alkoxy group, a $C_{1-3}$ alkylthio group, a $C_{1-3}$ alkylcarbonyl group, a $C_{1-3}$ alkoxycarbonyl group and a di-$C_{1-3}$ alkylamino group
wherein each of the $C_{1-3}$ alkyl group, the $C_{1-3}$ alkoxy group, the $C_{1-3}$ alkylthio group, the $C_{1-3}$ alkylcarbonyl group, the $C_{1-3}$ alkoxycarbonyl group and the di-$C_{1-3}$ alkylamino group may be substituted by a halogen atom.

16. A chartreusin derivative or a salt thereof according to claim 1, wherein $X_1$ is a hydrogen atom; $X_2$ is a phenyl group which may be substituted by a substituent selected from the group consisting of a halogen atom, a cyano group, a nitrogen group, a $C_{1-3}$ alkyl group, a $C_{1-3}$ alkoxy group, a $C_{1-3}$ alkylthio group, a $C_{1-3}$ alkylcarbonyl group, a $C_{1-3}$ alkoxycarbonyl group and a di-$C_{1-3}$ alkylamino group
wherein each of the $C_{1-3}$ alkyl group, the $C_{1-3}$ alkoxy group, the $C_{1-3}$ alkylthio group, the $C_{1-3}$ alkylcarbonyl group, the $C_{1-3}$ alkoxycarbonyl group and the di-$C_{1-3}$ alkylamino group may be substituted by a halogen atom.

17. A chartreusin derivative or a salt thereof according to claim 16, wherein $X_1$ is a hydrogen atom; $X_2$ is a phenyl group which may be substituted in the o-position or the m-position of the benzene nucleus.

18. A chartreusin derivative or a salt thereof according to claim 16, which is in the exo form, and wherein $X_1$ is a hydrogen atom; $X_2$ is a phenyl group which may be substituted in the o-position or the m-position of the benzene nucleus; and Q is a substituent represented by formula selected from the group consisting of (d), (e) and (f):

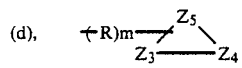

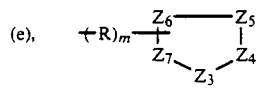

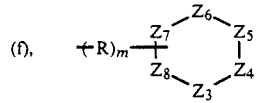

in which R is a $C_{1-11}$ alkanediyl group or a $C_{3-10}$ cycloalkanediyl group, wherein each of the $C_{1-11}$ alkanediyl group and the $C_{3-10}$ cyclo-alkanediyl group may be substituted by a substituent selected from the group consisting of a halogen atom, a hydroxyl group, a mercapto group, a $C_{1-6}$ alkoxy group, a $C_{1-6}$ alkylthio group, a $C_{1-6}$ alkylsulfinyl group, a $C_{1-6}$ alkylsulfonyl group, an aminocarbonyl group, a hydroxycarbonyl group, a $C_{1-5}$ alkoxycarbonyl group, a phenyl group which may be substituted by a substituent selected from the group consisting of halogen, hydroxyl, mercapto, $C_{1-3}$ alkoxy and $C_{1-3}$ alkylthio, and a 3-indolyl group which may be substituted by halogen;
m is zero or 1;
each of $Z_3$ through
$Z_8$ is selected from the group consisting of a —$CH_2$— group, a

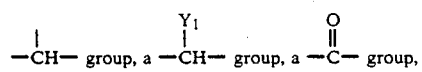

a =CH— group, a

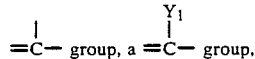

a —NH— group, a

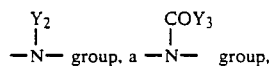

a =N— group, an oxygen atom and a sulfur atom;
any one of $Z_3$ through $Z_8$ is selected from the group consisting of a

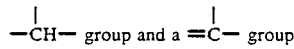

and, each of the others being a substituent other than these two substituents, and any one of $Z_3$ through $Z_8$ is selected from the group consisting of a —NH— group, a

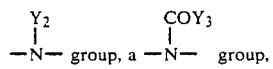

a =N— group, an oxygen atom and a sulfur atom,
$Y_1$ is selected from the group consisting of a halogen atom;
a hydroxyl group;
a mercapto group;
a nitro group;
a cyano group;
an amino group which may be substituted by a substituent selected from the group consisting of a $C_{1-6}$ alkyl group which may be substituted by a substituent selected from the group consisting of halogen, hydroxyl, mercapto, $C_{1-3}$ alkoxy and $C_{1-3}$ alkylthio, a $C_{1-3}$ alkylcarbonyl group which may be substituted by halogen or a substituted carbonyl group having as the substituent any of the substituents represented by any one of formulas (a) to (c),

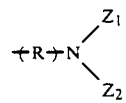

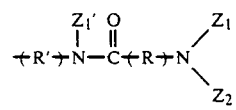

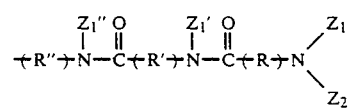

wherein each of R' and R'' is the same as R,
each of $Z_1$, $Z'_1$ and $Z''_1$ is a hydrogen atom, or a $C_{1-6}$ alkyl group which may be substituted by a substituent selected from the group consisting of a halogen atom, a hydroxyl group, a mercapto group, a $C_{1-3}$ alkoxy group and a $C_{1-3}$ alkylthio group,
$Z_2$ is selected from the group consisting of a hydrogen atom;

a formyl group;
a $C_{1-6}$ alkyl group;
a $C_{1-6}$ alkylcarbonyl group; and
a benzoyl group
  wherein each of the $C_{1-6}$ alkyl group, the $C_{1-6}$ alkylcarbonyl group and the benzoyl group may be substituted by the same substituent as substituent for said $C_{1-6}$ alkyl group as each of $Z_1$, $Z'_1$ and $Z''_1$,
or $Z_2$ is a benzyloxycarbonyl group which may be substituted by a halogen atom,
$Z_1$ and $Z_2$, when taken together with the nitrogen atom, may form a nitrogen-containing $C_{2-10}$ heterocyclic group which may be substituted by a substituent selected from the group consisting of a halogen atom, a hydroxyl group, a mercapto group, a $C_{1-3}$ alkyl group, a $C_{1-3}$ alkoxy group and a $C_{1-3}$ alkylthio group;
a $C_{1-3}$ alkyl group;
a $C_{1-3}$ alkoxy group;
a $C_{1-3}$ alkylthio group;
a $C_{1-3}$ alkylcarbonyloxy group;
a $C_{1-3}$ alkylcarbonylthio group;
a phenyl group;
  wherein each of the $C_{1-3}$ alkyl group, the $C_{1-3}$ alkoxy group, the $C_{1-3}$ alkylthio group, the $C_{1-3}$ alkylcarbonyloxy group, the $C_{1-3}$ alkylcarbonylthio group and the phenyl group may be substituted by a substituent selected from the group consisting of a halogen atom, a hydroxyl group, a mercapto group, a cyano group, a $C_{1-3}$ alkylcarbonyl group which may be substituted by halogen and an amino group which may be substituted by a substituted carbonyl group having as the substituent any of the substituents represented by any one of formulas (a) to (c);
and a nitrogen-containing $C_{2-5}$ heterocyclic group may be substituted by a substituent selected from the group consisting of a halogen atom, a hydroxyl group, a mercapto group, a $C_{1-3}$ alkyl group, a $C_{1-3}$ alkoxy group, and a $C_{1-3}$-alkylthio group;
$Y_2$ is a $C_{1-3}$ alkyl group which may be substituted by the same substituent as substituent for said $C_{1-3}$-alkyl group as $Y_1$;
$Y_3$ is
  a $C_{1-3}$ alkyl group,
  a benzyloxy group,
  wherein each of the $C_{1-3}$ alkyl group and the benzyloxy group may be substituted by a halogen atom, or a substituent represented by any one of formulas (a) to (c); and
$Y_4$ is a $C_{1-3}$ alkyl group which may be substituted by a halogen atom; the total number of atoms of Q other than the hydrogen atoms being 20 or less.

19. A chartreusin derivative or a salt thereof according to claim 1, which is in the exo form, and wherein each of $X_1$ is a hydrogen atom; $X_2$ is a m-fluorophenyl group and Q is a substituent represented by formula (e):

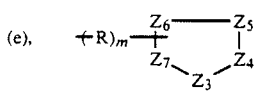

in which R is a $C_{1-5}$-alkanediyl group or a $C_{3-6}$ cycloalkanediyl group wherein each of the $C_{1-5}$ alkanediyl group and the $C_{3-6}$ cyclo-alkanediyl group may be substituted by a substituent selected from the group consisting of a halogen atom, a hydroxyl group, a mercapto group, a $C_{1-6}$ alkoxy group, a $C_{1-6}$ alkylthio group, a $C_{1-6}$ alkylsulfinyl group, a $C_{1-6}$ alkylsulfonyl group, an aminocarbonyl group, a hydroxycarbonyl group, a $C_{1-5}$ alkoxycarbonyl group, a phenyl group which may be substituted by a substituent selected from the group consisting of halogen, hydroxyl, mercapto, $C_{1-3}$ alkoxy and $C_{1-3}$ alkylthio, and a 3-indolyl group which may be substituted by halogen atom;
m is zero or 1;
each of $Z_3$ through $Z_7$ is a —$CH_2$— group, a

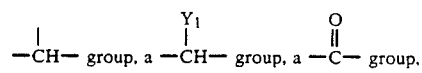

a =CH— group, a

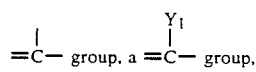

a —NH— group, a

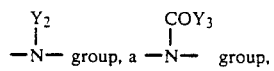

a =N— group, an oxygen atom or a sulfur atom;
any one of $Z_3$ through $Z_7$ is a

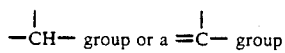

each of the others being a substituent other than these two substituents, and any one of $Z_3$ through $Z_7$ is a —NH— group, a

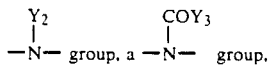

a =N— group, an oxygen atom or a sulfur atom,
$Y_1$ is selected from the group consisting of a halogen atom;
a hydroxyl group;
a mercapto group;
a nitro group;
a cyano group;
an amino group which may be substituted by a $C_{1-6}$ alkyl group which may be substituted by a substituent selected from the group consisting of halogen, hydroxyl, mercapto, $C_{1-3}$ alkoxy and $C_{1-3}$ alkylthio, a $C_{1-3}$ alkylcarbonyl group which may be substituted by halogen, or a substituted carbonyl group having as the substituent any of the substituents represented by any one of formulas (a) to (c),

-continued

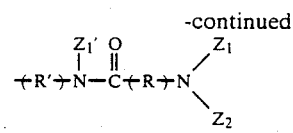
(b)

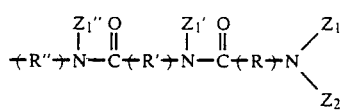
(c)

wherein each of R' and R" is the same as R, each of $Z_1$, $Z'_1$ and $Z''_1$ is a hydrogen atom, or a $C_{1-6}$ alkyl group which may be substituted by a substituent selected from the group consisting of a halogen atom, a hydroxyl group, a mercapto group, a $C_{1-3}$ alkoxy group and a $C_{1-3}$ alkylthio group, $Z_2$ is selected from the group consisting of a hydrogen atom;

a formyl group;

a $C_{1-6}$ alkyl group;

a $C_{1-6}$ alkylcarbonyl group; and a benzoyl group wherein each of the $C_{1-6}$ alkyl group, the $C_{1-6}$ alkylcarbonyl group and the benzoyl group may be substituted by the same substituent as substituent for said $C_{1-6}$ alkyl group as each of $Z_1$, $Z'_1$ and $Z''_1$, or $Z_2$ is a benzyloxycarbonyl group which may be substituted by a halogen atom, $Z_1$ and $Z_2$, when taken together with the nitrogen atom, may form a nitrogen-containing $C_{2-10}$ heterocyclic group which may be substituted by a substituent selected from the group consisting of a halogen atom, a hydroxyl group, a mercapto group, a $C_{1-3}$ alkyl group, a $C_{1-3}$ alkoxy group and a $C_{1-3}$ alkylthio group;

a $C_{1-3}$ alkyl group;

a $C_{1-3}$ alkoxy group;

a $C_{1-3}$ alkylthio group;

a $C_{1-3}$ alkylcarbonyloxy group;

a $C_{1-3}$ alkylcarbonylthio group;

a phenyl group;

wherein each of the $C_{1-3}$ alkyl group, or the $C_{1-3}$ alkoxy group, the $C_{1-3}$ alkylthio group, the $C_{1-3}$ alkylcarbonyloxy group, the $C_{1-3}$ alkylcarbonylthio group and the phenyl group may be substituted by a substituent selected from the group consisting of a halogen atom, a hydroxyl group, a mercapto group, a cyano group, a $C_{1-3}$ alkylcarbonyl group which may be substituted by halogen and an amino group which may be substituted by a substituted carbonyl group having as the substituent any of the substituents represented by any one of formulas (a) to (c);

and a nitrogen-containing $C_{2-5}$ heterocyclic group may be substituted by a substituent selected from the group consisting of a halogen atom, a hydroxyl group, a mercapto group, a $C_{1-3}$ alkyl group, a $C_{1-3}$ alkoxy group, and a $C_{1-3}$ alkylthio group;

$Y_2$ is a $C_{1-3}$ alkyl group which may be substituted by the same substituent as substituent for said $C_{1-3}$-alkyl group as $Y_1$;

$Y_3$ is a $C_{1-3}$ alkyl group, a benzyloxy group, wherein each of the $C_{1-3}$ alkyl group and the benzyloxy group may be substituted by a halogen atom, or a substituent represented by any one of the above formula (a) to (c); and $Y_4$ is a $C_{1-3}$ alkyl group which may be substituted by a halogen atom; the total number of atoms of Q other than the hydrogen atoms being 15 or less.

20. A chartreusin derivative or a salt thereof according to claim 1, which is in the exo form, wherein each of $X_1$, $X_3$, $X_4$, $X_6$ and $X_7$ is a hydrogen atom; $X_2$ is a phenyl group; each of $X_5$ and $X_8$ is a hydroxyl group; and Q is a substituent represented by formula (e):

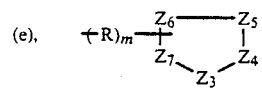
(e), in which substituent R is selected from the group consisting of a $C_{1-5}$ alkanediyl group which may be substituted by a substituent selected from the group consisting of a halogen atom, a hydroxyl group, a mercapto group, a $C_{1-6}$ alkoxy group, a $C_{1-6}$ alkylthio group, a $C_{1-6}$ alkylsulfinyl group, a $C_{1-6}$ alkylsulfonyl group, an aminocarbonyl group, a hydroxycarbonyl group, a $C_{1-5}$ alkoxycarbonyl group, a phenyl group which may be substituted by a substituent selected from the group consisting of halogen, hydroxyl, mercapto, $C_{1-3}$ alkoxy and $C_{1-3}$ alkylthio, and a 3-indolyl group which may be substituted by halogen atom;

m is zero or 1;

each of $Z_3$ through $Z_7$ is a —CH$_2$— group, a

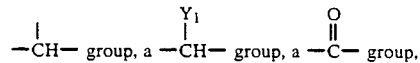

a =CH— group, a

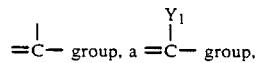

a —NH— group, a

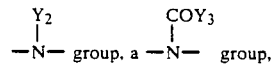

a =N— group, an oxygen atom or a sulfur atom, $Y_1$ is a halogen atom;

a hydroxyl group;

a mercapto group;

a nitro group;

a cyano group;

an amino group which may be substituted by a $C_{1-6}$ alkyl group which may be substituted by a substituent selected from the group consisting of halogen, hydroxyl, mercapto, $C_{1-3}$ alkoxy, and $C_{1-3}$ alkylthio, a $C_{1-3}$ alkylcarbonyl group which may be substituted by halogen, or a substituted carbonyl group having as the substituent any of the substituents represented by any one of formulas (a) to (c),

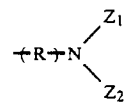
(a)

-continued

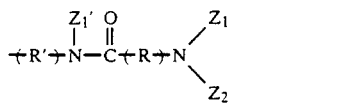
(b)

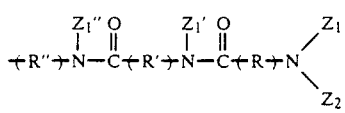
(c)

wherein each of R' and R" is the same as R, each of $Z_1$, $Z'_1$ and $Z''_1$ is a hydrogen atom, or a $C_{1-6}$ alkyl group which may be substituted by a substituent selected from the group consisting of a halogen atom, a hydroxyl group, a mercapto group, a $C_{1-3}$ alkoxy group and a $C_{1-3}$ alkylthio group, $Z_2$ is selected from the group consisting of a hydrogen atom;
a formyl group;
a $C_{1-6}$ alkyl group;
a $C_{1-6}$ alkylcarbonyl group; and
a benzoyl group
wherein each of the $C_{1-6}$ alkyl group, the $C_{1-6}$ alkylcarbonyl group and the benzoyl group may be substituted by the same substituent as substituent for said $C_{1-6}$ alkyl group as each of $Z_1$, $Z'_1$ and $Z''_1$,
or $Z_2$ is a benzyloxycarbonyl group which may be substituted by a halogen atom, $Z_1$ and $Z_2$, when taken together with the nitrogen atom, may form a nitrogen-containing $C_{2-10}$ heterocyclic group which may be substituted by a substituent selected from the group consisting of a halogen atom, a hydroxyl group, a mercapto group, a $C_{1-3}$ alkyl group, a $C_{1-3}$ alkoxy group and a $C_{1-3}$ alkylthio group;

a $C_{1-3}$ alkyl group;
a $C_{1-3}$ alkoxy group;
a $C_{1-3}$ alkylthio group;
a $C_{1-3}$ alkylcarbonyloxy group;
a $C_{1-3}$ alkylcarbonylthio group;
a phenyl group;
wherein each of the $C_{1-3}$ alkyl group, or the $C_{1-3}$ alkoxy group, the $C_{1-3}$ alkylthio group, the $C_{1-3}$ alkylcarbonyloxy group, the $C_{1-3}$ alkylcarbonylthio group and the phenyl group may be substituted by a substituent selected from the group consisting of a halogen atom, a hydroxyl group, a mercapto group, a cyano group, a $C_{1-3}$ alkylcarbonyl group which may be substituted by halogen and an amino group which may be substituted by a substituted carbonyl group having as the substituent any of the substituents represented by any one of formulas (a) to (c);

and a nitrogen-containing $C_{2-5}$ heterocyclic group may be substituted by a substituent selected from the group consisting of a halogen atom, a hydroxyl group, a mercapto group, a $C_{1-3}$ alkyl group, a $C_{1-3}$ alkoxy group, and a $C_{1-3}$ alkylthio group;

$Y_2$ is a $C_{1-3}$ alkyl group which may be substituted by the same substituent as substituent for said $C_{1-3}$-alkyl group as $Y_1$;

$Y_3$ is
a $C_{1-3}$ alkyl group,
a benzyloxy group,
wherein each of the $C_{1-3}$ alkyl group and the benzyloxy group may be substituted by a halogen atom, or a substituent represented by any one of the above formula (a) to (c); and $Y_4$ is a $C_{1-3}$ alkyl group which may be substituted by a halogen atom; the total number of atoms of Q other than the hydrogen atoms being 15 or less.

* * * * *